US011274325B2

(12) United States Patent
Mallipeddi et al.

(10) Patent No.: US 11,274,325 B2
(45) Date of Patent: Mar. 15, 2022

(54) SIALYLTRANSFERASES AND USES THEREOF

(71) Applicant: Glycosyn LLC, Woburn, MA (US)

(72) Inventors: Srikrishnan Mallipeddi, Arlington, MA (US); Matthew Ian Heidtman, Edina, MN (US); Massimo Merighi, Somerville, MA (US); John M. McCoy, Reading, MA (US)

(73) Assignee: Glycosyn LLC, Waltham, MA (US)

( * ) Notice: Subject to any disclaimer, the term of this patent is extended or adjusted under 35 U.S.C. 154(b) by 86 days.

(21) Appl. No.: 16/221,193

(22) Filed: Dec. 14, 2018

(65) Prior Publication Data

US 2019/0218582 A1 Jul. 18, 2019

Related U.S. Application Data

(60) Provisional application No. 62/599,481, filed on Dec. 15, 2017.

(51) Int. Cl.

| | |
|---|---|
| ***C12P 19/02*** | (2006.01) |
| ***C12N 15/00*** | (2006.01) |
| ***C12N 9/24*** | (2006.01) |
| ***C12N 9/40*** | (2006.01) |
| ***C12N 9/10*** | (2006.01) |
| ***C07K 14/245*** | (2006.01) |
| ***C12N 9/38*** | (2006.01) |
| ***C12N 9/12*** | (2006.01) |

(52) U.S. Cl.

CPC ............ *C12P 19/02* (2013.01); *C07K 14/245* (2013.01); *C12N 9/1051* (2013.01); *C12N 9/1081* (2013.01); *C12N 9/1085* (2013.01); *C12N 9/1241* (2013.01); *C12N 9/2471* (2013.01); *C12Y 204/01065* (2013.01); *C12Y 204/01149* (2013.01); *C12Y 204/99007* (2013.01); *C12Y 205/01056* (2013.01); *C12Y 207/07043* (2013.01); *C12Y 302/01023* (2013.01); *C12Y 302/01183* (2015.07)

(58) Field of Classification Search

CPC .... C12N 15/102; C12N 15/09; C12N 9/1048; C12N 9/1051; C12Y 204/99007; C12Y 204/99008; C12Y 302/01018; C12Y 204/01149; C12P 19/02; C07K 14/245

USPC .... 435/15, 97, 193, 52.2, 252.3, 252.33, 84, 435/101, 200

See application file for complete search history.

(56) References Cited

U.S. PATENT DOCUMENTS

| | | | |
|---|---|---|---|
| 2011/0014661 A1 | 1/2011 | Samain | |
| 2012/0282659 A1 | 11/2012 | Yamamoto et al. | |
| 2014/0031541 A1 | 1/2014 | Heidtman et al. | |
| 2016/0024543 A1 | 1/2016 | Merighi et al. | |

FOREIGN PATENT DOCUMENTS

| | | |
|---|---|---|
| WO | 2007/101862 A1 | 9/2007 |
| WO | 2019/118829 A2 | 6/2019 |

OTHER PUBLICATIONS

Devos et al., Proteins: Structure, Function and Genetics, 2000, vol. 41: 98-107.*

Whisstock et al., Quarterly Reviews of Biophysics 2003, vol. 36 (3): 307-340.*

Witkowski et al., Biochemistry 38:11643-11650, 1999.*

Kisselev L., Structure, 2002, vol. 10: 8-9.*

International preliminay report, 2020, pp. 1-15.*

Altschul, et al., "Basic Local Alignment Search Tool", Journal of Molecular Biology, Oct. 1990, 215(3):403-410.

Altschul, et al., "Gapped BLAST and PSI-BLAST: a New Generation of Protein Database Search Programs", Nucleic Acids Research, Sep. 1, 1997, 25(17):3389-3402.

Audry, et al., "Current trends in the structure-activity relationships of sialyltransferases", Glycobiology, 2011, 21(6):716-726.

Bachmann, et al., "Pedigrees of Some Mutant Strains of *Escherichia coli* K-12", Bacteriological Reviews, 1972, 36(4):525-557.

Bao, et al., "Simultaneous Quantification of Sialyloligosaccharides from Human Milk by Capillary Electrophoresis", Analytical Biochemistry, Nov. 15, 2007, 370(2):206-214.

Belfort, et al., "Characterization of the *Escherichia coli* thyA Gene and its Amplified Thymidylate Synthase Product", Proceedings of the National Academy of Sciences, May 1983, 80(7):1858-1861.

Bode, et al., "Structure-Function Relationships of Human Milk Oligosaccharides", Advances in Nutrition, May 1, 2012, 3(3):383S-391S.

Chothia, et al., "The relation between the divergence of sequence and structure in proteins", The EMBO Journal, 1986, 5(4):823-826.

Court, et al., "Genetic Engineering Using Homologous Recombination", Annual Review of Genetics, 2002, 36:361-388.

Danchin, "Cells need safety valves", BioEssays, 2009, 31(7):769-773.

Deng, et al., "Directed evolution and characterization of *Escherichia coli* glucosamine synthase", Biochimie, May 2006, 88(5):419-429.

Drouillard, et al., "Efficient Synthesis of 6'-Sialyllactose, 6,6'-Disialyllactose, and 6'-KDO-Lactose by metabolically Engineered *E. coli* Expressing a Multifunctional Sialyltransferase from the *Photobacterium* Sp. JT-ISH-224", Carbohydrate Research, Jul. 2, 2010, 345(10):1394-1399.

Dumon, et al., "Assessment of the Two Helicobacter pylori α-1,3-Fucosyltransferase Ortholog Genes for the Large-Scale Synthesis of LewisX Human Milk Oligosaccharides by Metabolically Engineered *Escherichia coli*", Biotechnology Progress, 2004, 20(2):412-419.

(Continued)

*Primary Examiner* — Robert B Mondesi
*Assistant Examiner* — Mohammad Y Meah
(74) *Attorney, Agent, or Firm* — Mintz Levin Cohn Ferris Glovsky and Popeo, P.C.; Ingrid A. Beattie

(57) ABSTRACT

Provided herein, inter alia, are methods, bacteria, nucleic acids, and polypeptides for producing sialylated oligosaccharides.

51 Claims, 18 Drawing Sheets
(12 of 18 Drawing Sheet(s) Filed in Color)

Specification includes a Sequence Listing.

(56) References Cited

OTHER PUBLICATIONS

Dumon, et al., "Production of Lewis x Tetrasaccharides by Metabolically Engineered *E. coli*", ChemBiochem, 2006, 7(2):359-365.
Guo, et al., "Modulating the regioselectivity of a Pasteurella multocida sialyltransferase for biocatalytic production of 3'- and 6'-sialyllactose", Enzyme and Microbial Technology, Jun. 2015, 78:54-62.
Hopkins, et al., "Transport and catabolism of the sialic acids N-glycolylneuraminic acid and 3-keto-3-deoxy-D-glycero-D-galactonononic acid by *Escherichia coli* K-12", FEMS Microbiology Letters, 2013, 347:14-22.
Kakuta, et al., "Crystal Structure of *Vibrionaceae photobacterium* sp. JT-ISH-224 α2,6-Sialyltransferase in a Ternary Complex With Donor Product CMP and Acceptor Substrate Lactose: Catalytic Mechanism and Substrate Recognition", Glycobiology, Oct. 25, 2007, 18(1):66-73.
Kunz, et al., "Oligosaccharides in Human Milk: Structural, Functional, and Metabolic Aspects", Annual Review of Nutrition, 2000, 20:699-722.
La Vallie, et al., "A Thioredoxin Gene Fusion Expression System That Circumvents Inclusion Body Formation in the *E. coli* Cytoplasm", Biotechnology, Feb. 1993, 11(2):187-193.
La Vallie, et al., "Thioredoxin as A Fusion Partner for Production of Soluble Recombinant Proteins in *Escherichia coli*", Methods in Enzymology, 2000, 326:322-340.
Li, et al., "Characterization of a Novel α1,2-Fucosyltransferase of *Escherichia coli* O128:612 and Functional Investigation of its Common Motif", Biochemistry, Jan. 8, 2008, 47(1):378-387.
Li, et al., "Identification of a New α1,2-Fucosyltransferase Involved in O-Antigen Biosynthesis of *Escherichia coli* O86: B7 and Formation of H-Type 3 Blood Group Antigen", Biochemistry, 2008, 47(44):11590-11597.
Li, et al., "Positive and negative selection using the tetA-sacB cassette: recombineering and P1 transduction in *Escherichia coli*", Nucleic Acids Research, Nov. 2013, 41(22):1-8(e204).
Mao, et al., "Engineering the *E. coli* UDP-Glucose Synthesis Pathway for Oligosaccharide Synthesis", Biotechnology Progress, 2006, 22(2):369-374.
Mcarthur, et al., "Converting Pasteurella multocida α2-3-sialyltransferase 1 (PmST1) to a regioselective α2-6-sialyltransferase by saturalion mutagenesis and regioselective screening", Organic & Biomolecular Chemistry, 2017, 15(7):1700-1709.
Mieschendahl, et al., "A Novel Prophage Independent TRP Regulated Lambda PL Expression System", Nature Biotechnology, 1986, 4(9):802-808.
Newburg, et al., "Protection of the Neonate by the Innate Immune System of Developing Gut and of Human Milk", Pediatric Research, 2007, 61:2-8.
Reichenbach, et al., "The Small RNA GlmY Acts Upstream of the sRNA GlmZ in the Activation of glms Expression and is Subject to Regulation by Polyadenylation in *Escherichia coli*", Nucleic Acids Research, 2008, 36(8):2570-2580.
Ruffing, et al., "Metabolic Engineering of Microbes for Oligosaccharide and Polysaccharide Synthesis", Microbial Cell Factories, Jul. 21, 2006, 5(25):1-9.
Schmolzer, et al., "Characterization of a multifunctional α2,3-sialyltransferase from Pasteurella dagmatis", Glycobiology, 2013, 23(11):1293-1304.
Schmolzer, et al., "Complete switch from α-2,3- to α-2,6-regioselectivity in Pasteurella dagmatis β-D-galactoside sialyltransferase by active-site redesign", Chemical Communications, 2015, 51(15):3083-3086.
Schur, et al., "Characterization of α2,3- and α2,6-sialyltransferases from Helicobacter acinonychis", Glycobiology, 2012, 22(7):997-1006.
Styczynski, et al., "BLOSUM62 Miscalculations Improve Search Performance", Nature Biotechnology, 2008, 26(3):274-275.
National Center for Biotechnology Information "putative sialic acid synthase [Campylobacter jejuni]", GenBank Accession No. AAK91726.1, Jul. 23, 2016, 1 page.
National Center for Biotechnology Information "Putative N-Acetylglucosamine-6-Phosphate 2-Epimerase [Campylobacter jejuni]", GenBank Accession No. AAK91727.1, Jul. 23, 2016, 2 pages.
National Center for Biotechnology Information "CMP-Neu5Ac Synthetase [Campylobacter jejuni]", GenBank Accession No. AAK91728.1, Jul. 23, 2016, 2 pages.
National Center for Biotechnology Information "hypothetical protein HD_0053 [[Haemophilus] ducreyi 35000HP]", GenBank Accession No. AAP95068.1, Aug. 14, 2018, 1 page.
National Center for Biotechnology Information "alpha-2,3/2,6-sialyltransferase/sialidase [Pasteurella multocida]", GenBank Accession No. AAY89061.1, Jun. 27, 2006, 1 page.
National Center for Biotechnology Information "hypothetical protein WQG_5820 [Bibersteinia trehalosi USDA-ARS-USMARC-192]", GenBank Accession No. AGH37861.1, Apr. 18, 2013, 1 page.
National Center for Biotechnology Information "DNA-Binding Transcriptional Dual Regulator [*Escherichia coli* Str. K-12 Substr. W3110]", GenBank Accession No. BAA35319.1, Sep. 29, 2018, 13 pages.
National Center for Biotechnology Information "Predicted N-Acetylmannosamine Kinase [*Escherichia coli* Str. K-12 Substr. W3110]", GenBank Accession No. BAE77265.1, Sep. 29, 2018, 13 pages.
National Center for Biotechnology Information "Beta-Galactoside Alpha-2,6-Sialyltransferase [*Photobacterium* sp. JT-ISH-224]", GenBank Accession No. BAF92026.1, Mar. 22, 2008, 2 pages.
National Center for Biotechnology Information "bifunctional alpha-2,3/-2,8-sialyltransferase [*Helicobacter acinonychis* str. *Sheeba*]", GenBank Accession No. CAK00018.1, Feb. 27, 2015, 1 page.
National Center for Biotechnology Information "*Escherichia coli* nanA Gene for N-Acetylneuraminate Lyase, Complete Cds", GenBank Accession No. D00067.1, Jun. 15, 2010, 2 pages.
National Center for Biotechnology Information "Kluyveromyces Lactis Beta-D-Galactosidase (LAC4) Gene, Complete CDS", GenBank Accession No. M84410.1, Apr. 27, 1993, 2 pages.
National Center for Biotechnology Information "L-Glutamine:D-Fructose-6-Phosphate aminotransferase [*Escherichia coli* str. K-12 substr. MG1655]", GenBank Accession No. NP_418185.1, Oct. 11, 2014, 4 pages.
National Center for Biotechnology Information "*E. coli* lacY Gene (Codes for Lactose permease)", GenBank Accession No. V00295.1, Jul. 26, 2016, 3 pages.
National Center for Biotechnology Information "hypothetical protein [Helicobacter pylori]", GenBank Accession No. WP_000743106.1, May 5, 2013, 1 page.
National Center for Biotechnology Information "hypothetical protein [Actinobacillus ureae]", GenBank Accession No. WP_005625206.1, Jun. 4, 2013, 1 page.
National Center for Biotechnology Information "hypothetical protein [Pasteurella dagmatis]", GenBank Accession No. WP_005762792.1, Jun. 4, 2013, 1 page.
National Center for Biotechnology Information "acylneuraminate cytidylyltransferase family protein [Vibrio brasiliensis]", GenBank Accession No. WP_006881452.1, Jul. 24, 2017, 1 page.
National Center for Biotechnology Information "bifunctional alpha-2,3/-2,8-sialyltransferase [Helicobacter cetorum]", GenBank Accession No. WP_014661583.1, May 19, 2013, 1 page.
National Center for Biotechnology Information "Multispecies: hypothetical protein [Alistipes]", GenBank Accession No. WP_018695526.1, Aug. 17, 2015, 1 page.
National Center for Biotechnology Information "Sialyltransferase 0160 [Shewanella piezotolerans]", GenBank Accession No. WP_020915003.1, Jul. 25, 2013, 1 page.
National Center for Biotechnology Information "Putative Alpha-2,3/2,6-sialyltransferase/sialidase [Avibacterium paragallinarum]", GenBank Accession No. WP_021724759.1, Feb. 16, 2018, 1 page.
National Center for Biotechnology Information "N-acetylneuraminate synthase [Flavobacterium limnosediminis]", GenBank Accession No. WP_023580510.1, Feb. 8, 2016, 1 page.

(56) References Cited

OTHER PUBLICATIONS

National Center for Biotechnology Information "Sialyltransferase 0160 [Shewanella piezotolerans WP3]", GenBank Accession No. YP_002314261.1, Dec. 17, 2014, 2 pages.
National Center for Biotechnology Information "UDP-N-acetylglucosamine 2-epimerase [*Escherichia coli* S88]", GenBank Accession No. YP_002392936.1, Dec. 16, 2014, 2 pages.
"Bifunctional alpha-2,3/-2,8-sialyltransferase", UniProtKB Accession No. I0EP47_HELC0, Jun. 13, 2012.
"Bifunctional alpha-2,3/-2,8-sialyltransferase", UniProtKB Accession No. A0A0E0WB72_HELPX, May 27, 2015.
"Putative Alpha-2,3/2,6-sialyltransferase/sialidase", UniProtKB Accession No. S6F5P9_AVIPA, Oct. 16, 2013.
Dailidiene et al. (Jan. 2004) "Helicobacter acinonychis: Genetic and Rodent Infection Studies of a Helicobacter pylori-Like Gastric Pathogen of Cheetahs and Other Big Cats", Journal of Bacteriology, 186(2):356-365.
Sugiarto et al. (May 14, 2012) "A Sialyltransferase Mutant with Decreased Donor Hydrolysis and Reduced Sialidase Activities for Directly Sialylating Lewis", ACS Chemical Biology, 7(7):1232-1240.

* cited by examiner

| | | 1 | 2 | 3 | 4 | 5 | 6 | 7 | 8 | 9 | 10 |
|---|---|---|---|---|---|---|---|---|---|---|---|
| Pst6 Photobacterium sp. 224 | 1 | 100.00 | 26.09 | 18.85 | 16.39 | 15.92 | 13.25 | 8.94 | 10.32 | 7.94 | 6.46 |
| BstC Avibacterium paragallinarum | 2 | 26.09 | 100.00 | 21.82 | 21.51 | 24.48 | 11.39 | 16.04 | 10.33 | 7.74 | 6.94 |
| Bstj Shewanella piezotolerans | 3 | 18.85 | 21.82 | 100.00 | 18.10 | 19.53 | 9.22 | 10.84 | 8.84 | 6.67 | 6.91 |
| BstB Bibersteinia trealosi | 4 | 16.39 | 21.51 | 18.10 | 100.00 | 35.07 | 8.24 | 21.90 | 9.00 | 7.17 | 6.00 |
| BstE Haemophilus ducreyi | 5 | 15.92 | 24.48 | 19.53 | 35.07 | 100.00 | 7.75 | 26.65 | 10.76 | 8.10 | 6.69 |
| BstH Alistipes (multispecies) | 6 | 13.25 | 11.39 | 9.22 | 8.24 | 7.75 | 100.00 | 6.60 | 6.19 | 5.65 | 5.15 |
| BstD Actinobacillus ureae | 7 | 8.94 | 16.04 | 10.84 | 21.90 | 26.65 | 6.60 | 100.00 | 7.08 | 9.29 | 7.77 |
| HAC1268 Helicobacter acinonychis | 8 | 10.32 | 10.33 | 8.84 | 9.00 | 10.76 | 6.19 | 7.08 | 100.00 | 70.62 | 52.89 |
| BstM Helicobacter pylori | 9 | 7.94 | 7.74 | 6.67 | 7.17 | 8.10 | 5.65 | 9.29 | 70.62 | 100.00 | 68.47 |
| BstN Helicobacter cetorum | 10 | 6.46 | 6.94 | 6.91 | 6.00 | 6.69 | 5.15 | 7.77 | 52.89 | 68.47 | 100.00 |

FIG. 2

| | Ala | Arg | Asn | Asp | Cys | Gln | Glu | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|---|---|
| Ala | 4 | | | | | | | | | | | | | | | | | | | |
| Arg | -1 | 5 | | | | | | | | | | | | | | | | | | |
| Asn | -2 | 0 | 6 | | | | | | | | | | | | | | | | | |
| Asp | -2 | -2 | 1 | 6 | | | | | | | | | | | | | | | | |
| Cys | 0 | -3 | -3 | -3 | 9 | | | | | | | | | | | | | | | |
| Gln | -1 | 1 | 0 | 0 | -3 | 5 | | | | | | | | | | | | | | |
| Glu | -1 | 0 | 0 | 2 | -4 | 2 | 5 | | | | | | | | | | | | | |
| Gly | 0 | -2 | 0 | -1 | -3 | -2 | -2 | 6 | | | | | | | | | | | | |
| His | -2 | 0 | 1 | -1 | -3 | 0 | 0 | -2 | 8 | | | | | | | | | | | |
| Ile | -1 | -3 | -3 | -3 | -1 | -3 | -3 | -4 | -3 | 4 | | | | | | | | | | |
| Leu | -1 | -2 | -3 | -4 | -1 | -2 | -3 | -4 | -3 | 2 | 4 | | | | | | | | | |
| Lys | -1 | 2 | 0 | -1 | -3 | 1 | 1 | -2 | -1 | -3 | -2 | 5 | | | | | | | | |
| Met | -1 | -1 | -2 | -3 | -1 | 0 | -2 | -3 | -2 | 1 | 2 | -1 | 5 | | | | | | | |
| Phe | -2 | -3 | -3 | -3 | -2 | -3 | -3 | -3 | -1 | 0 | 0 | -3 | 0 | 6 | | | | | | |
| Pro | -1 | -2 | -2 | -1 | -3 | -1 | -1 | -2 | -2 | -3 | -3 | -1 | -2 | -4 | 7 | | | | | |
| Ser | 1 | -1 | 1 | 0 | -1 | 0 | 0 | 0 | -1 | -2 | -2 | 0 | -1 | -2 | -1 | 4 | | | | |
| Thr | 0 | -1 | 0 | -1 | -1 | -1 | -1 | -2 | -2 | -1 | -1 | -1 | -1 | -2 | -1 | 1 | 5 | | | |
| Trp | -3 | -3 | -4 | -4 | -2 | -2 | -3 | -2 | -2 | -3 | -2 | -3 | -1 | 1 | -4 | -3 | -2 | 11 | | |
| Tyr | -2 | -2 | -2 | -3 | -2 | -1 | -2 | -3 | 2 | -1 | -1 | -2 | -1 | 3 | -3 | -2 | -2 | 2 | 7 | |
| Val | 0 | -3 | -3 | -3 | -1 | -2 | -2 | -3 | -3 | 3 | 1 | -2 | 1 | -1 | -2 | -2 | 0 | -3 | -1 | 4 |

FIG. 14

| 6'-Sialyllactose (84%) | | Chemical shift (ppm) | | | | | | | | |
|---|---|---|---|---|---|---|---|---|---|---|
| No. | Residue | 1 | 2 | 3 | 4 | 5 | 6 | 7 | 8 | 9 |
| Aa | 4-α-Glc | 5.218 | 3.60 | 3.84 | 3.62 | 3.95 | | | | |
| | | *94.6* | *73.9* | *74.3* | *82.4* | *72.8* | | | | |
| Ab | 4-β-Glc | 4.661 | 3.31 | 3.64 | 3.61 | 3.6 | 3.95 | 3.78 | | |
| | | *98.5* | *76.6* | *77.4* | *82.4* | *77.5* | *63.2* | | | |
| B | 6-β-Gal | 4.421 | 3.52 | 3.65 | 3.93 | 3.8 | 3.97 | 3.59 | | |
| | | *106.1* | *73.6* | *75.2* | *71.3* | *76.6* | *66.4* | | | |
| C | α-NeuAc | | | 2.707/1.736 | 3.55 | 3.84 | 3.71 | 3.64 | 3.88 | 3.87/3.63 |
| | | *176.4* | *103.1* | *42.8* | *71.1* | *54.7* | *75.4* | *71.1* | *74.6* | *65.4* |

| 3'-Sialyllactose (16%) | | Chemical shift (ppm) | | | | | | | | |
|---|---|---|---|---|---|---|---|---|---|---|
| | | 1 | 2 | 3 | 4 | 5 | 6 | 7 | 8 | 9 |
| Aa | 4-α-Glc | 5.217 | 3.6 | 3.87 | 3.66 | 3.95 | 3.82 | | | |
| | | *94.6* | *74.2* | *74.3* | *81.0* | *72.8* | | | | |
| Ab | 4-β-Glc | 4.657 | 3.28 | 3.66 | 3.66 | 3.62 | | | | |
| | | *98.5* | *76.6* | *77.3* | *81.0* | *77.3* | | | | |
| B | 3-β-Gal | 4.524 | 3.57 | 4.11 | 3.96 | 3.7 | | | | |
| | | *105.5* | *72.2* | *78.3* | *70.4* | *78.0* | | | | |
| C | α-NeuAc | | | 2.752/1.793 | 3.55 | 3.84 | 3.71 | 3.64 | 3.88 | 3.87/3.63 |
| | | *176.7* | *102.7* | *42.5* | *71.1* | *54.7* | *75.4* | *71.1* | *74.6* | *65.4* |

FIG. 15

SIALYLTRANSFERASES AND USES THEREOF

CROSS REFERENCE TO RELATED APPLICATIONS

This application claims priority to U.S. Provisional Application No. 62/599,481, filed Dec. 15, 2017, which is incorporated herein in its entirety for all purposes.

REFERENCE TO A SEQUENCE LISTING

The content of the text file named "037847-522001US_SequenceListing_ST25.txt", which was created on Dec. 11, 2018, and is 124,706 bytes in size, is hereby incorporated by reference in its entirety.

BACKGROUND OF THE INVENTION

Lactose is the major nutritional carbohydrate of all mammalian milks, however human milk also contains a diverse and abundant set of more complex neutral and acidic sugars, collectively known as the human milk oligosaccharides (hMOS) (Kunz, C., et al. (2000). Annu Rev Nutr 20, 699-722; Bode, L., and Jantscher-Krenn, E. (2012). Adv Nutr 3, 383S-391S). Hundreds of different hMOS species have been identified, and their rich structural diversity and overall abundance is unique to humans. These molecules are not absorbed well by the human gut and are not utilized by infants for direct nutrition, but they have been shown to serve critical roles in the establishment of a healthy gut microbiome, in gut development, in disease prevention, and in immune function (Newburg, D. S., and Walker, W. A. (2007). Pediatr Res 61, 2-8).

New methods are needed for producing purified human milk oligosaccharides.

BRIEF SUMMARY OF THE INVENTION

Provided herein are, inter alia, methods, enzymes, compositions, and genetically modified bacteria for producing sialylated oligosaccharide. The enzymes provided herein are able to sialylate lactose, generating either α(2,3) glycosidic linkages, α(2,6) linkages, or mixtures of α(2,3) and α(2,6) linkages to lactose, and as such are especially advantageous in producing oligosaccharide molecules identical to the lactose-based molecules of human milk. In an aspect, a method for producing a sialylated oligosaccharide in a bacterium is provided. In some embodiments, the bacterium includes an exogenous lactose-utilizing sialyltransferase enzyme, e.g., an α(2,3) sialyltransferase or an α(2,6) sialyltransferase. In various embodiments, the enzyme has an amino acid sequence that is from 5% to 30% identical to the amino acid sequence of Pst6-224 (SEQ ID NO: 1) over a stretch of at least 250 amino acids. In certain embodiments, the enzyme has an amino acid sequence that is from 45% to 75% identical to the amino acid sequence of HAC1268 (SEQ ID NO: 8) over a stretch of at least 250 amino acids.

In an aspect, included herein is an isolated bacterium comprising an exogenous lactose-utilizing sialyltransferase enzyme. In some embodiments, the enzyme has an amino acid sequence that is from 5% to 30% identical to the amino acid sequence of Pst6-224 (SEQ ID NO: 1) over a stretch of at least 250 amino acids. In certain embodiments, the enzyme has amino acid sequence that is from 45% to 75% identical to the amino acid sequence of HAC1268 (SEQ ID NO: 8) over a stretch of at least 250 amino acids.

In various embodiments, the enzyme has an amino acid sequence that is from 5% to 100% identical to the amino acid sequence of one or more of BstC (SEQ ID NO: 2), BstD (SEQ ID NO: 3), Δ20BstC* (SEQ ID NO: 15), Δ20BstC (SEQ ID NO: 18), BstE (SEQ ID NO: 4), BstE* (SEQ ID NO: 16), BstH (SEQ ID NO: 5), BstI (SEQ ID NO: 6), BstJ (SEQ ID NO: 7), BstM (SEQ ID NO: 9), or BstN (SEQ ID NO: 10).

In some embodiments, the amino acid sequence of the enzyme is less than 100% identical to the amino acid sequence of BstC (SEQ ID NO: 2), BstD (SEQ ID NO: 3), Δ20BstC (SEQ ID NO: 18), Δ20BstC* (SEQ ID NO: 15), BstE (SEQ ID NO: 4), BstE* (SEQ ID NO: 16), BstH (SEQ ID NO: 5), BstI (SEQ ID NO: 6), BstJ (SEQ ID NO: 7), BstM (SEQ ID NO: 9), or BstN (SEQ ID NO: 10).

In certain embodiments, the enzyme has no deletions or insertions compared to BstC (SEQ ID NO: 2), BstD (SEQ ID NO: 3), Δ20BstC (SEQ ID NO: 18), Δ20BstC* (SEQ ID NO: 15), BstE (SEQ ID NO: 4), BstE* (SEQ ID NO: 16), BstH (SEQ ID NO: 5), BstI (SEQ ID NO: 6), BstJ (SEQ ID NO: 7), BstM (SEQ ID NO: 9), or BstN (SEQ ID NO: 10).

In various embodiments, the difference between the amino acid sequence of the enzyme and the amino acid sequence of BstC (SEQ ID NO: 2), BstD (SEQ ID NO: 3), Δ20BstC (SEQ ID NO: 18), Δ20BstC* (SEQ ID NO: 15), BstE (SEQ ID NO: 4), BstE* (SEQ ID NO: 16), BstH (SEQ ID NO: 5), BstI (SEQ ID NO: 6), BstJ (SEQ ID NO: 7), BstM (SEQ ID NO: 9), or BstN (SEQ ID NO: 10) consists of one or more conservative amino acid substitutions.

In various embodiments, the difference between the amino acid sequence of the enzyme and the amino acid sequence of BstC (SEQ ID NO: 2), BstD (SEQ ID NO: 3), Δ20BstC (SEQ ID NO: 18), Δ20BstC* (SEQ ID NO: 15), BstE (SEQ ID NO: 4), BstE* (SEQ ID NO: 16), BstH (SEQ ID NO: 5), BstI (SEQ ID NO: 6), BstJ (SEQ ID NO: 7), BstM (SEQ ID NO: 9), or BstN (SEQ ID NO: 10) consists of one or more conservative amino acid substitutions.

In some embodiments, the enzyme has an amino acid sequence that is from 5% to 100%, 10% to 90%, 20% to 80%, 30% to 70%, 40% to 60'%©, 5% to 75%, 5% to 50%, 5% to 25%, 10% to 75%, 10% to 50%, 15% to 25%, 15% to 75%, 15% to 50%, 15% to 25%, 25% to 50%, 50% to 75%, or 75% to 100% identical to a naturally occurring enzyme. In certain embodiments, the enzyme has an amino acid sequence that is at least about 5%, 10%, 15%, or 20% but less than about 30%, 35%, 40%, or 45% identical to a naturally occurring enzyme. In various embodiments, the enzyme has an amino acid sequence that is at least about 45%, 50%, or 55% but less than about 65%, 70%, or 75% identical to a naturally occurring enzyme.

In some embodiments, the naturally occurring enzyme is a bacterial GT80 family sialyltransferase. The GT80 family is described in Audry, M., et al. (2011). Glycobiology 21, 716-726, the entire content of which is incorporated herein by reference.

In certain embodiments, the bacterial GT80 family sialyltransferase has the GT-B structural fold. The GT-B structural fold is described in Audry, M., et al. (2011). Glycobiology 21, 716-726, the entire content of which is incorporated herein by reference.

In various embodiments, the naturally occurring enzyme is produced by a microbial organism, e.g., in nature. In some embodiments, the microbial organism is a bacterium that is naturally present in the gastrointestinal tract of a mammal. In certain embodiments, the microbial organism is a bacterium within the genus *Photobacterium, Avibacterium, Shewanella, Bibersteinia, Haemophilus, Alistepes, Actinobacillus*, or *Helicobacter*.

In various embodiments, the enzyme has a mutation (e.g., 1, 2, 3, 4, 5, or more mutations, such as substitution mutations) compared to a naturally occurring α(2,3) sialyltransferase.

In some embodiments, when the amino acid sequences of the enzyme and BstE* are aligned, then the enzyme has a mutation at the position that aligns with position 13 of the amino acid sequence of BstE* (SEQ ID NO: 16). Sequence alignments are run using a variety of publicly available software programs, including but not limited to CLC Main Workbench, version 8.0.

In certain embodiments, the enzyme has a non-conservative mutation at the position that aligns with position 13 of the amino acid sequence of BstE* (SEQ ID NO: 16). In various embodiments, the enzyme has a histidine or an alanine at the position that aligns with position 13 of the amino acid sequence of BstE* (SEQ ID NO: 16).

In various embodiments, when the amino acid sequences of the enzyme and BstE* are aligned, then the enzyme comprises a mutation at the position that aligns with position 130 of the amino acid sequence of BstE* (SEQ ID NO: 16).

In some embodiments, the enzyme has a non-conservative mutation at the position that aligns with position 130 of the amino acid sequence of BstE* (SEQ ID NO: 16). In certain embodiments, the enzyme has a histidine or an alanine at the position that aligns with position 130 of the amino acid sequence of BstE* (SEQ ID NO: 16).

In some embodiments, the enzyme has a non-conservative mutation at the position that aligns with position 122 of the amino acid sequence of Δ20BstC (SEQ ID NO: 18). In certain embodiments, the enzyme has an alanine, valine, leucine, methionine, or phenylalanine at the position that aligns with position 122 of the amino acid sequence of Δ20BstC (SEQ ID NO: 18).

In various embodiments, the mutation that renders the enzyme more α(2,6)-selective than the naturally occurring α(2,3) sialyltransferase.

In some embodiments, the enzyme is an α(2,6) sialyltransferase.

In some embodiments, the enzyme comprises an amino acid sequence of Δ20BstC* (SEQ ID NO: 15), Δ20BstC*2 (SEQ ID NO: 27), Δ20BstC*3 (SEQ ID NO: 28), A20BstC*4 (SEQ ID NO: 29), or Δ20BstC*2 (SEQ ID NO: 30).

In certain embodiments, the $C_\alpha$ root-mean-square deviation (RMSD) between the backbone of the enzyme and a naturally occurring sialyltransferase is less than 3 Å. In some embodiments, the naturally occurring sialyltransferase is Pst6-224 (SEQ ID NO: 1). The structure of Pst6-224 (SEQ ID NO: 1) has been solved, see, e.g., Crystal Structure of Vibrionaceae *Photobacterium* sp. JT-ISH-224 2,6-sialyltransferase in a Ternary Complex with Donor Product CMP and Accepter Substrate Lactose, Kakuta et al. (2008) Glycobiology 18 66-73, the entire content of which is incorporated herein by reference.

In various embodiments, the naturally occurring sialyltransferase is BstC, BstD, BstE, BstH, BstI, BstJ, BstM, or BstN, or a homologue thereof.

In some embodiments, the bacterium is in a culture medium. In certain embodiments, the bacterium is on culture plate or in a flask. In various embodiments, the bacterium is cultured in a biofermentor.

The methods of producing sialylated oligosaccharides disclosed herein may further include retrieving the sialylated oligosaccharide (e.g., sialyllactose) from the bacterium (e.g., from the cytoplasm of the bacterium by lysing the bacterium) or from a culture supernatant of the bacterium.

In certain embodiments, the sialylated oligosaccharide includes any one of, or any combination of 2, 3, 4, 5, 6, 7, or 8 of 3'-sialyllactose (3'-SL), 6'-sialyllactose (6'-SL), 3'-sialyl-3-fucosyllactose (3'-S3FL), sialyllacto-N-tetraose a (SLNT a), sialyllacto-N-tetraose b (SLNT b), disialyllacto-N-tetraose (DSLNT), sialyllacto-N-fucopentaose II (SLNFP II), and sialyllacto-N-tetraose c (SLNT c).

In various embodiments, the bacterium comprises an exogenous or endogenous lactose-utilizing α(1,3) fucosyltransferase enzyme, an exogenous or endogenous lactose-utilizing α(1,4) fucosyltransferase enzyme, an exogenous or endogenous β(1,3) galactosyltransferase enzyme, an exogenous or endogenous β(1,4) galactosyltransferase enzyme, an exogenous or endogenous β-1,3-N-acetylglucosaminyltransferase, or any combination thereof.

In certain embodiments, the bacterium comprises an elevated level of cytoplasmic lactose, uridine diphosphate N-acetylglucosamine (UDP-GlcNAc), and/or cytidine-5'-monophosphosialic acid (CMP-Neu5Ac) compared to a corresponding wild-type bacterium (e.g., when the bacterium is cultured in the presence of lactose). In non-limiting examples, the level of lactose, UDP-GlcNAc, and/or CMP-Neu5Ac is at least about 5%, 10%, 15%, 20%, 25%, 30%, 35%, 40%, 45%, 50%, 75%, 100%, 200%, 300%, 400%, or 500% greater in the cytoplasm of the bacterium than a corresponding wild-type bacterium (e.g., when the bacterium is cultured in the presence of lactose).

Various implementations comprise providing a bacterium that comprises an exogenous lactose-utilizing sialyltransferase gene, a deficient sialic acid catabolic pathway, a sialic acid synthetic capability, and a functional lactose permease gene; and culturing the bacterium in the presence of lactose. The sialylated oligosaccharide is then retrieved from the bacterium or from a culture supernatant of the bacterium. Specifically, a sialic acid synthetic capability comprises expressing exogenous CMP-Neu5Ac synthetase, an exogenous sialic acid synthase, and an exogenous UDP-GlcNAc-2-epimerase, or a functional variant or fragment thereof.

In some embodiments relating to methods for producing sialylated oligosaccharides, it is the bacterium may further comprises the capability for increased UDP-GlcNAc production. By "increased production capability" is meant that the host bacterium produces greater than 10%, 20%, 50%, 100%, 2-fold, 5-fold, 10-fold, or more of a product than the native, endogenous bacterium. Preferably, the bacterium over-expresses a positive endogenous regulator of UDP-GlcNAc synthesis. In some embodiments, the bacterium overexpresses the nagC gene of *E. coli*. In certain embodiments, the bacterium over-expresses the *E. coli* glmS (L-glutamine:D-fructose-6-phosphate aminotransferase) gene or mutations in glmS gene that result in a GlmS enzyme not subject to feedback inhibition by its glucosamine-6-phosphate product (see, e.g., Deng, M. D., Grund, A. D., Wassink, S. L., Peng, S. S., Nielsen, K. L., Huckins, B. D., and Burlingame, R. P. (2006). Directed evolution and characterization of *Escherichia coli* glucosamine synthase. Biochimie 88, 419-429, the entire content of which is incorporated herein by reference. In various embodiments, the bacterium over-expresses the *E. coli* glmY gene (a positive translational regulator of glmS). In some embodiments, the bacterium over-expresses the *E. coli* glmZ gene (another positive translational regulator of glmS: glmY and glmZ are described in Reichenbach et al *Nucleic Acids Res* 36, 2570-80 (2008)). In certain embodiments, the bacterium overexpresses any combination of these genes. In various embodiments, the bacterium over-expresses nagC and glmS. In some embodiments, the bacterium over-expresses nagC and glmY. In certain embodiments, the bacterium over-expresses nagC and glmZ. In some embodiments, the gene transcript or encoded gene product is expressed or produced 10%, 20%, 50%, 2-fold, 5-fold, 10-fold, or more than the level expressed or produced by the corresponding native, naturally-occurring, or endogenous gene. Also provided herein are corresponding methods and bacteria in which any homologue or functional variant or fragment of nagC, glmS, glmY or glmZ (or any combination thereof) is overexpressed. In various embodiments, *E. coli* nagC, glmS, glmY or glmZ (or any combination thereof) is exogenously expressed in a bacterium other than *E. coli.*

Other components of UDP-GlcNAc metabolism include: (GlcNAc-1-P) N-acetylglucosamine-1-phosphate; (GlcN-1-P) glucosamine-1-phosphate; (GlcN-6-P) glucosamine-6-phosphate; (GlcNAc-6-P) N-acetylglucosamine-6-phosphate; and (Fruc-6-P) Fructose-6-phosphate. In certain embodiments, bacteria comprising the characteristics described herein are cultured in the presence of lactose, and lacto-N-neotetraose is retrieved, either from the bacterium itself (i.e., by lysis) or from a culture supernatant of the bacterium.

In various embodiments, the bacterium contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway in *E. coli* is described herein. In the sialic acid catabolic pathway described herein, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded in the nanATEK-yhcH operon, and repressed by NanR (ecocyc.org/ECOLI). In some embodiments, a deficient sialic acid catabolic pathway is engineered in *E. coli* by way of a mutation in endogenous nanA (N-acetylneuraminate lyase) (e.g., GenBank Accession Number D00067.1 (GI:216588), incorporated herein by reference) and/or nanK (N-acetylmannosamine kinase) genes (e.g., GenBank Accession Number (amino acid) BAE77265.1 (GI:85676015), incorporated herein by reference), and/or nanE (N-acetyltnannosamine-6-phosphate epimerase, GI: 947745, incorporated herein by reference). In certain embodiments, the nanT (N-acetylneuraminate transporter) gene is also inactivated or mutated. Other intermediates of sialic acid metabolism include: (ManNAc-6-P) N-acetylmannosamine-6-phosphate; (GlcNAc-6-P) N-acetylglucosamine-6-phosphate; (GlcN-6-P) Glucosamine-6-phosphate; and (Fruc-6-P) Fructose-6-phosphate. In some embodiments, nanA is mutated. In various embodiments, nanA and nanK are mutated, while nanE remains functional. In some embodiments, nanA and nanE are mutated, while nanK has not been mutated, inactivated or deleted. In various embodiments, a mutation is one or more changes in the nucleic acid sequence coding the gene product of nanA, nanK, nanE, and/or nanT. For example, the mutation may be 1, 2, 5, 10, 25, 50 or 100 changes in the nucleic acid sequence. For example, the nanA, nanK, nanE, and/or nanT is mutated by a null mutation.

Null mutations as described herein encompass amino acid substitutions, additions, deletions, or insertions that either cause a loss of function of the enzyme (i.e., reduced or no activity) or loss of the enzyme (i.e., no gene product). By deleted is meant that the coding region is removed in whole or in part such that no gene product is produced. In various embodiments, a gene has been inactivated such that that the coding sequence thereof has been altered such that the resulting gene product is functionally inactive or encodes a gene product with less than 100%, 80%, 50%, or 20% of the activity of the native, naturally-occurring, endogenous gene product.

In various embodiments, the bacterium also comprises a sialic acid synthetic capability. In some embodiments, the bacterium is an *E. coli* bacterium. For example, the bacterium comprises a sialic acid synthetic capability through provision of an exogenous UDP-GlcNAc 2-epimerase (e.g., neuC of *Campylobacter jejuni*, GenBank AAK91727.1; GI:15193223, incorporated herein by reference) or equivalent (e.g. *E. coli* S88 neuC GenBank YP_002392936.1; GI: 218560023), a Neu5Ac synthase (e.g., neuB of *C. jejuni* AAK91726.1 GenBank GI:15193222, incorporated herein by reference) or equivalent, (e.g. *Flavobacterium limnosediminis* sialic acid synthase, GenBank GI:559220424), and/or a CMP-Neu5Ac synthetase (e.g., neuA of *C. jejuni* (GenBank AAK91728.1; GI:15193224, incorporated herein by reference) or equivalent, (e.g. *Vibrio brasiliensis* CMP-sialic acid synthase, GenBank GI: 493937153). Functional variants and fragments are also disclosed herein.

In some embodiments, the bacterium comprises an exogenous or endogenous N-acetylneuraminate synthase, an exogenous or endogenous UDP-N-acetylglucosamine 2-epimerase, an exogenous or endogenous N-acetylneuraminate cytidylyltransferase, or any combination thereof.

In certain embodiments, the bacterium includes an exogenous N-acetylneuraminate synthase, UDP-N-acetylglucosamine 2-epimerase, and N-acetylneuraminate cytidylyltransferase from *Campylobacter jejuni.*

In various embodiments, the bacterium includes a reduced level of β-galactosidase activity compared to a corresponding wild-type bacterium (e.g., when the bacterium is cultured in the presence of lactose). In aspects, the reduced level of β-galactosidase activity includes reduced expression of a β-galactosidase gene or reduced β-galactosidase enzymatic activity. In aspects, the reduced level is less than 10% the level of the corresponding wild-type bacterium when the bacterium is cultured in the presence of lactose.

In some embodiments, the bacterium includes a deleted or inactivated endogenous β-galactosidase gene. In certain embodiments, the bacterium includes a deleted or inactivated endogenous lacZ gene and/or a deleted or inactivated endogenous lacI gene.

In various embodiments, the bacterium includes an endogenous β-galactosidase gene, wherein at least a portion of a promoter of the endogenous β-galactosidase gene has been deleted.

In some embodiments, the bacterium includes an exogenous β-galactosidase enzyme with reduced enzymatic activity compared to an endogenous β-galactosidase enzyme in a corresponding wild-type bacterium. In certain embodiments, the exogenous β-galactosidase gene is expressed at a lower level than to an endogenous β-galactosidase gene in a corresponding wild-type bacterium.

In various embodiments, the bacterium has less than 1000, 900, 800, 700, 600, 500, 400, 300, 200, 100, 75, 50, 45, 40, 35, 30, 25, 20, 15, 14, 13, 12, 11, 10, 9, 8, 7, 6, 5, 4, 3, 2, or 1 units of β-galactosidase activity when cultured in the presence of lactose. In some embodiments, the bacterium comprises at least about 0.5, 0.75, 1, 1.25, 1.5, 1.75, 2, or 2.5 units of β-galactosidase activity, but less than about 1000, 900, 800, 700, 600, 500, 400, 300, 200, 100, 75, 50, 45, 40, 35, 30, 25, 20, 15, 14, 13, 12, 11, 10, 9, 8, 7, 6, 5, 4, or 3 units of β-galactosidase activity, when the bacterium is cultured in the presence of lactose.

In some embodiments, the bacterium has a lactose permease gene. In certain embodiments, the lactose permease gene comprises a lacY gene.

In an aspect, the bacterium has an inactivated adenosine-5'-triphosphate (ATP)-dependent intracellular protease. In aspects, the inactivated ATP-dependent intracellular protease has a null mutation in an ATP-dependent intracellular protease gene. In aspects, the null mutation is a deletion of an endogenous lon gene.

In aspects, the bacterium further includes an exogenous *E. coli* rcsA or *E. coli* rcsB gene.

In certain embodiments, the bacterium further includes a mutation in a thyA gene.

In various embodiments, the bacterium does not express a β-galactoside transacetylase. In some embodiments, a β-galactoside transacetylase gene has been inactivated (e.g., deleted) in the bacterium.

In certain embodiments, the bacterium has a lacA mutation.

In various embodiments, the bacterium accumulates intracellular lactose in the presence of exogenous lactose.

In some embodiments, the bacterium is a member of the *Bacillus, Pantoea, Lactobacillus, Lactococcus, Streptococcus, Proprionibacterium, Enterococcus, Bifidobacterium, Sporolactobacillus, Micromomospora, Micrococcus, Rhodococcus*, or *Pseudomonas* genus.

In certain embodiments, the bacterium is a *Bacillus licheniformis, Bacillus subtilis, Bacillus coagulans, Bacillus thermophilus, Bacillus laterosporus, Bacillus megaterium, Bacillus mycoides, Bacillus pumilus, Bacillus lentus, Bacillus cereus*, and *Bacillus circulans, Erwinia herbicola* (*Pantoea agglomerans*), *Citrobacter freundii, Pantoea citrea, Pectobacterium carotovorum, Xanthomonas campestris Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Streptococcus thermophiles, Proprionibacterium freudenreichii, Enterococcus faecium, Enterococcus thermophiles*), *Bifidobacterium longum, Bifidobacterium infantis, Bifidobacterium bifidum, Pseudomonas fluorescens*, or *Pseudomonas aeruginosa* bacterium. In aspects, the bacterium is an *Escherichia coli* (*E. coli*) bacterium.

In various embodiments, the *E. coli* bacterium is a GI724 strain bacterium.

In some embodiments, the bacterium has a lacIq promoter mutation. In certain embodiments, the bacterium has a lacPL8 promoter mutation.

In various embodiments, the bacterium has a nucleic acid construct including an isolated nucleic acid encoding the lactose-utilizing sialyltransferase enzyme.

In some embodiments, a chromosome of the bacterium has a nucleic acid construct having an isolated nucleic acid encoding the lactose-utilizing sialyltransferase enzyme.

In certain embodiments, the nucleic acid is operably linked to a heterologous control sequence that directs the production of the enzyme in the bacterium. In various embodiments, the heterologous control sequence comprises a bacterial promoter, a bacterial operator, a bacterial ribosome binding site, a bacterial transcriptional terminator, or a plasmid selectable marker.

In various embodiments, the bacterium has the genotype: PlacIq-lacY, Δ(lacI-lacZ), ΔlacA, ΔthyA::(0.8RBS lacZ+), ampC::(Ptrp M13g8 RBS-λcI+, CAT), ΔnanATE::scar.

In aspects, provided herein are nucleic acids encoding a mutant enzyme. In some embodiments, the mutant enzyme has amino acids in the sequence set forth as SEQ ID NO: 15, 16, 19, 20, 21, 22, 23, 24, 25, 26, 27, 28, 29, or 30.

Also provided herein is a lactose-utilizing sialyltransferase enzyme having amino acids in the sequence set forth as SEQ ID NO: 15, 16, 19, 20, 21, 22, 23, 24, 25, 26, 27, 28, 29, or 30.

Certain sialyltransferases described herein have significant advantages over other enzymes of this class. Preferred sialyltransferases, e.g., BstM and BstN, are lactose-utilizing and produce superior amounts of sialyllactose in production strains of bacteria, e.g., engineered *E. coli*. Not all enzymes in the sialyltransferase class utilize lactose. For example, BstD and BstJ were found not to utilize lactose. Thus, lactose-utilizing sialyltransferase enzymes are rare among enzymes in the sialyltransferase class.

Another advantage of preferred sialyltransferases described is that they have fewer side activities, i.e., produce fewer undesirable by-products. An example of such an undesirable by-product is the KDO-lactose side-product. KDO is a component of *E. coli* lipopolysaccharide (LPS, endotoxin), and LPS is a molecule that elicits a strong and often dangerous immune response in some mammals, and humans in particular. KDO is part of the core structure of LPS. KDO-lactose is made from a CMP-KDO nucleotide sugar precursor that is found naturally in all strains of *E. coli*. Due to a similarity of KDO to sialic acid, some sialyltransferases, e.g., Pst6-224, utilize CMP-KDO as a substrate and produce unacceptable levels of KDO-lactose as an undesired side reaction. Certain enzymes of the present invention (e.g., BstM, BstN, Δ20BstC*) produce less of this unwanted by-product as compared to others, e.g., Pst6-224. Thus, the methods described herein that include a heterologous gene (in the engineered *E. coli* production strain) that expresses these preferred enzymes lead to a reduced or negligible amount of KDO-lactose. Such a reduced amount facilitates purification of the final desired product, sialyllactose, and is associated with a better safety profile for human use.

In an aspect, provided herein is a composition comprising sialylated oligosaccharides and less than 5%, e.g., less than 4%, 3%, 2%, 1%, 0.9%, 0.8%, 0.7%, 0.6%, 0.5%, 0.4%, 0.3%, 0.2%, or less than 0.1%, KDO-lactose. In some embodiments, the composition is substantially pure. In some embodiments, the composition comprises sialyllactose.

The sialyllactose produced by Δ20BstC* was found to be comprised of 6'-SL and 3'-SL. Production of both of these human milk oligosaccharides in the course of a single biofermentation represents a significant advantage in terms of time and cost of production over two separate fermentations. In some situations, such as striving to develop infant formulae that better emulate human milk, producing mixtures of human milk oligosaccahides in a single production fermentation is advantageous from a cost perspective.

Thus, the production runs using constructs expressing the preferred enzymes and the final purified endproduct(s) produced from such runs are characterized by increased safety, increased purity (and ease of purification) as well as reduced cost compared to earlier-described approaches. A composition comprising a sialyllactose produced using the methods, constructs, production strains described herein contain at least 10%, 25%, 50%, 2-fold, 5-fold, 10-fold or less KDO-lactose compared to compositions produced by other methods, e.g., produced using constructs encoding Pst6-224 or a-(2→6)-sialyltransferase encoded by the gene from the *Photobacterium* sp. JT-ISH-224. The invention also encompasses methods and a composition comprising substantially pure sialyllactose with minimal or minor levels of KDO-lactose. For example, the composition contains less than 5%, 4%, 3%, 2%, 1%, or 0.5% (or less) KDO-lactose of the total mass of SL. For example, a mutation, e.g., Δ (deletion) mutation in a Bst gene, e.g., Δ20BstC*, leads to a reduction in KDO-lactose.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

BRIEF DESCRIPTION OF THE DRAWINGS

The patent or application file contains at least one drawing executed in color. Copies of this patent or patent application publication with color drawings) will be provided by the Office upon request and payment of the necessary fee.

FIG. 2 is a table presenting pairwise percent amino acid sequence identity comparison between the two α(2,6) sialyllactose (SL) probe sequences and the 8 identified ST candidates.

FIG. 14 is an image of the BLOSUM62 matrix.

FIG. 15 is a table showing chemical shift assignments of the two major components of Δ20BstC* synthesized sialyllactose. Orange lines indicate inter-residue correlations seen in both ROESY and HMBC experiments; blue lines indicate inter-residue correlations seen in HMBC only.

DETAILED DESCRIPTION OF THE INVENTION

Figure 1:
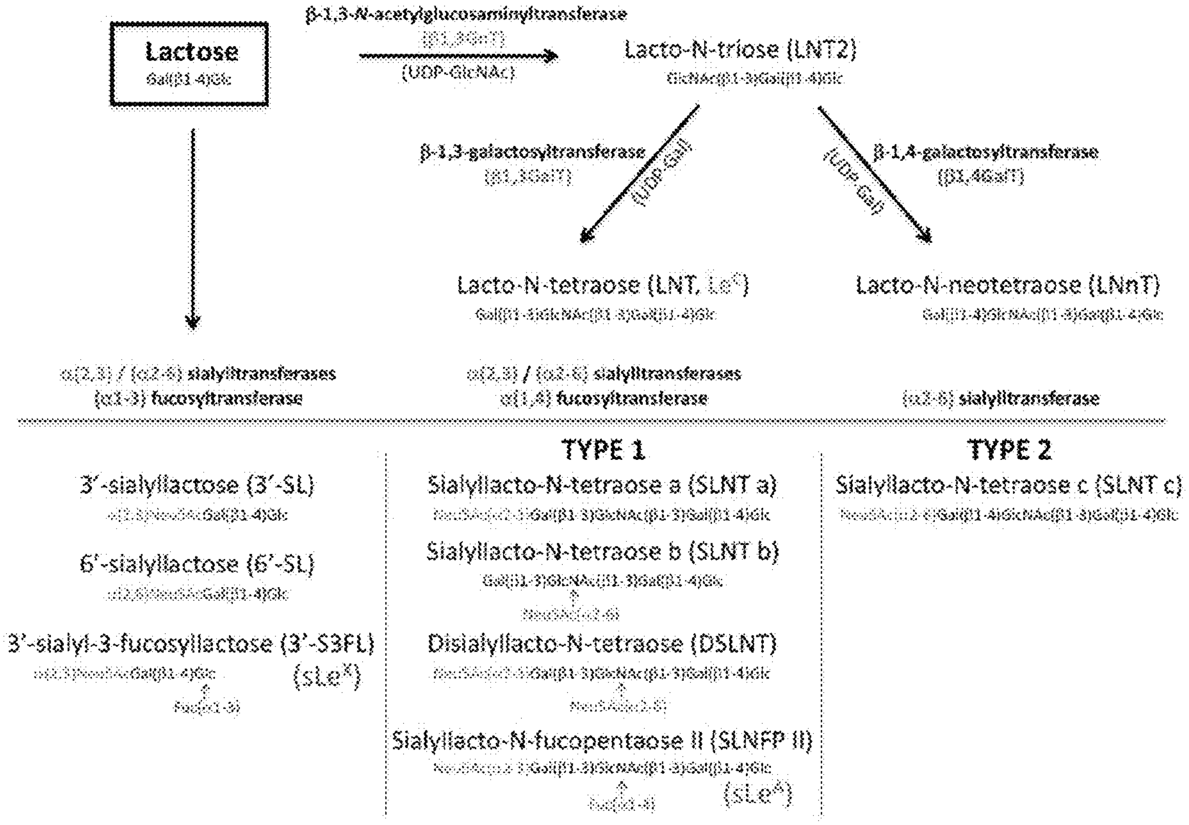
FIG. 1 is a schematic outlining the structures of the major sialyalated oligosaccharide species of human milk, how they are related to each other, and the steps necessary for their enzymatic synthesis from lactose.

The acidic oligosaccharides of human milk include a prominent sialyllactose (SL) fraction, comprising 3'-sialyllactose and 6'-sialyllactose (Bode, L., and Jantscher-Krenn, E. (2012). Adv Nutr 3, 383S-391S). Structurally, 3'-sialyllactose (3'-SL) consists of an N-acetylneuraminic acid (Neu5Ac) moiety joined through an α(2,3) linkage to the galactose portion of lactose (α(2,3)Neu5Ac Gal(β1-4)Glc), while 6'-sialyllactose (6'-SL) consists of a Neu5Ac moiety joined through an α(2,6) linkage to the galactose portion of lactose (α(2,6)Neu5Ac Gal (β1-4)Glc). 3'-SL and 6'-SL are two of the most abundant sialylated oligosaccharides present in human milk, together present at concentrations of up to ~0.5 Bao, Y., Zhu, L., and Newburg, D. S. (2007). Anal Biochem 370, 206-214).

The invention provides efficient and economical methods, cells, enzymes, and nucleic acids for producing sialylated oligosaccharides. The "lactose-utilizing sialyltransferase enzymes" disclosed herein include the amino acid sequences of the lactose-utilizing sialyltransferase enzyme, as well as variants and fragments thereof that exhibit sialyltransferase activity.

Prior to the methods described herein, the ability to produce purified acidic human milk oligosaccharides (hMOS) such as 3'-SL and 6'-SL inexpensively at large scale was problematic and inefficient. Purification of sialylated oligosaccharides from natural sources such as mammalian milks is not an economically viable approach, and production of hMOS through chemical synthesis is currently limited by stereo-specificity issues, precursor availability, product impurities, and high overall cost. As an alternative to chemical synthesis, bacteria can be metabolically engineered to produce hMOS. This approach involves the construction of microbial strains overexpressing heterologous glycosyltransferases, membrane transporters for the import of precursor sugars into the bacterial cytosol, and possessing enhanced pools of regenerating nucleotide sugars for use as biosynthetic precursors, e.g., as described by Dumon, C., et al. (2004). Biotechnol Prog 20, 412-19; Ruffing, A., and Chen, R. R. (2006). Microb Cell Fact 5, 25; Mao, Z., et al. (2006). Biotechnol Prog 22, 369-374).

A key aspect of this approach is the identification and use of a heterologous glycosyltransferase selected for overexpression in the microbial host. The choice of glycosyltransferase can significantly affect the final yield of the desired synthesized oligosaccharide, given that enzymes can vary greatly in terms of their kinetics, donor and acceptor substrate specificity, side reaction products, and enzyme stability and solubility. A few glycosyltransferases derived from different bacterial species have been identified and characterized in terms of their ability to catalyze the biosynthesis of hMOS in *E. coli* host strains [(Dumon, C., et al. (2006). Chembiochem 7, 359-365; Dumon, C., et al. (2004). Biotechnol Prog 20, 412-19; Li, M., et al. (2008). Biochemistry 47, 378-387; Li, M., et al. (2008). Biochemistry 47, 11590-97)].

However, there exists a growing need to identify and characterize additional glycosyltransferases that will be useful for the synthesis of hMOS in metabolically engineered bacterial hosts. The identification of additional glycosyltransferases with faster kinetics, greater affinity for nucleotide sugar donors and/or acceptor structures, or greater stability within the bacterial host has the potential to significantly improve the yields of therapeutically useful hMOS. To this end, candidate gene screening approach was undertaken to identify new α(2,3) and β(2,6) sialyltransferase genes encoding more efficient enzymes.

Lactose-Utilizing Sialyltransferase Enzymes 100911 In some embodiments, a lactose-utilizing sialyltransferase enzyme comprises 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100 or more mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity (e.g., enzymatic activity) of the naturally occurring protein.

Mutations include but are not limited to substitutions (such as conservative and non-conservative substitutions), insertions, and deletions. Non-limiting examples of lactose-utilizing sialyltransferase enzymes may have 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100, or more substitution mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity (e.g., enzymatic activity) of the naturally occurring protein.

Alternatively, the lactose-utilizing sialyltransferase enzyme is not a mutant (or the sequence altered) compared to a corresponding wild type sequence.

In various embodiments, a lactose-utilizing sialyltransferase enzyme may comprise a stretch of amino acids (e.g., the entire length of the lactose-utilizing sialyltransferase enzyme or a portion comprising at least about 50, 100, 200, 250, 300, 350, or 400 amino acids) in a sequence that is at least about 90%, 91%, 92%, 93%, 94%, 95%, 96%, 97%, 98%, 99%, 99.1%, 99.2%, 99.3%, 99.4%, or 99.5% identical to an amino acid sequence of a naturally occurring protein.

In some embodiments, the mutations are conservative, and the present subject matter includes many lactose-utilizing sialyltransferase enzymes in which the only mutations are substitution mutations. In non-limiting examples, a lactose-utilizing sialyltransferase enzyme has no deletions or insertions compared to a naturally occurring protein (e.g., a naturally occurring counterpart).

In certain embodiments, the lactose-utilizing sialyltransferase enzyme does not comprise a deletion or insertion compared to a naturally occurring lactose-utilizing sialyltransferase enzyme. Alternatively, a lactose-utilizing sialyltransferase enzyme may have (i) less than about 5, 4, 3, 2, or 1 inserted amino acids, and/or (ii) less than about 5, 4, 3, 2, or 1 deleted amino acids compared to a naturally occurring protein.

In various embodiments, a naturally occurring protein to which a lactose-utilizing sialyltransferase enzyme is compared or has been derived (e.g., by mutation, fusion, or other modification) is a microbial protein, e.g., a prokaryotic lactose-utilizing sialyltransferase enzyme such as a bacterial lactose-utilizing sialyltransferase enzyme. For example, the prokaryotic lactose-utilizing sialyltransferase enzyme is a mutant or variant of a natural (i.e., wild-type) bacterial protein.

In some embodiments, the microbial protein is produced by a Gram-positive bacterium or a Gram-negative bacterium.

In some embodiments, the lactose-utilizing sialyltransferase enzyme does not comprise a signal peptide. For example, the signal peptide (e.g., that is present in a naturally occurring counterpart) may be replaced with a methionine.

As used herein the term “signal peptide” refers to a short stretch of amino acids (e.g., 5-20 or 10-50 amino acids long) at the N-terminus of a protein that directs the transport of the protein. In various embodiments, the signal peptide is cleaved off during the post-translational modification of a protein by a cell. In instances where a signal peptide is not defined for a protein discussed herein, the signal peptide may optionally be considered to be, e.g., the first 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from the N-terminus of the translated protein (compared to a protein that has not had the signal peptide removed, e.g., compared to a naturally occurring protein).

With regard to a defined polypeptide, % identity values higher or lower than those provided herein will encompass various embodiments. Thus, where applicable, in light of a minimum % identity value, a lactose-utilizing sialyltransferase enzyme may comprise an amino acid sequence which is at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the reference SEQ ID NO or to each of the reference SEQ ID NOs. In embodiments, the lactose-utilizing sialyltransferase enzyme comprises an amino acid sequence that is 100% identical to the reference SEQ ID NO. Where applicable, in light of a maximum % identity to a reference sequence, a lactose-utilizing sialyltransferase enzyme may comprise an amino acid sequence which is less than 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, or 30% identical to the reference SEQ ID NO or to each of the reference SEQ ID NOs. In certain embodiments, a polypeptide comprises amino acids in a sequence that is preferably at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45% and less than about 75%, 70%, 65%, 60%, 55%, 50%, 45%, 44%, 43%, 42%, 41%, 40%, 39%, 38%, 37%, 36%, 35%, 34%, 33%, 32%, 31%, or 30% identical to the reference SEQ ID NO or to each of the reference SEQ ID NOs. In certain embodiments, a polypeptide comprises amino acids in a sequence that is between about 5% and about 75%, about 6% and about 75%, about 7% and about 75%, about 8% and about 75%, about 9% and about 75%, about 10% and about 75%, 11% and about 75%, 12% and about 75%, 13% and about 75%, 14% and about 75%, 15% and about 75%, 16% and about 75%, 17% and about 75%, 18% and about 75%, 19% and about 75%, 20% and about 75%, 21% and about 75%, 22% and about 75%, 23% and about 75%, 24% and about 75%, 25% and about 75%, 26% and about 75%, 27% and about 75%, 28% and about 75%, 29% and about 75%, 30% and about 75%, about 5% and about 100%, about 5% and about 95%, about 5%, and about 85%, about 5% and about 75%, about 5% and about 70%, about 5% and about 65%, 60%, about 5% and about 55%, about 5% and about 50%, about 5% and about 45%, about 5% and about 44%, about 5% and about 43%, about 5% and about 42%, about 5% and about 41%, about 5% and about 40%, about 5% and about 39%, about 5% and about 38%, about 5% and about 37%, about 5% and about 36%, about 5% and about 35%, about 5% and about 34%, about 5% and about 33%, about 5% and about 32%, about 5% and about 31%, or about 5% and about 30% identical to the reference SEQ ID NO or to each of the reference SEQ NOs.

Non-limiting examples of reference lactose-utilizing sialyltransferase enzymes and amino acid sequences disclosed herein include:

(i) a lactose-utilizing sialyltransferase enzyme from *Photobacterium* sp. JT-ISH-224 referred to herein as "Pst6-224" (GenBank Accession No. BAF92026.1; SEQ ID NO: 1);

(ii) a lactose-utilizing sialyltransferase enzyme from *Avibacterium paragallinarum* referred to herein as "BstC" [National Center for Biotechnology Information (NCBI) Reference Sequence: WP_021724759.1; SEQ NO: 2];

(iii) a lactose-utilizing sialyltransferase enzyme from *Actinobacillus areae* referred to herein as "BstD" (NCBI Reference Sequence: WP_005625206.1; SEQ ID NO: 3);

(iv) a lactose-utilizing sialyltransferase enzyme from *Haemophilus ducreyi* referred to herein as "BstE" (GenBank Accession No. AAP95068.1; SEQ ID NO: 4);

(v) a lactose-utilizing sialyltransferase enzyme from *Alistipes* (multispecies) referred to herein as "BstH" (NCBI Reference Sequence: WP_018695526.1; SEQ ID NO: 5);

(vi) a lactose-utilizing sialyltransferase enzyme from *Bibersteinia trealosi* referred to herein as "BstI" (GenBank Accession No. AGH37861.1; SEQ ID NO: 6);

(vii) a lactose-utilizing sialyltransferase enzyme from *Shewanella piezotolerans* referred to herein as "BstJ" (NCBI Reference Sequence Nos: YP_ 02314261.1 and WP_ 020915003.1; SEQ ID NO: 7);

(viii) a lactose-utilizing sialyltransferase enzyme from *Helicobacter acinonychis* referred to herein as "HAC1268" (GenBank Accession No. CAK00018.1; SEQ ID NO: 8);

(ix) a lactose-utilizing sialyltransferase enzyme from *Helicobacter pylori* referred to herein as "BstM" (NCBI Reference Sequence: WP_ 000743106.1; SEQ ID NO: 9); and (x) a lactose-utilizing sialyltransferase enzyme from *Helicobacter cetorum* referred to herein as "BstN" (NCBI Reference Sequence: WP_ 014661583.1; SEQ ID NO: 10).

In some embodiments, the lactose-utilizing sialyltransferase enzyme comprises an amino acid sequence with at least 15, 16, 17, 18, 19, 20, 21, 22, 23, 24, 25, 26, 28, 29, 30, 31, 32, 33, 34, 35, 36, 37, 38, 39, 40, 41, 42, 43, 44, 45, 46, 47, 48, 49, 50, 60, 70, 80, 90, or 100% identity to 1, 2, 3, 4, 5, 9, 10 or more lactose-utilizing sialyltransferase enzymes disclosed herein.

In embodiments, the amino acid sequence of a protein comprises no more than 1, 2, 3, 4, 5, 6, 7, 8, 9, 10, 15, 20, 25, 30, 35, 40, 45, or 50 mutations compared to its naturally occurring counterpart. In some embodiments, less than 50, 45, 40, 35, 30, 25, 20, 15, 10, 9, 8, 7, 6, 5, 4, 3, or 2 of the mutations is a deletion or insertion of 1, 2, 3, 4, or 5 or no more than 1, 2, 4, or 5 amino acids. In some embodiments, 1, 2, 3, 4, 5, 6, 7, 8, 9, 10, 15, 20, 25, 30, 35, 40, 45, 50 or more of the mutations is a substitution mutation. In certain embodiments, every mutation to a protein compared to its naturally occurring counterpart is a substitution mutation. In various embodiments, 1, 2, 3, 4, 5, 6, 7, 8, 9, 10, 15, 20, 25, 30, 35, 40, 45, 50 or more or all of the mutations to a protein compared to its naturally occurring counterpart is a conservative substitution mutation.

In various embodiments, a polypeptide does not have any insertion or deletion compared to its natural counterpart, other than (optionally) the removal of the signal peptide and/or the fusion of compounds such as another polypeptide at the N-terminus or C-terminus thereof.

In various embodiments, the $C_\alpha$ root-mean-square deviation (RMSD) between the backbone of the lactose-utilizing sialyltransferase enzyme and Pst6-224 (SEQ ID NO: 1), BstC (SEQ ID NO: 2), BstD (SEQ ID NO: 3), Δ20BstC (SEQ ID NO: 1), Δ20BstC* (SEQ ID NO: 15), BstE (SEQ ID NO: 4), BstE* (SEQ ID NO: 16), BstH (SEQ ID NO: 5), BstI (SEQ ID NO: 6), BstJ (SEQ ID NO: 7), HAC1268 (SEQ ID NO: 8), BstM (SEQ ID NO: 9), BstN (SEQ ID NO: 10), or PdST (SEQ ID NO: 13) is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. Non-limiting considerations relating to the sequence and structural differences between homologous proteins are discussed in Chothia and Lesk (1986) The EMBO Journal, 5(4):823-826, the entire content of which is incorporated herein by reference.

Also provided are functional fragments of the genes or gene products described herein. A fragment of a protein is characterized by a length (number of amino acids) that is less than the length of the full length mature form of the protein. A fragment, in the case of these sequences and all others provided herein, may be a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350, 350 to 400 amino acids, or 400 to 425 amino acids. The fragments encompassed in the present subject matter comprise fragments that retain functional fragments. As such, the fragments preferably retain the domains that are required or are important for sialyltransferase activity. Fragments can be determined or generated and tested for sialyltransferase activity using standard methods known in the art. For example, the encoded protein can be expressed by any recombinant technology known in the art and the sialyltransferase activity of the protein can be determined.

As used herein a "biologically active" fragment is a portion of a polypeptide which maintains one or more activities of a full-length reference polypeptide. Biologically active fragments as used herein exclude the full-length polypeptide. Biologically active fragments can be any size as long as they maintain the defined activity. Preferably, the biologically active fragment maintains at least 10%, at least 50%, at least 75% or at least 90%, of the activity (such as sialyltransferase activity) of the full length protein, Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired activity and/or specificity.

Mutant (altered) peptides (compared to a wild type counterpart) can be prepared using any technique known in the art. For example, a polynucleotide defined herein can be subjected to in vitro mutagenesis or DNA shuffling techniques. Products derived from mutated/altered DNA can readily be screened using techniques described herein to determine if they possess, for example, sialyltransferase activity.

Amino acid sequence deletions generally range from about 1 to 15 residues, e.g. about 1 to 10 residues and often about 1 to 5 contiguous residues. In some embodiments, a mutated or modified protein does not comprise any deletions or insertions. In various embodiments, a mutated or modified protein has less than about 10, 9, 8, 7, 5, 4, 3, or 2 deleted or inserted amino acids.

Substitution mutants have at least one amino acid residue in the polypeptide molecule removed and a different residue inserted in its place. Sites may be substituted in a relatively conservative manner in order to maintain activity and/or specificity. Such conservative substitutions are shown in the table below under the heading of "exemplary substitutions."

In certain embodiments, a mutant/variant polypeptide has only, or not more than, one or two or three or four conservative amino acid changes when compared to a naturally occurring polypeptide. Details of conservative amino acid changes are provided in the table below. As the skilled person would be aware, such minor changes can reasonably be predicted not to alter the activity of the polypeptide when expressed in a recombinant cell.

Exemplary Substitutions

| Original Residue | Example Substitutions |
|---|---|
| Alanine (Ala) | Val; Leu; Ile; Gly |
| Arginine (Arg) | Lys |
| Asparagine (Asn) | Gln; His |
| Cysteine (Cys) | Ser |
| Glutamine (Gln) | Asn; His |
| Glutamic Acid (Glu) | Asp |
| Glycine (Gly) | Pro; Ala |
| Histidine (His) | Asn; Gln |
| Isoleucine (Ile) | Leu; Val; Ala |
| Leucine (Leu) | Ile; Val; Met; Ala; Phe |
| Lysine (Lys) | Arg |
| Methionine (Met) | Leu; Phe |
| Phenylalanine (Phe) | Leu; Val; Ala |
| Proline (Pro) | Gly |
| Serine (Ser) | Thr |
| Threonine (Thr) | Ser |
| Tryptophan (Trp) | Tyr |
| Tyrosine (Tyr) | Trp; Phe |
| Valine (Val) | Ile; Leu; Met; Phe; Ala |

Mutations can be introduced into a nucleic acid sequence such that the encoded amino acid sequence is altered by, e.g., standard techniques, such as site-directed mutagenesis and PCR-mediated mutagenesis. In various embodiments, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. In some embodiments, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity/specificity of the protein can be determined. An increase, decrease, or elimination of a given biological activity of the variants disclosed herein can be readily measured by the ordinary person skilled in the art, i.e., by measuring the capability for binding a ligand and/or signal transduction.

In various embodiments, substitutions with natural amino acids are characterized using a BLOcks SUbstitution Matrix (a BLOSUM matrix). A non-limiting example of a BLOSUM matrix is the BLOSUM62 matrix, which is described in Styczynski et al. (2008) "BLOSUM62 miscalculations improve search performance" Nat Biotech 26 (3): 274-275, the entire content of which is incorporated herein by reference. The BLOSUM62 matrix is shown in FIG. 14.

Substitutions scoring at least 4 on the BLOSUM62 matrix are referred to herein as "Class I substitutions"; substitutions scoring 3 on the BLOSUM62 matrix are referred to herein as "Class II substitutions"; substitutions scoring 2 or 1 on the BLOSUM62 matrix are referred to herein as "Class III substitutions"; substitutions scoring 0 or −1 on the BLOSUM62 matrix are referred to herein as "Class IV substitutions"; substitutions scoring −2, −3, or −4 on the BLOSUM62 matrix are referred to herein as "Class V substitutions."

Various embodiments of the subject application include lactose-utilizing sialyltransferase enzymes having 1, 3, 4, 5, 6, 7, 8, 9, 10, 11, 12, 13, 14, 15, 16, 17, 18, 19, 20, 21, 23, 24, 25 or more Class I, II, III, IV, or V substitutions compared to a naturally occurring lactose-utilizing sialyltransferase enzyme (such as a lactose-utilizing sialyltransferase enzyme mentioned herein), or any 1, 2, 3, 4, 5, 6, 7, 8, 9, 10, 11, 12, 13, 14, 15, 16, 17, 18, 19, 20, 21, 22, 23, 24, 25 or more of any combination of Class I, II, III, IV, and/or V substitutions compared to a naturally occurring lactose-utilizing sialyltransferase enzyme such as a lactose-utilizing sialyltransferase enzyme exemplified herein.

Depending on context, a "conservative amino acid substitution" may refer to a mutation or to a difference between two sequences. For example, in some embodiments, a mutant comprises a conservative amino acid substitution compared to a naturally occurring protein, wherein the substitution was introduced into the mutant intentionally (e.g., by human-directed genetic modification) to produce a protein that is derived from the naturally occurring protein. In another example, one naturally occurring protein comprises a conservative amino acid substitution compared to another naturally occurring protein, in which case the "substitution" is a conservative difference between the two sequences at a given position when the sequences of each protein are aligned.

In some embodiments, the lactose-utilizing sialyltransferase enzyme of the present disclosure is more α(2,6)-selective than the naturally occurring α(2,3) sialyltransferase. As used herein, an "α(2,6)-selective" enzyme effects transfer of sialic acid at a ratio of α(2,6):α(2,3) of at least 1:1, such as from about 1.2:1 to about 100:1, e.g., 1.2:1 to 50:1, 2:1 to 50:1, 3:1 to 50:1, 4:1 to 50:1, 1.2:1 to 40:1, 1.2:1 to 30:1, 1.2:1 to 20:1, 1.2:1 to 10:1, 2:1 to 10:1, 1.3:1 to 10:1, or about 5:1 to about 10:1.

Production Methods

A variety of bacterial species may be used in the oligosaccharide biosynthesis methods provided herein, e.g., *E. coli, Erwinia herbicola* (*Pantoea agglomerans*), *Citrobacter freundii, Pantoea citrea, Pectobacterium carotovorum*, or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentils, Bacillus cereus*, and *Bacillus circulans*. Similarly, bacteria of the genera *Lactobacillus* and *Lactococcus* may be modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii*, and *Lactococcus lactis. Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum, Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). In various embodiments, bacteria comprising the characteristics described herein are cultured in the presence of lactose, and a sialylated oligosaccharide is retrieved, either from the bacterium itself or from a culture supernatant of the bacterium. In some embodiments, the sialylated oligosaccharide is purified for use in therapeutic or nutritional products, or the bacteria are used directly in such products. In certain embodiments, a suitable production host bacterial strain is one that is not the same bacterial strain as the source bacterial strain from which the lactose-utilizing sialyltransferase enzyme-encoding nucleic acid sequence was identified.

The bacterium utilized in the production methods described herein is genetically engineered to increase the efficiency and yield of sialylated oligosaccharide products. In various embodiments, the host production bacterium is characterized as having a reduced level of β-galactosidase activity, an ability to produce more UDP-GlcNAc or UDP-GlcNAc at a faster rate compared to a corresponding wild-type bacterium, an ability to produce more CMP-Neu5Ac or CMP-Neu5Ac at a faster rate compared to a corresponding wild-type bacterium, a defective or reduced sialic acid degradation pathway, an inactivated β-galactoside transacetylase gene, a lactose permease gene, or a combination thereof.

In some embodiments, the bacterium comprises an ability to produce more UDP-GlcNAc or UDP-GlcNAc at a faster rate compared to a corresponding wild-type bacterium.

The nucleotide sugar uridine diphosphate N-acetylglucosamine (UDP-GlcNAc) is a key metabolic intermediate in bacteria, where it is involved in the synthesis and maintenance of the cell envelope. In all known bacterial classes, UDP-GlcNAc is used to make peptidoglycan (murein); a polymer comprising the bacterial cell wall whose structural integrity is absolutely essential for growth and survival. In addition, grain-negative bacteria use UDP-GlcNAc for the synthesis of lipid A, an important component of the outer cell membrane. Thus, for bacteria, the ability to maintain an adequate intracellular pool of UDP-GlcNAc is critical.

The UDP-GlcNAc pool in *E. coli* is produced through the combined action of three glm genes, glmS (L-glutamine:D-fructose-6-phosphate aminotransferase), glmM (phosphoglucosamine mutase), and the bifunctional glmU (fused N-acetyl glucosamine-1-phosphate uridyltransferase and glucosamine-1-phosphate acetyl transferase) (FIG. 2). These three genes direct a steady flow of carbon to UDP-GlcNAc, a flow that originates with fructose-6-phosphate (an abundant molecule of central energy metabolism). Expression of the glm genes is under positive control by the transcriptional activator protein, NagC. When *E. coli* encounters glucosamine or N-acetyl-glucosamine in its environment, these molecules are each transported into the cell via specific membrane transport proteins and are used either to supplement the flow of carbon to the UDP-GlcNAc pool, or alternatively they are consumed to generate energy, under the action of nag operon gene products (i.e. nagA [N-acetyl-glucosamine-6-phosphate deacetylase] and nagB [glucosamine-6-phosphate deaminase]). In contrast to the glm genes, expression of nagA and nagB are under negative transcriptional control, but by the same regulatory protein as the glm genes, i.e. NagC. NagC is thus bi-functional, able to activate UDP-GlcNAc synthesis, while at the same time repressing the degradation of glucosamine-6-phosphate and N-acetylglucosamine-6-phosphate. The binding of NagC to specific regulatory DNA sequences (operators), whether such binding results in gene activation or repression, is sensitive to fluctuations in the cytoplasmic level of the small-molecule inducer and metabolite, GlcNAc-6-phosphate. Intracellular concentrations of GlcNAc-6-phosphate increase when N-acetylglucosamine is available as a carbon source in the environment, and thus under these conditions the expression of the glm genes (essential to maintain the vital UDP-GlcNAc pool) would decrease, unless a compensatory mechanism is brought into play. *E. coli* maintains a baseline level of UDP-GlcNAc synthesis through continuous expression of nagC directed by two constitutive promoters, located within the upstream nagA gene. This constitutive level of nagC expression is supplemented approximately threefold under conditions where the degradative nag operon is induced, and by this means *E. coli* ensures an adequate level of glm gene expression under all conditions, even when N-acetylglucosamine is being utilized as a carbon source. Many hMOS incorporate GlcNAc into their structures directly, and many also incorporate sialic acid, a sugar whose synthesis involves consumption of UDP-GlcNAc. Thus, synthesis of many types of hMOS in engineered *E. coli* carries the significant risk of reduced product yield and compromised cell viability resulting from depletion of the bacterium's UDP-GlcNAc pool. One way to address this problem during engineered synthesis of GlcNAc- or sialic acid-containing hMOS is to boost the UDP-GlcNAc pool through simultaneous over-expression of nagC, or preferably by simultaneous over-expression of both nagC and glmS.

In some embodiments relating to *E. coli* or a bacterium other than *E. coli*, the bacterium preferably comprises increased production of UDP-GlcNAc. As noted hereinabove, an exemplary means to achieve this is by over-expression of a positive endogenous regulator of UDP-GlcNAc synthesis, for example, overexpression of the nagC gene of *E. coli*. In certain embodiments, this nagC over-expression is achieved by providing additional copies of the nagC gene on a plasmid vector or by integrating additional nagC gene copies into the host cell chromosome. In various embodiments, over-expression is achieved by modulating the strength of the ribosome binding sequence directing nagC translation or by modulating the strength of the promoter directing nagC transcription. In some embodiments, the intracellular UDP-GlcNAc pool may be enhanced by other means, for example by over-expressing the *E. coli* glmS (L-glutamine:D-fructose-6-phosphate aminotransferase) gene, or alternatively by over-expressing the *E. coli* glmY gene (a positive translational regulator of glmS), or alternatively by over-expressing the *E. coli* glmZ gene (another positive translational regulator of glmS), or alternatively by simultaneously using a combination of approaches. In various embodiments, for example, the nagC (GenBank Protein Accession BAA35319.1, incorporated herein by reference) and glmS (GenBank Protein Accession NP_418185.1, incorporated herein by reference) genes which encode the sequences provided herein are overexpressed simultaneously in the same host cell in order to increase the intracellular pool of UDP-GlcNAc.

In certain embodiments, the ability to produce more CMP-Neu5Ac or CMP-Neu5Ac at a faster rate compared to a corresponding wild-type bacterium comprises the expression of any one of, or any combination of, or all three of an N-acetylneuraminate synthase, a UDP-N-acetylglucosamine 2-epimerase, and a N-acetylneuraminate cytidylyltransferase. Non limiting examples of these enzymes include NeuB, NeuC, and NeuA from *Campylobacter jejuni* (such as *Campyobacter jejuni* ATCC43484). In some embodiments, neuBCA genes are co-expressed in an operon.

In various embodiments, the defective or reduced sialic acid degradation pathway comprises the inactivation or deletion of any one of, any combination of, or each of a nanR gene, a nanA gene, a nanT gene, a nanE gene, or a nanK gene. In some embodiments the nanA, nanT, and nanE genes are inactivated or deleted in the bacterium.

As used herein, an "inactivated" or "inactivation of a" gene, encoded gene product (i.e., polypeptide), or pathway refers to reducing or eliminating the expression (i.e., transcription or translation), protein level (i.e., translation, rate of degradation), or enzymatic activity of the gene, gene product, or pathway. In the instance where a pathway is inactivated, preferably one enzyme or polypeptide in the pathway exhibits reduced or negligible activity. In some embodiments, the enzyme in the pathway is altered, deleted or mutated such that the product of the pathway is produced at low levels compared to a wild-type bacterium or an intact pathway. In certain embodiments, the product of the pathway is not produced. In various embodiments, the level of a compound that is utilized (e.g., used as a substrate, altered, catalyzed, or otherwise reduced or consumed) by the pathway is increased. In some embodiments, inactivation of a gene is achieved by deletion or mutation of the gene or regulatory elements of the gene such that the gene is no longer transcribed or translated. In certain embodiments, inactivation of a polypeptide can be achieved by deletion or mutation of the gene that encodes the gene product or mutation of the polypeptide to disrupt its activity. Inactivating mutations include additions, deletions or substitutions of one or more nucleotides or amino acids of a nucleic acid or amino acid sequence that results in the reduction or elimination of the expression or activity of the gene or polypeptide. In various embodiments, inactivation of a polypeptide is achieved through the addition of exogenous sequences (e.g., tags) to the N or C-terminus of the polypeptide such that the activity of the polypeptide is reduced or eliminated (e.g., by steric hindrance).

A host bacterium suitable for the production systems described herein exhibits an enhanced or increased cytoplasmic or intracellular pool of lactose and/or UDP-GlcNAc and/or CMP-Neu5Ac. In some embodiments, the bacterium is *E. coli* and endogenous *E. coli* metabolic pathways and genes are manipulated in ways that result in the generation of increased cytoplasmic concentrations of lactose and/or UDP-GlcNAc and/or CMP-Neu5Ac, as compared to levels found in wild type *E. coli*. Preferably, the bacterium accumulates an increased intracellular lactose pool and an increased intracellular UDP-GlcNAc and/or CMP-Neu5Ac pool. For example, the bacteria contain at least 10%, 20%, 50%, or 2×, 5×, 10× or more of the levels of intracellular lactose and/or intracellular UDP-GlcNAc and/or CMP-Neu5Ac compared to a corresponding wild type bacterium that lacks the genetic modifications described herein.

In certain embodiments, increased intracellular concentration of lactose in the host bacterium compared to wild-type bacterium is achieved by manipulation of genes and pathways involved in lactose import, export and catabolism. In non-limiting examples, described herein are methods of increasing intracellular lactose levels in *E. coli* genetically engineered to produce a human milk oligosaccharide by simultaneous deletion of the endogenous β-galactosidase gene (lacZ) and the lactose operon repressor gene (lacI). During construction of this deletion, the lacIq promoter is placed immediately upstream of (contiguous with) the lactose permease gene, lacY, i.e., the sequence of the lacIq promoter is directly upstream and adjacent to the start of the sequence encoding the lacY gene, such that the lacY gene is under transcriptional regulation by the lacIq promoter. The modified strain maintains its ability to transport lactose from the culture medium (via LacY), but is deleted for the wild-type chromosomal copy of the lacZ (encoding β-galactosidase) gene responsible for lactose catabolism. Thus, an intracellular lactose pool is created when the modified strain is cultured in the presence of exogenous lactose.

In some embodiments, increasing the intracellular concentration of lactose in *E. coli* involves inactivation of a β-galactoside transacetylase gene such as the lacA gene. With respect to an *E. coli* bacterium, an inactivating mutation, null mutation, or deletion of lacA prevents the formation of intracellular acetyl-lactose, which not only removes this molecule as a contaminant from subsequent purifications, but also eliminates *E.coli*'s ability to export excess lactose from its cytoplasm (Danchin A. Cells need safety valves. Bioessays 2009, July; 31(7):769-73.), thus greatly facilitating purposeful manipulations of the *E. coli* intracellular lactose pool.

In certain embodiments, a functional lactose permease gene is present in the bacterium. In various embodiments, the lactose permease gene is an endogenous lactose permease gene or an exogenous lactose permease gene. For example, the lactose permease gene may comprises an *E. coli* lacY gene (e.g., GenBank Accession Number V00295 (GI:41897), incorporated herein by reference). Many bacteria possess the inherent ability to transport lactose from the growth medium into the cell, by utilizing a transport protein that is either a homolog of the *E. coli* lactose permease (e.g., as found in *Bacillus licheniformis*), or a transporter that is a member of the ubiquitous PTS sugar transport family (e.g., as found in *Lactobacillus casei* and *Lactobacillus rhanmosus*). For bacteria lacking an inherent ability to transport extracellular lactose into the cell cytoplasm, this ability may be conferred by an exogenous lactose transporter gene (e.g., *E. coli* lacY) provided on recombinant DNA constructs, and supplied either on a plasmid expression vector or as exogenous genes integrated into the host chromosome.

As described herein, in some embodiments, the host bacterium preferably has a reduced level of β-galactosidase activity. In the embodiment in which the bacterium is characterized by the deletion of the endogenous β-galactosidase gene, an exogenous β-galactosidase gene may be introduced to the bacterium. For example, a plasmid expressing an exogenous β-galactosidase gene may be introduced to the bacterium, or recombined or integrated into the host genome. For example, the exogenous β-galactosidase gene may be inserted into a gene that is inactivated in the host bacterium, such as the lon gene.

In some embodiments, the exogenous β-galactosidase gene is a functional β-galactosidase gene characterized by a reduced or low level of β-galactosidase activity compared to β-galactosidase activity in wild-type bacteria lacking any genetic manipulation. Exemplary β-galactosidase genes include *E. coli* lacZ and β-galactosidase genes from any of a number of other organisms (e.g., the lac4 gene of *Kluyveromyces lactis* (GenBank Accession Number M84410 (GI:173304), incorporated herein by reference) that catalyzes the hydrolysis of β-galactosides into monosaccharides. The level of β-galactosidase activity in wild-type *E. coli* bacteria is, for example, 1,000 units (e.g., when the bacterium is cultured in the presence of lactose). Thus, the reduced β-galactosidase activity level encompassed by engineered host bacterium of the present invention includes less than 1,000 units, less than 900 units, less than 800 units, less than 700 units, less than 600 units, less than 500 units, less than 400 units, less than 300 units, less than 200 units, less than 100 units, or less than 50 units (e.g., when the bacterium is cultured in the presence of lactose). In some embodiments, low, functional levels of β-galactosidase include β-galactosidase activity levels of between 0.05 and 1,000 units, e.g., between 0.05 and 750 units, between 0.05 and 500 units, between 0.05 and 400 units, between 0.05 and 300 units, between 0.05 and 200 units, between 0.05 and 100 units, between 0.05 and 50 units, between 0.05 and 10 units, between 0.05 and 5 units, between 0.05 and 4 units, between 0.05 and 3 units, or between 0.05 and 2 units of β-galactosidase activity (e.g., when the bacterium is cultured in the presence of lactose). In certain embodiments, low, functional levels of β-galactosidase include β-galactosidase activity levels of between 1 and 1,000 units, e.g., between 1 and 750 units, between 1 and 500 units, between 1 and 400 units, between 1 and 300 units, between 1 and 200 units, between 1 and 100 units, between 1 and 50 units, between 1 and 10 units, between 1 and 5 units, between 1 and 4 units, between 1 and 3 units, or between 1 and 2 units of β-galactosidase activity (e.g., when the bacterium is cultured in the presence of lactose). For unit definition and assays for determining β-galactosidase activity, see Miller J H, Laboratory CSH. Experiments in molecular genetics. Cold Spring Harbor Laboratory Cold Spring Harbor, N.Y.; 1972; (incorporated herein by reference). This low level of cytoplasmic β-galactosidase activity is not high enough to significantly diminish the intracellular lactose pool. The low level of β-galactosidase activity is very useful for the facile removal of undesired residual lactose at the end of fermentations.

Optionally, the bacterium has an inactivated thyA gene. In various embodiments, a mutation in a thyA gene in the host bacterium allows for the maintenance of plasmids that carry thyA as a selectable marker gene. Exemplary alternative selectable markers include antibiotic resistance genes such as BLA (beta-lactamase), or proBA genes (to complement a proAB host strain proline auxotropy) or purA (to complement a purA host strain adenine auxotrophy).

In some embodiments purified oligosaccharide, e.g., 3'-SL, 6'-SL, 3'-S3FL, SLNT a, SLNT b, DSLNT, SLNFP II, or SLNT c is one that is at least 85%, 90%, 95%, 98%, 99%, or 100% (w/w) of the desired oligosaccharide by weight. Purity may be assessed by any known method, e.g., thin layer chromatography or other chromatographic techniques known in the art. Included herein is a method of purifying a sialylated oligosaccharide produced by a genetically engineered bacterium described herein, which method comprises separating the desired sialylated oligosaccharide from contaminants in a bacterial cell lysate or bacterial cell culture supernatant of the bacterium. In some embodiments, a sialylated oligosaccharide may be added to a food or beverage composition to increase the level of the sialylated oligosaccharide in the composition. In some examples, the sialylated oligosaccharide is added to dried or powder milk or milk product, e.g., infant formula. In some embodiments, it is added to a liquid milk. In other embodiments, it is added to a non-milk dairy product, e.g. yogurt or kefir. In various embodiments, a composition provided herein is not milk. In certain embodiments, a composition provided herein does not comprise milk.

In various embodiments, sialylated oligosaccharides are purified and used in a number of products for consumption by humans as well as animals, such as companion animals (dogs, cats) as well as livestock (bovine, equine, ovine, caprine, or porcine animals, as well as poultry). For example, a food, beverage, dietary supplement, or pharmaceutical composition may comprise a purified 3'-SL, 6'-SL, 3'-S3FL, SLNT a, SLNT b, DSLNT, SLNFP II, or SLNT c. In some embodiments, the composition comprises an excipient that is suitable for oral administration.

In certain embodiments, a method of producing a pharmaceutical composition comprising a purified human milk oligosaccharide (HMOS) (such as a sialylated oligosaccharide present in human milk) may be carried out by culturing a bacterium described herein, purifying the HMOS produced by the bacterium, and combining the HMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease.

Included herein are methods of treating, preventing, or reducing the risk of infection in a subject comprising administering to said subject a composition comprising a purified recombinant human milk oligosaccharide, wherein the HMOS binds to a pathogen and wherein the subject is infected with or at risk of infection with the pathogen. In some embodiments, the infection is caused by a Norwalk-like virus or *Campylobacter jejuni*. In certain embodiments, the subject is a mammal. In various embodiments, the mammal is, e.g., any mammal, e.g., a human, a primate, a mouse, a rat, a dog, a cat, a cow, a horse, or a pig. In some embodiments, the mammal is a human. In certain embodiments, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. In various embodiments, the purified HMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations to enhance the growth of beneficial microorganisms either in vitro or in vivo.

Included herein is a nucleic acid construct or an expression vector (such as a viral vector or a plasmid) comprising a nucleic acid encoding at least one lactose-utilizing sialyltransferase enzyme or a variant or fragment thereof, as described herein. The vector can further include one or more regulatory elements, e.g., a heterologous promoter. By "heterologous" is meant that the control sequence and protein-encoding sequence originate from different sources. For example, the sources may be different bacterial strains or species. The regulatory elements can be operably linked to a gene encoding a protein, a gene construct encoding a fusion protein gene, or a series of genes linked in an operon in order to express the fusion protein, Also provided herein is an isolated recombinant cell, e.g., a bacterial cell containing an aforementioned nucleic acid molecule or vector. The nucleic acid is optionally integrated into the genome of the host bacterium. In some embodiments, the nucleic acid construct also further comprises one or more enzymes that are not lactose-utilizing sialyltransferase enzymes.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically include plasmids. Expression vectors of the present invention include any vectors that function (i.e., direct gene expression) in host cells of the present invention, including in one of the prokaryotic or eukaryotic cells described herein, e.g., gram-positive, gram-negative, pathogenic, non-pathogenic, commensal, cocci, bacillus, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art.

A "heterologous promoter" is a promoter which is different from the promoter to which a gene or nucleic acid sequence is operably linked in nature.

The term "overexpress" or "overexpression" refers to a situation in which more factor is expressed by a genetically-altered cell than would be, under the same conditions, by a wild-type cell. Similarly, if an unaltered cell does not express a factor that it is genetically altered to produce, the term "express" (as distinguished from "overexpress") is used indicating the wild type cell did not express the factor at all prior to genetic manipulation.

A polypeptide or class of polypeptides may be defined by the extent of identity (% identity) of its amino acid sequence to a reference amino acid sequence, or by having a greater % identity to one reference amino acid sequence than to another. A variant of any of genes or gene products disclosed herein may have, e.g., 50%, 55%, 60%, 65%, 70%, 75%, 80%, 85%, 90%, 95%, 96%, 97%, 98%, or 99% sequence identity to the nucleic acid or amino acid sequences described herein. The term "% identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using a sequence comparison algorithm or by visual inspection. For example, % identity is relative to the entire length of the coding regions of the sequences being compared, or the length of a particular fragment or functional domain thereof. Variants as disclosed herein also include homologs, orthologs, or paralogs of the genes or gene products described herein. In some embodiments, variants may demonstrate a percentage of homology or identity, for example, at least about 50%, 55%, 60%, 65%, 70%, 75%, 80%, 85%, 90%, 95%, 96%, 97%, 98%, or 99% identity conserved domains important for biological function, e.g., in a functional domain, e.g. a catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST. For the BLAST searches, the following parameters are employed: (1) Expect threshold is 10; (2) Gap cost is Existence: 11 and Extension: 1; (3) The Matrix employed is BLOSUM62; (4) The filter for low complexity regions is "on."

As used herein, the term "about" in the context of a numerical value or range means ±10% of the numerical value or range recited or claimed, unless the context requires a more limited range.

In the descriptions above and in the claims, phrases such as "at least one of or "one or more of may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes/nucleic acids or sequences/amino acids that flank it in its naturally-occurring state. Purified also defines a degree of sterility that is safe for administration to a human subject, e.g., lacking infectious or toxic agents.

Similarly, by "substantially pure" when referring to a nucleotide or polypeptide means one that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

In some embodiments, the term "substantially pure" or "substantially free" with respect to a particular composition means that the composition comprising the sialylated oligosaccharide contains less than 50%, less than 40%, less than 30%, less than 20%, less than 15%, less than 10%, less than 5%, or less than 1% by weight of other substances. In some embodiments, "substantially pure" or "substantially free of" refers to a substance free of other substances, including impurities. Impurities may, for example, include by-products, contaminants, degradation products, water, and solvents.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

"Subject" as used herein refers to any organism to which a sialylated oligosaccharide may be administered. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In preferred embodiments, the subject is a human individual less than 2 years of age, an elderly subject (e.g., 65 or more years of age), an immunocompromised subject (e.g., suffering from an autoimmune disorder, undergoing immunosuppressive therapy associated with transplantation, or a subject diagnosed with cancer and undergoing chemotherapy), a malnourished individual, an individual recovering from a dysbiosis (for example of the gut microbiota following treatment with antibiotics), or any individual that would benefit from establishment or re-establishment of a healthy gut microbiota.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

As used herein, the singular forms "a," "an," and "the" include the plural reference unless the context clearly dictates otherwise. Thus, for example, a reference to "a disease," "an oligonucleotide," or "a nucleic acid" is a reference to one or more such embodiments, and includes equivalents thereof known to those skilled in the art and so forth.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Unless required otherwise by context, the terms "polypeptide" and "protein" are used interchangeably.

Exemplary Sequences Disclosed Herein Include the Following:

(Pst6-224)

SEQ ID NO: 1

MKNFLLLTLILLTACNNSEENTQSIIKNDINKTIIDEEYVNLEPINQSNISFTKHSWVQTCG

TQQLLTEQNKESISLSVVAPRLDDDEKYCFDFNGVSNKGEKYITKVTLNVVAPSLEVYV

DHASLPTLQQLMDIIKSEEENPTAQRYIAWGRIVPTDEQMKELNITSFALINNHTPADLV

QEIVKQAQTKHRLNVKLSSNTAHSFDNLVPILKELNSFNNVTVTNIDLYDDGSAEYVNL

YNWRDTLNKTDNLKIGKDYLEDVINGINEDTSNTGTSSVYNWQKLYPANYHFLRKDYL

TLEPSHELRDYIGDSLKQMQWDGFKKFNSKQQELFLSIVNFDKQKLQNEYNSSNLPNF

VFTGTTVWAGNHEREYYAKQQINVINNAINESSPHYLGNSYDLFFKGHPGGGIINTLIMQ

NYPSMVDIPSKISFEVLMMTDMLPDAVAGIASSLYFTIPAEKIKFIVFTSTETITDRETALR

SPLNQVMIKLGIVKEENVLFWADLPNCETGVCIAY (BstC)

SEQ ID NO: 2

MRKIITFFSLFFSISAWCQKMEIYLDYASLPSLNMILNLVENKNNEKVERIIGFERFDFNKE

ILNSFSKERIEFSKVSILDIKERSDKLYLNIEKSDTPVDLIIHTNLDHSVRSLLSIFKTLSPLF

HKINIEKLYLVDDGSGNYVDLYQHRQENISAILIEAQKKLKDALENRETDTDKLHSLTRY

TWHKIFPTEYILLRPDYLDIDEKMQPLKHFLSDTIVSMDLSRFSHFSKNQKELFLKITHFD

QNIFNELNIGTKNKEYKTFIFTGTTTWEKDKKKRLNNAKLQTEILESFIKPNGKFYLGNDI

KIFFKGHPKGDDINDYIIRKTGAEKIPANIPFEVLMMTNSLPDYVGGIMSTVYFSLPPKNI

DKVVFLGSEKIKNENDAKSQTLSKLMLMLNVITPEQIFFEEMPNPINF (BstD)

SEQ ID NO: 3

MFKIKSYGKNPQLQAVDIYIDFATIPSLSYFLHFLKHKHDHQRLRLFSLARFEMPQTVIEQ

YEGIIQFSRNVEHNVEPLLEQLQTILSQEGKQFELHLHLNLFHSFEMFLNLSPTYTKYKEK

ISKIVLHLYDDGSEGVMKQYQLQKSSSLVQDLAATKASLVSLFENGEGSFSQIDLIRYVW

NAVLETRYYLLSDHFLLDEKLQPLKAELGHYQLLNLSTYQYLSSEDLLWLKQILKIDAE

LESLMQKLTAQPVYFFSGTTFLG (BstE)

SEQ ID NO: 4

MLIQQNLEIYLDYATIPSLACFMHFIQHKDDVDSIRLFGLARFDIPQSIIDRYPANHLFYHN

IDNRDLTAVLNQLADILAQENKRFQINLHLNLFHSIDLFFAIYPIYQQYQHKISTIQLQLYD

DGSEGIVTQHSLCKIADLEQLILQHKNVLLELLTKGTANVPNPTLLRYLWNNIIDSQFHLI

SDHFLQHPKLQPLKRLLKRYTILDFTCYPRFNAEQKQLLKEILHISNELENLLKLLKQHNT

FLFTGTTAFNLDQEKLDLLTQLHILLLNEHQNPHSTHYIGNNYLLLIKGHANSPALNHTL

ALHFPDAIFLPANIPFEIFAMLGFTPNKMGGFASTSYINYPTENINIILFFLISDQPSTRIKW

LDYEKQFGLMSLLAMQKINEDQAFMCTIHN (BstH)

SEQ ID NO: 5

MKRLFRLFLCLALLSGTAACSDDEVSQNLIVINGGEHFLSLDGLARAGKISVLAPAPWR

VTKAAGDTWFRLSATEGPAGYSEVELSLDENPGAARSAQLAFACGDARTFRLSQGALS

-continued

AGYDSPDYYFYVTFGTMPTLYAGIHLLSHDKPGYVTFYSRSKTFDPAEFPARAEVTTAAD

RTADATQAEMEAMAREMKRRILEINSADPTAVFGLYVDDLRCRIGYDWFVAQGIDSAR

VKVSMLSDGTGTYNNFYNYFGDAATAEQNWESYASEVEALDWNHGGRYPETRSLPEF

ESYTWPYYLSTRPDYRLVVQDGSLLESSCPFITEKLGEMEIESIQPYEMLSALPESSRKRF

YDMAGFDYDKFAALFDASPKKNLIIIGTSHADDASARLQRDYVARIMEQYGAQYDVFF

KPHPADTTSAGYETEFPGLTLLPGQMPFEIFVWSLIDRVDMIGGYPSTVFLTVPVDKVRFI

FAADAASLVRPLNILFRDATDVEWMQ (BstI)

SEQ ID NO: 6

MEFCKMATTQKICVYLDYATIPSLNYILHFAQHFEDQETIRLFGLSRFHIPESVIQRYPKG

VVQFYPNQEKDFSALLLALKNILIEVKQQQRKCEIELHLNLFHYQLLLLPFLSLYLDTQD

YCHLTLKFYDDGSEAISALQELALAPDLAAQIQFEKQQFDELVVKKSFKLSLLSRYFWG

KLFESEYIWFNQAILQKAELQILKQEISSSRQMDFAIYQQMSDEQKQLVLEILNIDLNKVA

YLKQLMENQPSFLFLGTTLFNITQETKTWLMQMHVDLIQQYCLPSGQFFNNKAGYLCF

YKGHPNEKEMNQMILSQFKNLIALPDDIPLEILLLLGVIPSKVGGFASSALFNFTPAQIENI

IFFTPRYFEKDNRLHATQYRLMQGLIELGYLDAEKSVTHFEIMQLLTKE (BstI)

SEQ ID NO: 7

MLVNNQSHNPKLICWQRHPVNDEALLQGINAASFVSIASLCQHAATLLAGHPHSHLITIYG

NTYWSKDLARLIRYLTRISGVEIKKLELIDDGSSEYQKMFYWQRLSSEEQTRDLATGLK

NLKSYLSGNDNKLLRLLTGHSNKLPRRLSSFMNWHQLFPTTYHMLRMDYLDKPELHQL

KQYLGNNAQQIRWNYIADNLFDDEQQSLFYQLLGISLAEQKQLRAGRQQLHDFMFIGV

DSSNASSKLQINVIADSRQESGIIPTITAKKMLFKGHPFANFNQTIVDAHQMGEMPAMIPF

ETLIMTGNLPQKVGGMASSLYFSLPNNYHIEYIVFSGSKKDLEQHALLQIMLYTKVISPE

RVYFSEQFKSC (HMC1268)

SEQ ID NO: 8

MGTIKKPLIIAGNGPSIKDLDYALFPKDFDVFRCNQFYFEDKYYLGREIKGVFFNPCVLSS

QMQTVQYLMDNGEYSIERFFCSVSTDRHDFDGDYQTILPVDGYLKAHYPFVCDTFSLFK

GHEEIIKHVKYHLKTYSKELSAGVLMLLSAVVLGYKEIYLVGIDFGASSWGHFYDESQS

QHFSNHMADCHNIYYDMLTICLCQKYAKLYALAPNSPLSHLLTLNPQAKYPFELLDKPI

GYTSDLIISSPLEEKLLEFKNIEEKLLEFKNIEEKLLEFKNIEEKLLEFKNIEEKLLEFKNIEE

KLLEFKNIEKLLEFKNIEEKLLEFKNIEEKLLEFKNIEEKLLEFKNIEEKLLEFKNIEEKLL

EFKNIEEKLLEFKNIEEKLLASRLNNILRKIKRKHILFFWGGGTVTPTLKVSFRWGAA (BstM)

SEQ ID NO: 9

MKKPLIIAGNGPSIKDLDYSLFPKDFEVFRCNQFYFEDKYYLGREIKGVFFNPCVLSSQM

QTAQYLMDNGEYSIERFFCSVSTDRHDFDGDYQTILPVEGYLKAHYPFVCDTFSLFKGH

EEILRHVKYHLKTYSKELSAGVLMLLSAVVLGYKEIYLVGIDFGASSWGHFYDESQSQH

FSNHMADCHNIYYDMFTICLCQKYAKLYALAPNSPLRHILALNPQAKYHFELLDKPIGY

TSDLIVSLPLEEKLLEFKNIEEKLLEFKNIEEKLLEFKNIEEKLLVNRLKNILRKIKRKILPF

WGGGGNTHLKVSFRWGVA (BstN)

SEQ ID NO: 10

MSEKIFSQVDEKNQKKPLIIGNGPSIKDLDYSLFPKDFDVFRCNQFYFEDKYYLGKEVK

GVFFNPCVFHNQMNTAKHLIDNNEYYIEQFFCSVSKEQHDFNGDYQTILSVDEYLRANY

-continued

PFVRDTFSLFGEHEEILNHVKYHLKTYSKELSAGVLMLLSAIVLGYKEIYLVGVDFGANS

WGHFYDDNQSQHFINHMADCHNIYYDMLTIYLCQKYAKLYALVPNSPLNHLLPLNLQA

NHVFELLDKPIGYTSDLIVSSPLEEKLLESKNIDERFSQNKSFKNYLQRLKDKFLQMIFRG

GGVITIPRVIFKGKFA (pG543) >pEC3'-(T7)bstN-neuBCA-thyA_(pG543)

SEQ ID NO: 11

TCGCGCGTTTCGGTGATGACGGTGAAAACCTCTGACACATGCAGCTCCCGGAGACGGTCACAGC

TTGTCTGTAAGCGGATGCCGGGAGCAGACAAGCCCGTCAGGGCGCGTCAGCGGGTGTTGGCGGG

TGTCGGGGCTGGCTTAACTATGCGGCATCAGAGCAGATTGTACTGAGAGTGCACCATATATGCG

GTGTGAAATACCGCACAGATGCGTAAGGAGAAAATACCGCATCAGGCGCCTCCTCAACCTGTAT

ATTCGTAAACCACGCCCAATGGGAGCTGTCTCAGGTTTGTTCCTGATTGGTTACGGCGCGTTTC

GCATCATTGTTGAGTTTTTCCGCCAGCCCGACGCGCAGTTTACCGGTGCCTGGGTGCAGTACAT

CAGCATGGGGCAAATTCTTTCCATCCCGATGATTGTCGCGGGTGTGATCATGATGGTCTGGGCA

TATCGTCGCAGCCCACAGCAACACGTTTCCTGAGGAACCATGAAACAGTATTTAGAACTGATGC

AAAAAGTGCTCGACGAAGGCACACAGAAAAACGACCGTACCGGAACCGGAACGCTTTCCATTTT

TGGTCATCAGATGCGTTTTAACCTGCAAGATGGATTCCCGCTGGTGACAACTAAACGTTGCCAC

CTGCGTTCCATCATCCATGAACTGCTGTGGTTTCTGCAGGGCGACACTAACATTGCTTATCTAC

ACGAAAACAATGTCACCATCTGGGACGAATGGGCCGATGAAAACGGCGACCTCGGGCCAGTGTA

TGGTAAACAGTGGCGCGCCTGGCCAACGCCAGATGGTCGTCATATTGACCAGATCACTACGGTA

CTGAACCAGCTGAAAAACGACCCGGATTCGCGCCGCATTATTGTTTCAGCGTGGAACGTAGGCG

AACTGGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACATTGCC

AGCTACGCGTTATTGGTGCATATGATGGCGCAGCAGTGCGATCTGGAAGTGGGTGATTTTGTCT

GGACCGGTGGCGACACGCATCTGTACAGCAACCATATGGATCAAACTCATCTGCAATTAAGCCG

CGAACCGCGTCCGCTGCCGAAGTTGATTATCAAACGTAAACCCGAATCCATCTTCGACTACCGT

TTCGAAGACTTTGAGATTGAAGGCTACGATCCGCATCCGGGCATTAAAGCGCCGGTGGCTATCT

AATTACGAAACATCCTGCCAGAGCCGACGCCAGTGTGCGTCGGTTTTTTTACCCTCCGTTAAAT

TCTTCGAGACGCCTTCCCGAAGGCGCCATTCGCCATTCAGGCTGCGCAACTGTTGGGAAGGGCG

ATCGGTGCGGGCCTCTTCGCTATTACGCCAGCTGGCGAAAGGGGGATGTGCTGCAAGGCGATTA

AGTTGGGTAACGCCAGGGTTTTCCCAGTCACGACGTTGTAAAACGACGGCCAGTGCCAAGCTTA

CTGCTCACAAGAAAAAAGGCACGTCATCTGACGTGCCTTTTTTATTTGTACTACCCTGTACGAT

TACTGCAGGTCGACTTATTTTTTCCATATCTGTTCAACCTTTTTTAAATCCTCCAAACAGTCAA

TATCTAAACTTGAGCTTTCGTCCATTAAAAAATGCTTGGTTTTGCTTTGTAAAAAGCTAGGATT

GTTTAAAAATTCTTTTATCTTTAAAATATAAATTGCACCATTGCTCATATAAGTTTAGGCAAT

TTTTGCCTTGGCATAAAAGGATATTCATCATTACAAATCCCTGCTAAATCGCCACAATCATTAC

AAACAAAGGCTTTTAGAATTTTATTATCACATTCGCTTACGCTAATTAGGGCATTTGCATTGCT

ATTTTTATAAAGATTAAAAGCTTCATTAATATGAATATTTGTTCTTAGCGGTGAAGTGGGTTGT

AAAAAAACTACATCTTCATAATCTTTATAAAATTTTAGAGCATGTAACAGCACTTTATCGCTTG

TGGTATCATCTTGTGCAAGGCTAATTGGGCGTTTTAAAATATCAACATTTTGACTTTTTGCATA

ATTTAAAATTTCATCACTATCACTGCTTACAACAACTTTACTAATGCTTTTAGCATTTAGTGCA

GCTTTGATCGTGTAGTAAATTAAAGGTTTATTGTTTAATAAAACCAAATTTTTATTTTTAATAC

-continued

CCTTTGAGCCACCACGAGCAGGGATTATTGCTAAGCTCATTTTATATCCTTAAAAACTTTTTGT

GTGCTGAGTTTAAAAAAATCTCCGCTTTGTAAATATTCAAAAAATAATTTTGAGCTATCTAAAA

TCTCTAACTAAGCGCTAAATAAATCTTGTTTTTTATGAATAGTGTTAATAGCTTTTAGTATTTC

ATCACTATTTGCATTAACTTTTAGTGTATTTTCATTGCCAAGTCTTCCATTTTGTCTTGAGCCA

ACTAAAATCCCTGCTGTTTTTAAGTATAAGGCCTCTTTTAAAATACAACTTGAATTACCTATTA

TAAAATCAGCATTTTTTAACAAAGTTATAAAATACTCAAATCTAAGCGATGGAAAAAGCTTAAA

TCTAGGGTTATTTTTAAACTCTTCATAGCTTTGCAAGATTAATTCAAAACCTAAATCATTATTT

GGATAAATAACAATATAATTTTTATTACTTTGTATCAGTGCTTTTACTAAATTGTCTGCTTGAT

TTTTAATGCTAGTAATTTCAGTTGTAACAGGATGAAACATAAGCAAAGCGTAGTTTTCATAATT

TATATCATAATATTTTTTTGCTTCGCTAAGTGAAATTTTATTATCGTTTAAAAGTTCTAAATCA

GGCGAACCTATGATAAAAATAGATTTTTCATCTTCTCCAAGCTGCATTAAACGCCTTTTTGCAA

ACTCATCATTTACTAAATGAATATGAGCTAGTTTTGATATAGCGTGGCGTAAGCTATCGTCAAT

AGTTCCTGAAATCTCTCCGCCTTCAATATGCGCTACTAAGATATTATTTAATGCTCCAACAATA

GCTGCTGCTAAAGGCTCAATTCTATCTCCATGTACTACGATTAAATCAGGTTTTAGCTCATTTG

CATACCTTGAAAATCCATCAATTGTAGTAGCTAAAGCCTTATCAGTTTGATAATATTTATCATA

ATTTATAAATTCATAAATATTTTTAAAGCCATTTTTATAAAGTTCTTTAACTGTATAGCCAAAA

TTTTTACTTAAGTGCATTCCTGTTGCAAAGATGTAAAGTTCAAATTCGCTTGAGTTTTGCACCC

TGTACATTAAAGATTTAATCTTAGAATAATCAGCCCTAGAGCCTGTTATAAAAAGGATTTTTTT

CACGCAAAATCCTCATAGCTTAACTGAGCATCATTTTCTATATCTCTTAATGCTTTTTTGCCTA

AAATATTTTCAAATTCAGCCGCACTAATTCCACCAAGTCCAGGTCTTTTAACCCAAATATTATC

CATAGATAAAACTTCGCCTTTTTTAATATCTTTAATGCTAACTACACTTGCAAAGGCAAAATCA

ATTGTAACTTGTTCTTGTTTAGCCGCTTTTTTACTTTCATTATTTCCTCTTATTATAGCCATTT

GCTCACTTTGTATAATTAGCTCTTTTAAAGCCTTTGTATCCATAGAACAAACTATATCAGGGCC

ACTTCTATGCATACTATCAGTAAAATGTCTTTCAAGCACACAAGCTCCAAGTACAACTGCACCT

AAACACGCAAGATTATCTGTTGTGTGGTCGCTTAAGCCTACCATACAAGAAAATTCTTTTTTTA

ACTCAAGCATAGCGTTTAATCTTACAAGATTATGCGGGGTTGGGTAAAGATTGGTCGTGTGCAT

TAAAACAAAAGGAATTTCATTGTCTAATAAGATTTTTACAGTTGGTTTTATACTTTCAATACTA

TTCATTCCTGTGCTAACTATCATAGGCTTTTTAAAGGCTGCTATGTGTTTAATAAGCGGATAAT

TATTACACTCACCTGAACCAATCTTAAAAGCACTAACTCCCATATCTTCTAAGCGGTTCGCACC

TGCACGAGAAAAAGGTGTGCTAAGATAAACAAGACCTAATTTTTCTGTGTATTCTTTAAGTGCT

AGCTCATCTTTATAATCCAAAGCACATTTTTGCATAATCTCATAAATGCTTATTTTTGCATTAC

CAGGAATTACTTTTTTAGCGGCCTTACTCATCTCATCTTCAACAATATGAGTTTGATGCTTTAT

AATCTTAGCACCTGCGCTAAAGGCTGCATCTACCATAATTTTAGCTAGTTCTAAACTGCCATTA

TGATTAATGCCTATTTCAGGTACGACTAAGGGTGCTTTTTCTTCACTTATGATTATATTTTGTA

TTTTTATTTCTTTCATTTATTTTCCTCCTTAGTCGACGGTACCCTTAAGCGAATTTTCCTTTAA

AGATCACGCGGGGAATTGTAATGACTCCACCCCCACGGAAGATCATTTGAAGAAACTTATCTTT

AAGACGTTGAAGATAGTTTTTGAAGGACTTATTCTGAGAGAAGCGCTCGTCGATGTTCTTCGAC

TCTAACAGTTTTTCTTCTAAAGGGGAGCTAACGATTAAATCCGACGTGTAGCCGATGGGCTTAT

CAAGCAGCTCAAATACATGGTTTGCCTGTAAGTTCAACGGTAAAAGATGGTTCAGAGGACTGTT

AGGTACTAAAGCATATAATTTGGCGTATTTTTGACAAAGGTAAATAGTCAACATGTCATAATAA

ATGTTATGGCAGTCAGCCATGTGGTTAATAAAGTGCTGACTCTGGTTGTCATCGTAAAAATGTC

-continued

CCCAGCTATTTGCGCCAAAATCGACACCGACTAAGTAGATTTCCTTGTATCCTAAAACAATTGC

GCTCAACAACATAAGGACCCCCGCAGATAATTCTTTTGAATATGTCTTCAGATGGTATTTGACA

TGGTTTAAGATTTCCTCATGCTCCCCAAACAAGCTAAAGGTGTCACGTACAAACGGGTAGTTTG

CACGAAGGTATTCGTCCACCGATAAGATGGTCTGGTAATCACCGTTAAAATCGTGTTGTTCTTT

CGACACACTACAAAAGAACTGCTCGATGTAGTATTCGTTGTTGTCAATTAAATGCTTCGCGGTA

TTCATTTGATTATGGAAGACGCACGGATTAAAGAATACACCTTTGACCTCTTTGCCCAAGTAAT

ACTTATCTTCGAAATAGAATTGGTTACAGCGGAAAACGTCGAAATCTTTTGGGAACAACGAATA

GTCAAGGTCTTTGATTGATGGTCCGTTGCCCGCGATAATCAAGGGCTTTTTTTGGTTCTTCTCG

TCAACCTGGCTGAAGATTTTTTCCGACATATGTATATCTCCTTCTTGAATTCTAACAATTGATT

GAATGTATGCAAATAAATGCATACACCATAGGTGTGGTTTAATTTGATGCCCTTTTTCAGGGCT

GGAATGTGTAAGAGCGGGGTTATTTATGCTGTTGTTTTTTTGTTACTCGGGAAGGGCTTTACCT

CTTCCGCATAAACGCTTCCATCAGCGTTTATAGTTAAAAAAATCTTTCGGAACTGGTTTTGCGC

TTACCCCAACCAACAGGGGATTTGCTGCTTTCCATTGAGCCTGTTTCTCTGCGCGACGTTCGCG

GCGGCGTGTTTGTGCATCCATCTGGATTCTCCTGTCAGTTAGCTTTGGTGGTGTGTGGCAGTTG

TAGTCCTGAACGAAAACCCCCCGCGATTGGCACATTGGCAGCTAATCCGGAATCGCACTTACGG

CCAATGCTTCGTTTCGTATCACACACCCCAAAGCCTTCTGCTTTGAATGCTGCCCTTCTTCAGG

GCTTAATTTTTAAGAGCGTCACCTTCATGGTGGTCAGTGCGTCCTGCTGATGTGCTCAGTATCA

CCGCCAGTGGTATTTATGTCAACACCGCCAGAGATAATTTATCACCGCAGATGGTTATCTGTAT

GTTTTTTATATGAATTTATTTTTTGCAGGGGGGCATTGTTTGGTAGGTGAGAGATCAATTCTGC

ATTAATGAATCGGCCAACGCGCGGGGAGAGGCGGTTTGCGTATTGGGCGCTCTTCCGCTGCTAG

CGGAGTGTATACTGGCTTACTATGTTGGCACTGATGAGGGTGTCAGTGAAGTGCTTCATGTGGC

AGGAGAAAAAAGGCTGCACCGGTGCGTCAGCAGAATATGTGATACAGGATATATTCCGCTTCCT

CGCTCACTGACTCGCTACGCTCGGTCGTTCGACTGCGGCGAGCGGAAATGGCTTACGAACGGGG

CGGAGATTTCCTGGAAGATGCCAGGAAGATACTTAACAGGGAAGTGAGAGGGCCGCGGCAAAGC

CGTTTTTCCATAGGCTCCGCCCCCCTGACAAGCATCACGAAATCTGACGCTCAAATCAGTGGTG

GCGAAACCCGACAGGACTATAAAGATACCAGGCGTTTCCCCCTGGCGGCTCCCTCGTGCGCTCT

CCTGTTCCTGCCTTTCGGTTTACCGGTGTCATTCCGCTGTTATGGCCGCGTTTGTCTCATTCCA

CGCCTGACACTCAGTTCCGGGTAGGCAGTTCGCTCCAAGCTGGACTGTATGCACGAACCCCCCG

TTCAGTCCGACCGCTGCGCCTTATCCGGTAACTATCGTCTTGAGTCCAACCCGGAAAGACATGC

AAAAGCACCACTGGCAGCAGCCACTGGTAATTGATTTAGAGGAGTTAGTCTTGAAGTCATGCGC

CGGTTAAGGCTAAACTGAAAGGACAAGTTTTGGTGACTGCGCTCCTCCAAGCCAGTTACCTCGG

TTCAAAGAGTTGGTAGCTCAGAGAACCTTCGAAAAACCGCCCTGCAAGGCGGTTTTTTCGTTTT

CAGAGCAAGAGATTACGCGCAGACCAAAACGATCTCAAGAAGATCATCTTATTAATCAGATAAA

ATATTTCTAGGCGGCCGCGAACGAAAACTCACGTTAAGGGATTTTGGTCATGAGATTATCAAAA

AGGATCTTCACCTAGATCCTTTTAAATTAAAAATGAAGTTTTAAATCAATCTAAAGTATATATG

AGTAAACTTGGTCTGACAGTTACCAATGCTTAATCAGTGAGGCACCTATCTCAGCGATCTGTCT

ATTTCGTTCATCCATAGTTGCCTGACTCCCCGTCGTGTAGATAACTACGATACGGGAGGGCTTA

CCATCTGGCCCCAGTGCTGCAATGATACCGCGAGACCCACGCTCACCGGCTCCAGATTTATCAG

CAATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCAAC

-continued

GTTGTTGCCATTGCTACAGGCATCGTGGTGTCACGCTCGTCGTTTGGTATGGCTTCATTCAGCT

CCGGTTCCCAACGATCAAGGCGAGTTACATGATCCCCCATGTTGTGCAAAAAAGCGGTTAGCTC

CTTCGGTCCTCCGATCGTTGTCAGAAGTAAGTTGGCCGCAGTGTTATCACTCATGGTTATGGCA

GCACTGCATAATTCTCTTACTGTCATGCCATCCGTAAGATGCTTTTCTGTGACTGGTGAGTACT

CAACCAAGTCATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACGTTCTTCGGGG

CGAAAACTCTCAAGGATCTTACCGCTGTTGAGATCCAGTTCGATGTAACCCACTCGTGCACCCA

ACTGATCTTCAGCATCTTTTACTTTCACCAGCGTTTCTGGGTGAGCAAAAACAGGAAGGCAAAA

TGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGA

AAAATAAACAAATAGGGGTTCCGCGCACATTTCCCCGAAAAGTGCCACCTGACGTCTAAGAAAC

CATTATTATCATGACATTAACCTATAAAAATAGGCGTATCACGAGGCCCTTTCGTC (pG549)pEC3'-(T7)bstM-neuBCAthyA

SEQ ID NO: 12

TCGCGCGTTTCGGTGATGACGGTGAAAACCTCTGACACATGCAGCTCCCGGAGACGGTCACAGC

TTGTCTGTAAGCGGATGCCGGGAGCAGACAAGCCCGTCAGGGCGCGTCAGCGGGTGTTGGCGGG

TGTCGGGGCTGGCTTAACTATGCGGCATCAGAGCAGATTGTACTGAGAGTGCACCATATATGCG

GTGTGAAATACCGCACAGATGCGTAAGGAGAAAATACCGCATCAGGCGCCTCCTCAACCTGTAT

ATTCGTAAACCACGCCCAATGGGAGCTGTCTCAGGTTTGTTCCTGATTGGTTACGGCGCGTTTC

GCATCATTGTTGAGTTTTTCCGCCAGCCCGACGCGCAGTTTACCGGTGCCTGGGTGCAGTACAT

CAGCATGGGGCAAATTCTTTCCATCCCGATGATTGTCGCGGGTGTGATCATGATGGTCTGGGCA

TATCGTCGCAGCCCACAGCAACACGTTTCCTGAGGAACCATGAAACAGTATTTAGAACTGATGC

AAAAAGTGCTCGACGAAGGCACACAGAAAAACGACCGTACCGGAACCGGAACGCTTTCCATTTT

TGGTCATCAGATGCGTTTTAACCTGCAAGATGGATTCCCGCTGGTGACAACTAAACGTTGCCAC

CTGCGTTCCATCATCCATGAACTGCTGTGGTTTCTGCAGGGCGACACTAACATTGCTTATCTAC

ACGAAAACAATGTCACCATCTGGGACGAATGGGCCGATGAAAACGGCGACCTCGGGCCAGTGTA

TGGTAAACAGTGGCGCGCCTGGCCAACGCCAGATGGTCGTCATATTGACCAGATCACTACGGTA

CTGAACCAGCTGAAAAACGACCCGGATTCGCGCCGCATTATTGTTTCAGCGTGGAACGTAGGCG

AACTGGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACATTGCC

AGCTACGCGTTATTGGTGCATATGATGGCGCAGCAGTGCGATCTGGAAGTGGGTGATTTTGTCT

GGACCGGTGGCGACACGCATCTGTACAGCAACCATATGGATCAAACTCATCTGCAATTAAGCCG

CGAACCGCGTCCGCTGCCGAAGTTGATTATCAAACGTAAACCCGAATCCATCTTCGACTACCGT

TTCGAAGACTTTGAGATTGAAGGCTACGATCCGCATCCGGGCATTAAAGCGCCGGTGGCTATCT

AATTACGAAACATCCTGCCAGAGCCGACGCCAGTGTGCGTCGGTTTTTTTACCCTCCGTTAAAT

TCTTCGAGACGCCTTCCCGAAGGCGCCATTCGCCATTCAGGCTGCGCAACTGTTGGGAAGGGCG

ATCGGTGCGGGCCTCTTCGCTATTACGCCAGCTGGCGAAAGGGGGATGTGCTGCAAGGCGATTA

AGTTGGGTAACGCCAGGGTTTTCCCAGTCACGACGTTGTAAAACGACGGCCAGTGCCAAGCTTA

CTGCTCACAAGAAAAAAGGCACGTCATCTGACGTGCCTTTTTTATTTGTACTACCCTGTACGAT

TACTGCAGGTCGACTTATTTTTTCCATATCTGTTCAACCTTTTTTAAATCCTCCAAACAGTCAA

TATCTAAACTTGAGCTTTCGTCCATTAAAAAATGCTTGGTTTTGCTTTGTAAAAAGCTAGGATT

GTTTAAAAATTCTTTTATCTTTAAAATATAAATTGCACCATTGCTCATATAAGTTTTAGGCAAT

-continued

TATCTAAACTTGAGCTTTCGTCCATTAAAAAATGCTTGGTTTTGCTTTGTAAAAAGCTAGGATT

GTTTAAAAATTCTTTTATCTTTAAAATATAAATTGCACCATTGCTCATATAAGTTTTAGGCAAT

TTTTGCCTTGGCATAAAAGGATATTCATCATTACAAATCCCTGCTAAATCGCCACAATCATTAC

AAACAAAGGCTTTTAGAATTTTATTATCACATTCGCTTACGCTAATTAGGGCATTTGCATTGCT

ATTTTTATAAAGATTAAAAGCTTCATTAATATGAATATTTGTTCTTAGCGGTGAAGTGGGTTGT

AAAAAAACTACATCTTCATAATCTTTATAAAATTTTAGAGCATGTAACAGCACTTTATCGCTTG

TGGTATCATCTTGTGCAAGGCTAATTGGGCGTTTTAAAATATCAACATTTTGACTTTTTGCATA

ATTTAAAATTTCATCACTATCACTGCTTACAACAACTTTACTAATGCTTTTAGCATTTAGTGCA

GCTTTGATCGTGTAGTAAATTAAAGGTTTATTGTTTAATAAAACCAAATTTTTATTTTTAATAC

CCTTTGAGCCACCACGAGCAGGGATTATTGCTAAGCTCATTTTATATCCTTAAAAACTTTTTGT

GTGCTGAGTTTAAAAAAATCTCCGCTTTGTAAATATTCAAAAAATAATTTTGAGCTATCTAAAA

TCTCTAACTTAGCGCTAAATAAATCTTGTTTTTTATGAATAGTGTTAATAGCTTTTAGTATTTC

ATCACTATTTGCATTAACTTTTAGTGTATTTTCATTGCCAAGTCTTCCATTTTGTCTTGAGCCA

ACTAAAATCCCTGCTGTTTTTAAGTATAAGGCCTCTTTTAAAATACAACTTGAATTACCTATTA

TAAAATCAGCATTTTTTAACAAAGTTATAAAATACTCAAATCTAAGCGATGGAAAAAGCTTAAA

TCTAGGGTTATTTTTAAACTCTTCATAGCTTTGCAAGATTAATTCAAAACCTAAATCATTATTT

GGATAAATAACAATATAATTTTTATTACTTTGTATCAGTGCTTTTACTAAATTGTCTGCTTGAT

TTTTAATGCTAGTAATTTCAGTTGTAACAGGATGAAACATAAGCAAAGCGTAGTTTTCATAATT

TATATCATAATATTTTTTTGCTTCGCTAAGTGAAATTTTATTATCGTTTAAAAGTTCTAAATCA

GGCGAACCTATGATAAAAATAGATTTTTCATCTTCTCCAAGCTGCATTAAACGCCTTTTTGCAA

ACTCATCATTTACTAAATGAATATGAGCTAGTTTTGATATAGCGTGGCGTAAGCTATCGTCAAT

AGTTCCTGAAATCTCTCCGCCTTCAATATGCGCTACTAAGATATTATTTAATGCTCCAACAATA

GCTGCTGCTAAAGGCTCAATTCTATCTCCATGTACTACGATTAAATCAGGTTTTAGCTCATTTG

CATACCTTGAAAATCCATCAATTGTAGTAGCTAAAGCCTTATCAGTTTGATAATATTTATCATA

ATTTATAAATTCATAAATATTTTTAAAGCCATTTTTATAAAGTTCTTTAACTGTATAGCCAAAA

TTTTTACTTAAGTGCATTCCTGTTGCAAAGATGTAAAGTTCAAATTCGCTTGAGTTTTGCACCC

TGTACATTAAAGATTTAATCTTAGAATAATCAGCCCTAGAGCCTGTTATAAAAAGGATTTTTTT

CACGCAAAATCCTCATAGCTTAACTGAGCATCATTTTCTATATCTCTTAATGCTTTTTTGCCTA

AAATATTTTCAAATTCAGCCGCACTAATTCCACCAAGTCCAGGTCTTTTAACCCAAATATTATC

CATAGATAAAACTTCGCCTTTTTTAATATCTTTAATGCTAACTACACTTGCAAAGGCAAAATCA

ATTGTAACTTGTTCTTGTTTAGCCGCTTTTTTACTTTCATTATTTCCTCTTATTATAGCCATTT

GCTCACTTTGTATAATTAGCTCTTTTAAAGCCTTTGTATCCATAGAACAAACTATATCAGGGCC

ACTTCTATGCATACTATCAGTAAAATGTCTTTCAAGCACACAAGCTCCAAGTACAACTGCACCT

AAACACGCAAGATTATCTGTTGTGTGGTCGCTTAAGCCTACCATACAAGAAAATTCTTTTTTTA

ACTCAAGCATAGCGTTTAATCTTACAAGATTATGCGGGGTTGGGTAAAGATTGGTCGTGTGCAT

TAAAACAAAAGGAATTTCATTGTCTAATAAGATTTTTACAGTTGGTTTTATACTTTCAATACTA

TTCATTCCTGTGCTAACTATCATAGGCTTTTTAAAGGCTGCTATGTGTTTAATAAGCGGATTAT

TATTACACTCACCTGAACCAATCTTAAAAGCACTAACTCCCATATCTTCTAAGCGGTTCGCACC

TGCACGAGAAAAAGGTGTGCTAAGATAAACAAGACCTAATTTTTCTGTGTATTCTTTAAGTGCT

AGCTCATCTTTATAATCCAAAGCACATTTTTGCATAATCTCATAAATGCTTATTTTTGCATTAC

-continued

CAGGAATTACTTTTTTAGCGGCCTTACTCATCTCATCTTCAACAATATGAGTTTGATGCTTTAT

AATCTTAGCACCTGCGCTAAAGGCTGCATCTACCATAATTTTAGCTAGTTCTAAACTGCCATTA

TGATTAATGCCTATTTCAGGTACGACTAAGGGTGCTTTTTCTTCACTTATGATTATATTTTGTA

TTTTTATTTCTTTCATTTATTTTCCTCCTTAGTCGACGGTACCCTTAAGCCACCCCCCAGCGGA

ACGACACTTTAAGATGCGTATTGCCGCCACCCCCCCAAAACGGCAGGATCTTACGTTTGATCTT

ACGCAGGATGTTCTTAAGACGATTCACAAGAAGCTTCTCTTCAATATTCTTGAACTCAAGCAAC

TTTTCCTCGATATTTTTGAACTCTAAAAGTTTCTCCTCGATGTTTTTAAATTCCAGAAGCTTCT

CCTCAAGGGGAAGCGATACAATCAGGTCACTTGTATAGCCGATCGGTTTATCAAGCAACTCGAA

GTGGTATTTTGCTTGCGGGTTCAGTGCCAGGATGTGACGAAGCGGAGAGTTCGGTGCTAAGGCG

TAAAGTTTTGCATACTTTTGACACAGGCAGATTGTGAACATGTCATAGTAAATGTTGTGGCAAT

CGGCCATGTGATTGCTGAAGTGCTGGGAATGACTCTCATCGTAGAAGTGGCCCCAGCTTGACGC

ACCAAAGTCAATCCCGACCAAGTAAATCTCCTTATACCCCAAAACCACGGCCGACAACAGCATT

AAGACTCCGGCACTCAATTCTTTACTATAAGTTTTTAAGTGGTACTTCACATGGCGAAGGATTT

CCTCATGGCCCTTAAAAAGGCTGAATGTGTCACAAACAAATGGGTAGTGGGCCTTCAAATAACC

CTCCACCGGAAGGATCGTCTGATAATCGCCGTCGAAGTCATGGCGGTCTGTCGAGACACTGCAG

AAGAAGCGTTCGATGGAATATTCACCGTTGTCCATCAGATATTGAGCTGTTTGCATTTGAGAAG

ATAACACACAGGGATTGAAGAATACGCCTTTAATCTCACGTCCAAGGTAATACTTATAATCGAA

ATAAAACTGATTACAGCGAAAGACTTCGAAATCCTTGGGAAATAAACTATAGTCCAGGTCTTTG

ATGGATGGCCCGTTCCCCGCAATAATTAAGGGTTTCTTCATATGTATATCTCCTTCTTGAATTC

TAACAATTGATTGAATGTATGCAAATAAATGCATACACCATAGGTGTGGTTTAATTTGATGCCC

TTTTTCAGGGCTGGAATGTGTAAGAGCGCCCTTATTTATGCTGTTGTTTTTTTGTTACTCGGGA

AGGGCTTTACCTCTTCCGCATAAACGCTTCCATCAGCGTTTATAGTTAAAAAAATCTTTCGGAA

CTGGTTTTGCGCTTACCCCAACCAACAGGGGATTTGCTGCTTTCCATTGAGCCTGTTTCTCTGC

GCGACGTTCGCGGCGGCGTGTTTGTGCATCCATCTGGATTCTCCTGTCAGTTAGCTTTGGTGGT

GTGTGGCAGTTGTAGTCCTGAACGAAAACCCCCCGCGATTGGCACATTGGCAGCTAATCCGGAA

TCGCACTTACGGCCAATGCTTCGTTTCGTATCACACACCCCAAAGCCTTCTGCTTTGAATGCTG

CCCTTCTTCAGGGCTTAATTTTTAAGAGCGTCACCTTCATGGTGGTCAGTGCGTCCTGCTGATG

TGCTCAGTATCACCGCCAGTGGTATTTATGTCAACACCGCCAGAGATAATTTATCACCGCAGAT

GGTTATCTGTATGTTTTTTATATGAATTTATTTTTTGCAGGGGGGCATTGTTTGGTAGGTGAGA

GATCAATTCTGCATTAATGAATCGGCCAACGCGCGGGGAGAGGCGGTTTGCGTATTGGGCGCTC

TTCCGCTGCTAGCGGAGTGTATACTGGCTTACTATGTTGGCACTGATGAGGGTGTCAGTGAAGT

GCTTCATGTGGCAGGAGAAAAAAGGCTGCACCGGTGCGTCAGCAGAATATGTGATACAGGATAT

ATTCCGCTTCCTCGCTCACTGACTCGCTACGCTCGGTCGTTCGACTGCGGCGAGCGGAAATGGC

TTACGAACGGGGCGGAGATTTCCTGGAAGATGCCAGGAAGATACTTAACAGGGAAGTGAGAGGG

CCGCGGCAAAGCCGTTTTTCCATAGGCTCCGCCCCCCTGACAAGCATCACGAAATCTGACGCTC

AAATCAGTGGTGGCGAAACCCGACAGGACTATAAAGATACCAGGCGTTTCCCCCTGGCGGCTCC

CTCGTGCGCTCTCCTGTTCCTGCCTTTCGGTTTACCGGTGTCATTCCGCTGTTATGGCCGCGTT

TGTCTCATTCCACGCCTGACACTCAGTTCCGGGTAGGCAGTTCGCTCCAAGCTGGACTGTATGC

ACGAACCCCCCGTTCAGTCCGACCGCTGCGCCTTATCCGGTAACTATCGTCTTGAGTCCAACCC

GGAAAGACATGCAAAAGCACCACTGGCAGCAGCCACTGGTAATTGATTTAGAGGAGTTAGTCTT

GAAGTCATGCGCCGGTTAAGGCTAAACTGAAAGGACAAGTTTTGGTGACTGCGCTCCTCCAAGC

-continued

CAGTTACCTCGGTTCAAAGAGTTGGTAGCTCAGAGAACCTTCGAAAAACCGCCCTGCAAGGCGG

TTTTTTCGTTTTCAGAGCAAGAGATTACGCGCAGACCAAAACGATCTCAAGAAGATCATCTTAT

TAATCAGATAAAATATTTCTAGGCGGCCGCGAACGAAAACTCACGTTAAGGGATTTTGGTCATG

AGATTATCAAAAAGGATCTTCACCTAGATCCTTTTAAATTAAAAATGAAGTTTTAAATCAATCT

AAAGTATATATGAGTAAACTTGGTCTGACAGTTACCAATGCTTAATCAGTGAGGCACCTATCTC

AGCGATCTGTCTATTTCGTTCATCCATAGTTGCCTGACTCCCCGTCGTGTAGATAACTACGATA

CGGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTAGTTCGCCAGTTAAT

AGTTTGCGCAACGTTGTTGCCATTGCTACAGGCATCGTGGTGTCACGCTCGTCGTTTGGTATGG

CTTCATTCAGCTCCGGTTCCCAACGATCAAGGCGAGTTACATGATCCCCCATGTTGTGCAAAAA

AGCGGTTAGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTTCTGTGA

CTGGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAAAA

CGTTCTTCGGGGCGAAAACTCTCAAGGATCTTACCGCTGTTGAGATCCAGTTCGATGTAACCCA

CTCGTGCACCCAACTGATCTTCAGCATCTTTTACTTTCACCAGCGTTTCTGGGTGAGCAAAAAC

AGGAAGGCAAAATGCCGCAAAAAAGGGAATAAGGGCGACACGGAAATGTTGAATACTCATACTC

TTCCTTTTTCAATATTATTGAAGCATTTATCAGGGTTATTGTCTCATGAGCGGATACATATTTG

AATGTATTTAGAAAAATAAACAAATAGGGGTTCCGCGCACATTTCCCCGAAAAGTGCCACCTGA

CGTCTAAGAAACCATTATTATCATGACATTAACCTATAAAAATAGGCGTATCACGAGGCCCTTT

CGTC (PdST)

SEQ ID NO: 13

MTIYLDhASLPTLNQLMHFTKESEDKETARIFGFSRFKLPEKITEQYNNIHFVEIKNNRPTE

DIFTILDQYPEKLELDLHLNIAHSIQLFHPILQYRFKHPDRISIKSLNLYDDGTaEYVDLEKE

ENKDIKSAIKKAEKQLSDYLLTGKINFDNPTLARYVWQSQYPVKYHFLSTEYFEKAEFL

QPLKTYLAGKYQKMDWSAYEKLSPEQQTFYLKLVGFSDETKQLFHTEQTKFIFTGTTT

WEGNTDIREYYAKQQLNLLKHFTHSEGDLFIGDQYKIYFKGHPRGGDINDYILKHAKDI

TNIPANISFEILMMTGLLPDKVGGVASSLYFSLPKEKISHIIFTSNKKIKNKEDALNDPYVR

VMLRLGMIDKSQIIFWDSLKQL (PdST*)

SEQ ID NO: 14

MTIYLDhASLPTLNQLMHFTKESEDKETARIFGFSRFKLPEKITEQYNNIHFVEIKNNRPTE

DIFTILDQYPEKLELDLHLNIAHSIQLFHPILQYRFKHPDRISIKSLNLYDDGTaEYVDLEKE

ENKDIKSAIKKAEKQLSDYLLTGKINFDNPTLARYVWQSQYPVKYHFLSTEYFEKAEFL

QPLKTYLAGKYQKMDWSAYEKLSPEQQTFYLKLVGFSDETKQLFHTEQTKFIFTGTTT

WEGNTDIREYYAKQQLNLLKHFTHSEGDLFIGDQYKIYFKGHPRGGDINDYILKHAKDI

TNIPANISFEILMMTGLLPDKVGGVASSLYFSLPKEKISHIIFTSNKKIKNKEDALNDPYVR

VMLRLGMIDKSQIIFWDSLKQL

-continued (Δ20BstC*)

SEQ ID NO: 15

MEIYLDHASLPSLNMILNLVENKNNEKVERIIGFERFDFNKEILNSFSKERIEFSKVSILDIK

EFSDKLYLNIEKSDTPVDLIIHTNLDHSVRSLLSIFKTLSPLFHKINIEKLYLYDDGSFNYV

DLYQHRQENISAILIEAQKKLKDALENRETDTDKLHSLTRYTWHKIFPTEYILLRPDYLDI

DEKMQPLKEIFLSDTIVSMDLSRFSHFSKNQKELFLKITHFDQNIFNELNIGTKNKEYKTFI

FTGTTTWEKDKKKRLNNAKLQTEILESFIKPNGKFYLGNDIKIFFKGHPKGDDINDYIIRK

TGAEKIPANIPFEVLMMTNSLPDYVGGIMSTVYFSLPPKNIDKVVFLGSEKIKNENDAKS

QTLSKLMLMLNVITPEQIFFEEMPNPINF (BstE*)

SEQ ID NO: 16

MLIQQNLEIYLDYATIPSLACFMHFIQHKDDVDSIRLFGLARFDIPQSIIDRYPANHLFYHN

IDNRDLTAVLNQLADILAQENKRFQINLHLNLFHSIDLFFAIYPIYQQYQHKISTIQLQLYD

DGSEGIVTQHSLCKIADLEQLILQHKNVLLELLTKGTANVPNPTLLRYLWNNIIDSQFHLI

SDHFLQHPKLQPLKRLLKRYTILDFTCYPRFNAEQKQLLKEILHISNELENLLKLLKQHNT

FLFTGTTAFNLDQEKLDLLTQLHILLLNEHQNPHSTHYIGNNYLLLIKGHANSPALNHTL

ALHFPDAIFLPANIPFEIFAMLGFTPNKMGGFASTSYINYPTENINIILFFLISDQPSTRIKW

LDYEKQFGLMSLLAMQKINEDQAFMCTIHN (pG544) pEC3'-(T7)delta20bstC-neuBCA-thyA

SEQ ID NO: 17

TCGCGCGTTTCGGTGATGACGGTGAAAACCTCTGACACATGCAGCTCCCGGAGACGGTCACAGC

TTGTCTGTAAGCGGATGCCGGGAGCAGACAAGCCCGTCAGGGCGCGTCAGCGGGTGTTGGCGGG

TGTCGGGGCTGGCTTAACTATGCGGCATCAGAGCAGATTGTACTGAGAGTGCACCATATATGCG

GTGTGAAATACCGCACAGATGCGTAAGGAGAAAATACCGCATCAGGCGCCTCCTCAACCTGTAT

ATTCGTAAACCACGCCCAATGGGAGCTGTCTCAGGTTTGTTCCTGATTGGTTACGGCGCGTTTC

GCATCATTGTTGAGTTTTTCCGCCAGCCCGACGCGCAGTTTACCGGTGCCTGGGTGCAGTACAT

CAGCATGGGGCAAATTCTTTCCATCCCGATGATTGTCGCGGGTGTGATCATGATGGTCTGGGCA

TATCGTCGCAGCCCACAGCAACACGTTTCCTGAGGAACCATGAAACAGTATTTAGAACTGATGC

AAAAAGTGCTCGACGAAGGCACACAGAAAAACGACCGTACCGGAACCGGAACGCTTTCCATTTT

TGGTCATCAGATGCGTTTTAACCTGCAAGATGGATTCCCGCTGGTGACAACTAAACGTTGCCAC

CTGCGTTCCATCATCCATGAACTGCTGTGGTTTCTGCAGGGCGACACTAACATTGCTTATCTAC

ACGAAAACAATGTCACCATCTGGGACGAATGGGCCGATGAAAACGGCGACCTCGGGCCAGTGTA

TGGTAAACAGTGGCGCGCCTGGCCAACGCCAGATGGTCGTCATATTGACCAGATCACTACGGTA

CTGAACCAGCTGAAAAACGACCCGGATTCGCGCCGCATTATTGTTTCAGCGTGGAACGTAGGCG

AACTGGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACATTGCC

AGCTACGCGTTATTGGTGCATATGATGGCGCAGCAGTGCGATCTGGAAGTGGGTGATTTTGTCT

GGACCGGTGGCGACACGCATCTGTACAGCAACCATATGGATCAAACTCATCTGCAATTAAGCCG

CGAACCGCGTCCGCTGCCGAAGTTGATTATCAAACGTAAACCCGAATCCATCTTCGACTACCGT

TTCGAAGACTTTGAGATTGAAGGCTACGATCCGCATCCGGGCATTAAAGCGCCGGTGGCTATCT

AATTACGAAACATCCTGCCAGAGCCGACGCCAGTGTGCGTCGGTTTTTTTACCCTCCGTTAAAT

TCTTCGAGACGCCTTCCCGAAGGCGCCATTCGCCATTCAGGCTGCGCAACTGTTGGGAAGGGCG

ATCGGTGCGGGCCTCTTCGCTATTACGCCAGCTGGCGAAAGGGGGATGTGCTGCAAGGCGATTA

-continued

AGTTGGGTAACGCCAGGGTTTTCCCAGTCACGACGTTGTAAAACGACGGCCAGTGCCAAGCTTA

CTGCTCACAAGAAAAAAGGCACGTCATCTGACGTGCCTTTTTTATTTGTACTACCCTGTACGAT

TACTGCAGGTCGACTTATTTTTTCCATATCTGTTCAACCTTTTTTAAATCCTCCAAACAGTCAA

TATCTAAACTTGAGCTTTCGTCCATTAAAAAATGCTTGGTTTTGCTTTGTAAAAAGCTAGGATT

GTTTAAAAATTCTTTTATCTTTAAAATATAAATTGCACCATTGCTCATATAAGTTTTAGGCAAT

TTTTGCCTTGGCATAAAAGGATATTCATCATTACAAATCCCTGCTAAATCGCCACAATCATTAC

AAACAAAGGCTTTTAGAATTTTATTATCACATTCGCTTACGCTAATTAGGGCATTTGCATTGCT

ATTTTTATAAAGATTAAAAGCTTCATTAATATGAATATTTGTTCTTAGCGGTGAAGTGGGTTGT

AAAAAAACTACATCTTCATAATCTTTATAAAATTTTAGAGCATGTAACAGCACTTTATCGCTTG

TGGTATCATCTTGTGCAAGGCTAATTGGGCGTTTTAAAATATCAACATTTTGACTTTTTGCATA

ATTTAAAATTTCATCACTATCACTGCTTACAACAACTTTACTAATGCTTTTAGCATTTAGTGCA

GCTTTGATCGTGTAGTAAATTAAAGGTTTATTGTTTAATAAAACCAAATTTTTATTTTTAATAC

CCTTTGAGCCACCACGAGCAGGGATTATTGCTAAGCTCATTTTATATCCTTAAAAACTTTTTGT

GTGCTGAGTTTAAAAAAATCTCCGCTTTGTAAATATTCAAAAAATAATTTTGAGCTATCTAAAA

TCTCTAACTTAGCGCTAAATAAATCTTGTTTTTTATGAATAGTGTTAATAGCTTTTAGTATTTC

ATCACTATTTGCATTAACTTTTAGTGTATTTTCATTGCCAAGTCTTCCATTTTGTCTTGAGCCA

ACTAAAATCCCTGCTGTTTTTAAGTATAAGGCCTCTTTTAAAATACAACTTGAATTACCTATTA

TAAAATCAGCATTTTTTAACAAAGTTATAAAATACTCAAATCTAAGCGATGGAAAAAGCTTAAA

TCTAGGGTTATTTTTAAACTCTTCATAGCTTTGCAAGATTAATTCAAAACCTAAATCATTATTT

GGATAAATAACAATATAATTTTTATTACTTTGTATCAGTGCTTTTACTAAATTGTCTGCTTGAT

TTTTAATGCTAGTAATTTCAGTTGTAACAGGATGAAACATAAGCAAAGCGTAGTTTTCATAATT

TATATCATAATATTTTTTTGCTTCGCTAAGTGAAATTTTATTATCGTTTAAAAGTTCTAAATCA

GGCGAACCTATGATAAAAATAGATTTTTCATCTTCTCCAAGCTGCATTAAACGCCTTTTTGCAA

ACTCATCATTTACTAAATGAATATGAGCTAGTTTTGATATAGCGTGGCGTAAGCTATCGTCAAT

AGTTCCTGAAATCTCTCCGCCTTCAATATGCGCTACTAAGATATTATTTAATGCTCCAACAATA

GCTGCTGCTAAAGGCTCAATTCTATCTCCATGTACTACGATTAAATCAGGTTTTAGCTCATTTG

CATACCTTGAAAATCCATCAATTGTAGTAGCTAAAGCCTTATCAGTTTGATAATATTTATCATA

ATTTATAAATTCATAAATATTTTTAAAGCCATTTTTATAAAGTTCTTTAACTGTATAGCCAAAA

TTTTTACTTAAGTGCATTCCTGTTGCAAAGATGTAAAGTTCAAATTCGCTTGAGTTTTGCACCC

TGTACATTAAAGATTTAATCTTAGAATAATCAGCCCTAGAGCCTGTTATAAAAAGGATTTTTTT

CACGCAAAATCCTCATAGCTTAACTGAGCATCATTTTCTATATCTCTTAATGCTTTTTTGCCTA

AAATATTTTCAAATTCAGCCGCACTAATTCCACCAAGTCCAGGTCTTTTAACCCAAATATTATC

CATAGATAAAACTTCGCCTTTTTTAATATCTTTAATGCTAACTACACTTGCAAAGGCAAAATCA

ATTGTAACTTGTTCTTGTTTAGCCGCTTTTTTACTTTCATTATTTCCTCTTATTATAGCCATTT

GCTCACTTTGTATAATTAGCTCTTTTAAAGCCTTTGTATCCATAGAACAAACTATATCAGGGCC

ACTTCTATGCATACTATCAGTAAAATGTCTTTCAAGCACACAAGCTCCAAGTACAACTGCACCT

GCTCACTTTGTATAATTAGCTCTTTTAAAGCCTTTGTATCCATAGAACAAACTATATCAGGGCC

ACTTCTATGCATACTATCAGTAAAATGTCTTTCAAGCACACAAGCTCCAAGTACAACTGCACCT

AAACACGCAAGATTATCTGTTGTGTGGTCGCTTAAGCCTACCATACAAGAAAATTCTTTTTTTA

ACTCAAGCATAGCGTTTAATCTTACAAGATTATGCGGGGTTGGGTAAAGATTGGTCGTGTGCAT

TAAAACAAAAGGAATTTCATTGTCTAATAAGATTTTTACAGTTGGTTTTATACTTTCAATACTA

-continued

TTCATTCCTGTGCTAACTATCATAGGCTTTTTAAAGGCTGCTATGTGTTTAATAAGCGGATAAT

TATTACACTCACCTGAACCAATCTTAAAAGCACTAACTCCCATATCTTCTAAGCGGTTCGCACC

TGCACGAGAAAAAGGTGTGCTAAGATAAACAAGACCTAATTTTTCTGTGTATTCTTTAAGTGCT

AGCTCATCTTTATAATCCAAAGCACATTTTTGCATAATCTCATAAATGCTTATTTTTGCATTAC

CAGGAATTACTTTTTTAGCGGCCTTACTCATCTCATCTTCAACAATATGAGTTTGATGCTTTAT

AATCTTAGCACCTGCGCTAAAGGCTGCATCTACCATAATTTTAGCTAGTTCTAAACTGCCATTA

TGATTAATGCCTATTTCAGGTACGACTAAGGGTGCTTTTTCTTCACTTATGATTATATTTTGTA

TTTTTATTTCTTTCATTTATTTTCCTCCTTAGTCGACGGTACACTTAAAAGTTGATCGGATTCG

GCATTTCTTCAAAAAAAATCTGTTCCGGAGTAATAACGTTCAGCATCAGCATCAGTTTGCTCAG

GGTCTGGGATTTGGCATCGTTTTCATTTTTGATTTTTTCGGAGCCCAGGAATACTACTTTATCG

ATGTTTTTCGGTGGCAGGCTAAAGTACACGGTAGACATGATGCCACCTACATAGTCCGGCAGAG

AGTTGGTCATCATCAGAACTTCGAACGGGATGTTGGCCGGGATTTTTTCCGCACCGGTTTTGCG

GATAATATAGTCGTTGATATCGTCGCCTTTCGGGTGGCCTTTGAAGAAGATTTTAATGTCGTTA

CCCAGATAGAATTTGCCGTTCGGTTTGATAAAGGATTCCAGGATTTCCGTCTGCAGTTTCGCGT

TGTTCAGACGTTTTTTTTTATCTTTCTCCCAGGTGGTGGTACCGGTGAAGATGAAAGTTTTATA

TTCTTTGTTTTTGGTACCAATGTTCAGTTCGTTGAAGATGTTCTGATCAAAGTGAGTAATTTTC

AGGAACAGTTCTTTCTGGTTCTTAGAGAAGTGAGAAAAGCGGCTCAGATCCATGCTAACAATGG

TGTCAGACAGGAAATGCTTCAGCGGCTGCATCTTTTCGTCGATATCCAGATAGTCCGGGCGCAG

CAGAATGTATTCGGTCGGAAAAATCTTGTGCCAAGTGTAACGGGTCAGAGAATGCAGTTTGTCG

GTATCAGTTTCACGGTTCTCCAGTGCGTCCTTCAGCTTTTTCTGTGCTTCGATCAGGATTGCGC

TGATGTTTTCCTGACGATGCTGATACAGATCTACGTAGTTACCAGAGCCGTCGTCGTACAGATA

CAGCTTTTCGATGTTGATCTTGTGGAACAGCGGGGACAGGGTTTTGAAAATAGACAGCAGAGAA

CGAACAGAATGATCCAGGTTAGTGTGAATAATCAGGTCCACCGGGGTATCGCTTTTTTCGATGT

TCAGGTACAGTTTGTCGCTGAACTCCTTAATGTCCAGAATGCTCACTTTGGAGAACTCGATGCG

CTCTTTGGAGAAAGAGTTCAGAATTTCTTTGTTGAAATCGAAGCGTTCAAAACCGATGATACGT

TCCACTTTCTCATTATTTTTGTTTTCAACCAGATTCAGGATCATGTTCAGGCTAGGCAGGGATG

CGTAGTCCAGGTAAATTTCCATATGTATATCTCCTTCTTGAATTCTAACAATTGATTGAATGTA

TGCAAATAAATGCATACACCATAGGTGTGGTTTAATTTGATGCCCTTTTTCAGGGCTGGAATGT

GTAAGAGCGGGGTTATTTATGCTGTTGTTTTTTTGTTACTCGGGAAGGGCTTTACCTCTTCCGC

ATAAACGCTTCCATCAGCGTTTATAGTTAAAAAAATCTTTCGGAACTGGTTTTGCGCTTACCCC

AACCAACAGGGGATTTGCTGCTTTCCATTGAGCCTGTTTCTCTGCGCGACGTTCGCGGCGGCGT

GTTTGTGCATCCATCTGGATTCTCCTGTCAGTTAGCTTTGGTGGTGTGTGGCAGTTGTAGTCCT

GAACGAAAACCCCCCGCGATTGGCACATTGGCAGCTAATCCGGAATCGCACTTACGGCCAATGC

TTCGTTTCGTATCACACACCCCAAAGCCTTCTGCTTTGAATGCTGCCCTTCTTCAGGGCTTAAT

TTTTAAGAGCGTCACCTTCATGGTGGTCAGTGCGTCCTGCTGATGTGCTCAGTATCACCGCCAG

TGGTATTTATGTCAACACCGCCAGAGATAATTTATCACCGCAGATGGTTATCTGTATGTTTTTT

ATATGAATTTATTTTTTGCAGGGGGGCATTGTTTGGTAGGTGAGAGATCAATTCTGCATTAATG

AATCGGCCAACGCGCGGGGAGAGGCGGTTTGCGTATTGGGCGCTCTTCCGCTGCTAGCGGAGTG

TATACTGGCTTACTATGTTGGCACTGATGAGGGTGTCAGTGAAGTGCTTCATGTGGCAGGAGAA

AAAAGGCTGCACCGGTGCGTCAGCAGAATATGTGATACAGGATATATTCCGCTTCCTCGCTCAC

-continued

TGACTCGCTACGCTCGGTCGTTCGACTGCGGCGAGCGGAAATGGCTTACGAACGGGGCGGAGAT

TTCCTGGAAGATGCCAGGAAGATACTTAACAGGGAAGTGAGAGGGCCGCGGCAAAGCCGTTTTT

CCATAGGCTCCGCCCCCCTGACAAGCATCACGAAATCTGACGCTCAAATCAGTGGTGGCGAAAC

CCGACAGGACTATAAAGATACCAGGCGTTTCCCCCTGGCGGCTCCCTCGTGCGCTCTCCTGTTC

CTGCCTTTCGGTTTACCGGTGTCATTCCGCTGTTATGGCCGCGTTTGTCTCATTCCACGCCTGA

CACTCAGTTCCGGGTAGGCAGTTCGCTCCAAGCTGGACTGTATGCACGAACCCCCCGTTCAGTC

CGACCGCTGCGCCTTATCCGGTAACTATCGTCTTGAGTCCAACCCGGAAAGACATGCAAAAGCA

CCACTGGCAGCAGCCACTGGTAATTGATTTAGAGGAGTTAGTCTTGAAGTCATGCGCCGGTTAA

GGCTAAACTGAAAGGACAAGTTTTGGTGACTGCGCTCCTCCAAGCCAGTTACCTCGGTTCAAAG

AGTTGGTAGCTCAGAGAACCTTCGAAAAACCGCCCTGCAAGGCGGTTTTTTCGTTTTCAGAGCA

AGAGATTACGCGCAGACCAAAACGATCTCAAGAAGATCATCTTATTAATCAGATAAAATATTTC

TAGGCGGCCGCGAACGAAAACTCACGTTAAGGGATTTTGGTCATGAGATTATCAAAAAGGATCT

TCACCTAGATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCTATTTCGT

TCATCCATAGTTGCCTGACTCCCCGTCGTGTAGATAACTACGATACGGGAGGGCTTACCATCTG

GCCCCAGTGCTGCAATGATACCGCGAGACCCACGCTCACCGGCTCCAGATTTATCAGCAATAAA

CCAGCCAGCCGGAAGGGCCGAGCGCAGAAGTGGTCCTGCAACTTTATCCGCCTCCATCCAGTCT

ATTAATTGTTGCCGGGAAGCTAGAGTAAGTAGTTCGCCAGTTAATAGTTTGCGCAACGTTGTTG

CCATTGCTACAGGCATCGTGGTGTCACGCTCGTCGTTTGGTATGGCTTCATTCAGCTCCGGTTC

CCAACGATCAAGGCGAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGTTATGGCAGCACTGC

ATAATTCTCTTACTGTCATGCCATCCGTAAGATGCTTTTCTGTGACTGGTGAGTACTCAACCAA

GTCATTCTGAGAATAGTGTATGCGGCGACCGAGTTGCTCTTGCCCGGCGTCAATACGGGATAAT

ACCGCGCCACATAGCAGAACTTTAAAAGTGCTCATCATTGGAAAACGTTCTTCGGGGCGAAAAC

TCTCAAGGATCTTACCGCTGTTGAGATCCAGTTCGATGTAACCCACTCGTGCACCCAACTGATC

TTCAGCATCTTTTACTTTCACCAGCGTTTCTGGGTGAGCAAAAACAGGAAGGCAAAATGCCGCA

AAAAAGGGAATAAGGGCGACACGGAAATGTTGAATACTCATACTCTTCCTTTTTCAATATTATT

GAAGCATTTATCAGGGTTATTGTCTCATGAGCGGATACATATTTGAATGTATTTAGAAAAATAA

ACAAATAGGGGTTCCGCGCACATTTCCCCGAAAAGTGCCACCTGACGTCTAAGAAACCATTATT

ATCATGACATTAACCTATAAAAATAGGCGTATCACGAGGCCCTTTCGTC (Δ20BstC)

SEQ ID NO: 18

MEIYLDHASLPSLNMILNLVENKNNEKVERIIGFERFDFNKEILNSFSKERIEFSKVSILDIK

EFSDKLYLNIEKSDTPVDLIIHTNLDHSVRSLLSIFKTLSPLFHKINIEKLYLYDDGSFNYV

DLYQHRQENISAILIEAQKKLKDALENRETDTDKLHSLTRYTWHKIFPTEYILLRPDYLDI

DEKMQPLKEIFLSDTIVSMDLSRFSHFSKNQKELFLKITHFDQNIFNELNIGTKNKEYKTFI

FTGTTTWEKDKKKRLNNAKLQTEILESFIKPNGKFYLGNDIKIFFKGHPKGDDINDYIIRK

TGAEKIPANIPFEVLMMTNSLPDYVGGIMSTVYFSLPPKNIDKVVFLGSEKIKNENDAKS

QTLSKLMLMLNVITPEQIFFEEMPNPINF (BstC*)

SEQ ID NO: 19

MRKIITFFSLFFSISAWCQKMEIYLDYASLPSLNMILNLVENKNNEKVERIIGFERFDFNKE

ILNSFSKERIEFSKVSILDIKERSDKLYLNIEKSDTPVDLIIHTNLDHSVRSLLSIFKTLSPLF

-continued

HKINIEKLYLVDDGSGNYVDLYQHRQENISAILIEAQKKLKDALENRETDTDKLHSLTRY

TWHKIFPTEYILLRPDYLDIDEKMQPLKHFLSDTIVSMDLSRFSHFSKNQKELFLKITHFD

QNIFNELNIGTKNKEYKTFIFTGTTTWEKDKKKRLNNAKLQTEILESFIKPNGKFYLGNDI

KIFFKGHPKGDDINDYIIRKTGAEKIPANIPFEVLMMTNSLPDYVGGIMSTVYFSLPPKNI

DKVVFLGSEKIKNENDAKSQTLSKLMLMLNVITPEQIFFEEMPNPINF (BstD*)

SEQ ID NO: 20

MFKIKSYGKNPQLQAVDIYIDFATIPSLSYFLHFLKHKHDHQRLRLFSLARFEMPQTVIEQ

YEGIIQFSRNVEHNVEPLLEQLQTILSQEGKQFELHLHLNLFHSFEMFLNLSPTYTKYKEK

ISKIVLHLYDDGSEGVMKQYQLQKSSSLVQDLAATKASLVSLFENGEGSFSQIDLIRYVW

NAVLETRYYLLSDHFLLDEKLQPLKAELGHYQLLNLSTYQYLSSEDLLWLKQILKIDAE

LESLMQKLTAQPVYFFSGTTFLG (BstE*)

SEQ ID NO: 21

MLIQQNLEIYLDYATIPSLACFMHFIQHKDDVDSIRLFGLARFDIPQSIIDRYPANHLFYHN

IDNRDLTAVLNQLADILAQENKRFQINLHLNLFHSIDLFFAIYPIYQQYQHKISTIQLQLYD

DGSEGIVTQHSLCKIADLEQLILQHKNVLLELLTKGTANVPNPTLLRYLWNNIIDSQFHLI

SDHFLQHPKLQPLKRLLKRYTILDFTCYPRFNAEQKQLLKEILHISNELENLLKLLKQHNT

FLFTGTTAFNLDQEKLDLLTQLHILLLNEHQNPHSTHYIGNNYLLLIKGHANSPALNHTL

ALHFPDAIFLPANIPFEIFAMLGFTPNKMGGFASTSYINYPTENINIILFFLISDQPSTRIKW

LDYEKQFGLMSLLAMQKINEDQAFMCTIHN (BstH*)

SEQ ID NO: 22

MKRLFRLFLCLALLSGTAACSDDEVSQNLIVINGGEHFLSLDGLARAGKISVLAPAPWR

VTKAAGDTWFRLSATEGPAGYSEVELSLDENPGAARSAQLAFACGDARTFRLSQGALS

AGYDSPDYYFYVTFGTMPTLYAGIHLLSHDKPGYVTFYSRSKTFDPAEFPARAEVTTAAD

RTADATQAEMEAMAREMKRRILEINSADPTAVFGLYVDDLRCRIGYDWFVAQGIDSAR

VKVSMLSDGTGTYNNFYNYFGDAATAEQNWESYASEVEALDWNHGGRYPETRSLPEF

ESYTWPYYLSTRPDYRLVVQDGSLLESSCPFITEKLGEMEIESIQPYEMLSALPESSRKRF

YDMAGFDYDKFAALFDASPKKNLIIIGTSHADDASARLQRDYVARIMEQYGAQYDVFF

KPHPADTTSAGYETEFPGLTLLPGQMPFEIFVWSLIDRVDMIGGYPSTVFLTVPVDKVRFI

FAADAASLVRPLNILFRDATDVEWMQ (BstI*)

SEQ ID NO: 23

MEFCKMATTQKICVYLDYATIPSLNYILHFAQHFEDQETIRLFGLSRFHIPESVIQRYPKG

VVQFYPNQEKDFSALLLALKNILIEVKQQQRKCEIELHLNLFHYQLLLLPFLSLYLDTQD

YCHLTLKFYDDGSEAISALQELALAPDLAAQIQFEKQQFDELVVKKSFKLSLLSRYFWG

KLFESEYIWFNQAILQKAELQILKQEISSSRQMDFAIYQQMSDEQKQLVLEILNIDLNKVA

YLKQLMENQPSFLFLGTTLFNITQETKTWLMQMHVDLIQQYCLPSGQFFNNKAGYLCF

YKGHPNEKEMNQMILSQFKNLIALPDDIPLEILLLLGVIPSKVGGFASSALFNFTPAQIENI

IFFTPRYFEKDNRLHATQYRLMQGLIELGYLDAEKSVTHFEIMQLLTKE (BstJ*)

SEQ ID NO: 24

MLVNNQSHNPKLICWQRHPVNDEALLQGINAASFVSIASLCQHAATLLAGHPHSHLITIYG

NTYWSKDLARLIRYLTRISGVEIKKLELIDDGSSEYQKMFYWQRLSSEEQTRDLATGLK

-continued

NLKSYLSGNDNKLLRLLTGHSNKLPRRLSSFMNWHQLFPTTYHMLRMDYLDKPELHQL

KQYLGNNAQQIRWNYIADNLFDDEQQSLFYQLLGISLAEQKQLRAGRQQLHDFMFIGV

DSSNASSKLQINVIADSRQESGIIPTITAKKMLFKGHPFANFNQTIVDAHQMGEMPAMIPF

ETLIMTGNLPQKVGGMASSLYFSLPNNYHIEYIVFSGSKKDLEQHALLQIMLYTKVISPE

RVYFSEQFKSC (BstM*)

SEQ ID NO: 25

MKKPLIIAGNGPSIKDLDYSLFPKDFEVFRCNQFYFEDKYYLGREIKGVFFNPCVLSSQM

QTAQYLMDNGEYSIERFFCSVSTDRHDFDGDYQTILPVEGYLKAHYPFVCDTFSLFKGH

EEILRHVKYHLKTYSKELSAGVLMLLSAVVLGYKEIYLVGIDFGASSWGHFYDESQSQH

FSNHMADCHNIYYDMFTICLCQKYAKLYALAPNSPLRHILALNPQAKYHFELLDKPIGY

TSDLIVSLPLEEKLLEFKNIEEKLLEFKNIEEKLLEFKNIEEKLLVNRLKNILRKIKRKILPF

WGGGGNTHLKVSFRWGVA (BstN*)

SEQ ID NO: 26

MSEKIFSQVDEKNQKKPLIIGNGPSIKDLDYSLFPKDFDVFRCNQFYFEDKYYLGKEVK

GVFFNPCVFHNQMNTAKHLIDNNEYYIEQFFCSVSKEQHDFNGDYQTILSVDEYLRANY

PFVRDTFSLFGEHEEILNHVKYHLKTYSKELSAGVLMLLSAIVLGYKEIYLVGVDFGANS

WGHFYDDNQSQHFINHMADCHNIYYDMLTIYLCQKYAKLYALVPNSPLNHLLPLNLQA

NHVFELLDKPIGYTSDLIVSSPLEEKLLESKNIDERFSQNKSFKNYLQRLKDKFLQMIFRG

GGVITIPRVIFKGKFA (Δ20BstC*2)

SEQ ID NO: 27

MEIYLDHASLPSLNMILNLVENKNNEKVERIIGFERFDFNKEILNSFSKERIEFSKVSILDIK

EFSDKLYLNIEKSDTPVDLIIHTNLDHSVRSLLSIFKTLSPLFHKINIEKLYLYDDGSFNYV

DLYQHRQENISAILIEAQKKLKDALENRETDTDKLHSLTRYTWHKIFPTEYILLRPDYLDI

DEKMQPLKEIFLSDTIVSMDLSRFSHFSKNQKELFLKITHFDQNIFNELNIGTKNKEYKTFI

FTGTTTWEKDKKKRLNNAKLQTEILESFIKPNGKFYLGNDIKIFFKGHPKGDDINDYIIRK

TGAEKIPANIPFEVLMMTNSLPDYVGGIMSTVYFSLPPKNIDKVVFLGSEKIKNENDAKS

QTLSKLMLMLNVITPEQIFFEEMPNPINF (Δ20BstC*3)

SEQ ID NO: 28

MEIYLDHASLPSLNMILNLVENKNNEKVERIIGFERFDFNKEILNSFSKERIEFSKVSILDIK

EFSDKLYLNIEKSDTPVDLIIHTNLDHSVRSLLSIFKTLSPLFHKINIEKLYLYDDGSFNYV

DLYQHRQENISAILIEAQKKLKDALENRETDTDKLHSLTRYTWHKIFPTEYILLRPDYLDI

DEKMQPLKEIFLSDTIVSMDLSRFSHFSKNQKELFLKITHFDQNIFNELNIGTKNKEYKTFI

FTGTTTWEKDKKKRLNNAKLQTEILESFIKPNGKFYLGNDIKIFFKGHPKGDDINDYIIRK

TGAEKIPANIPFEVLMMTNSLPDYVGGIMSTVYFSLPPKNIDKVVFLGSEKIKNENDAKS

QTLSKLMLMLNVITPEQIFFEEMPNPINF (Δ20BstC*4)

SEQ ID NO: 29

MEIYLDHASLPSLNMILNLVENKNNEKVERIIGFERFDFNKEILNSFSKERIEFSKVSILDIK

EFSDKLYLNIEKSDTPVDLIIHTNLDHSVRSLLSIFKTLSPLFHKINIEKLYLYDDGSFNYV

DLYQHRQENISAILIEAQKKLKDALENRETDTDKLHSLTRYTWHKIFPTEYILLRPDYLDI

DEKMQPLKEIFLSDTIVSMDLSRFSHFSKNQKELFLKITHFDQNIFNELNIGTKNKEYKTFI

FTGTTTWEKDKKKRLNNAKLQTEILESFIKPNGKFYLGNDIKIFFKGHPKGDDINDYIIRK

-continued

TGAEKIPANIPFEVLMMTNSLPDYVGGIMSTVYFSLPPKNIDKVVFLGSEKIKNENDAKS

QTLSKLMLMLNVITPEQIFFEEMPNPINF (Δ20BstC*5)

SEQ ID NO: 30

MEIYLDHASLPSLNMILNLVENKNNEKVERIIGFERFDFNKEILNSFSKERIEFSKVSILDIK

EFSDKLYLNIEKSDTPVDLIIHTNLDHSVRSLLSIFKTLSPLFHKINIEKLYLYDDGSFNYV

DLYQHRQENISAILIEAQKKLKDALENRETDTDKLHSLTRYTWHKIFPTEYILLRPDYLDI

DEKMQPLKEIFLSDTIVSMDLSRFSHFSKNQKELFLKITHFDQNIFNELNIGTKNKEYKTFI

FTGTTTWEKDKKKRLNNAKLQTEILESFIKPNGKFYLGNDIKIFFKGHPKGDDINDYIIRK

TGAEKIPANIPFEVLMMTNSLPDYVGGIMSTVYFSLPPKNIDKVVFLGSEKIKNENDAKS

QTLSKLMLMLNVITPEQIFFEEMPNPINF

EXAMPLES

Example 1

Identification New Sialyltransferases (STs) For Synthesis of Sialyl-Oligosaccharides in Engineered Bacterial Hosts

Identification of New STs Using Pst6-224 From *Photobacterium* spp. Strain JT-ISH-224

Sialyltransferases identified from both prokaryotic and eukaryotic organisms are categorized into 5 distinct sequence families (GT29, GT38, GT42, GT52 and GT80) and possess at least two structural folds (GT-A and GT-B), (Audry, M., et al (2011). Glycobiology 21, 716-726). Eukaryotic sialytransferases (the GT29 family and GT-A fold) are transmembrane molecules found in the secretory pathway, and as such they present a heterologous expression problem for their use within the cytoplasm of engineered microbes as described herein. For this reason new examples in this family were not pursued, instead new sialyltransferases (STs) of the bacterial GT80 family (and the GT-B fold) were identified that were useful for synthesis of sialyl-oligosaccharides in engineered bacterial hosts.

To this end, sequential screens of DNA sequence databases were performed. First, the sequence of a single known lactose-accepting α(2,6) sialyltransferase, Pst6-224 from *Photobacterium* spp. strain JT-ISH-224 (Drouillard, S., et al. (2010). Carbohydr Res 345, 1394-99 SEQ ID NO: 1), was used to search public databases to find simple homologs that might represent additional lactose-accepting STs. The amino acid sequence of Pst6-224 was used as a query in the search algorithm PSI-BLAST (Position Specific Iterated Basic Local Alignment Search Tool) in order to identify sequence homologs. The PSI-BLAST program, using a given query protein sequence, generates a list of closely related protein sequences based on a homology search of a database. These protein homolog hits are then used by the program to generate a profile reflecting their sequence similarities to the original query. The profile is then used by the algorithm to identify an expanded group of homolog proteins, and the process is iterated several times until the number of additional new candidates obtained after each iteration decreases (Altschul, S. F., et al. (1990) J. Mol. Biol 215, 403-410; Altschul, S. F., et al. (1997) Nucleic Acids Res 25, 3389-3402).

The Pst6-224 amino acid sequence was used as a query for 6 iterations of the PSI-BLAST search algorithm. This approach yielded a group of unique 433 candidates with varying degrees of similarity to Pst6-224, many of which (117) were highly related to Pst6-224 (shared amino acid identity in the range of 50-90%) as well as a group that was more distantly related (shared amino acid identity less than 50%). Of note, Pst6-224 produced sub-optimal yields of 6'-SL, with a tendency to produce undesirable side products when used in a metabolically engineered *E. coli* production strain (Drouillard et al., 2010). In addition, elevated production of Pst6-224 appeared to be moderately toxic in certain *E. coli* production strains, including the preferred strain for use herein. Therefore, candidates for further analysis were deliberately (and somewhat counterintuitively) targeted from the more distantly related group identified via the PSI-BLAST search (shared amino acid identity to Pst6-224 of less than 30% over greater than 250 resides) (Table 1).

TABLE 1

Candidates further analyzed with less than 30% sequence identity to Pst6-224

| Gene name | Organism | Accession number | GT family | % identity to Pst6-224 | SEQ ID # |
|---|---|---|---|---|---|
| Pst6-224 | *Photobacterium* sp. JT-ISH-224 | BAF92026.1 | GT80 | 100 | 1 |
| BstC | *Avibacterium paragallinarum* | WP_021724759.1 | putative GT80 | 26.1 | 2 |
| BstD | *Actinobacillus ureae* | WP_005625206.1 | n/a | 8.9 | 3 |
| BstE | *Haemophilus_ ducreyi* | AAP95068.1 | putative GT80 | 15.9 | 4 |
| BstH | *Alistipes* (multispecies) | WP_018695526.1 | putative GT80 | 13.3 | 5 |
| BstI | *Bibersteinia trealosi* | AGH37861.1 | putative GT80 | 16.4 | 6 |
| BstJ | *Shewanella piezotolerans* | YP_002314261.1 | n/a | 18.9 | 7 |

This group of candidates shared certain similarities primarily within the catalytic domain region of the respective proteins as inferred from the observation that they all belong to the same Pfam protein family, but not necessarily similarities in their protein domain organization. It must be noted that the presence of a "sialyltransferase" Pfam domain ensures nothing obvious about the actual catalytic ability of the protein in term of specific activity, catalytic rate, substrate specificity and/or product specificity, and that substantial experimentation is required to verify candidate genes for their desired properties. This group of candidates may include similar, better or distinct α(2,6) ST activities relative to Pst6-224, but that they are different enough at the amino acid level to avoid the cryptic toxicity and other functional shortcomings (e.g. poorer specificity) observed with Pst6-224 expressed in production strains.

These more distantly related (less than 30% sequence identity to Pst6-224) candidate STs were further screened to identify those candidate STs arising from bacterial species that may or are known to incorporate sialic acid into their cell surface glycan structures. Candidate STs from these types of organisms are more likely to utilize CMP-N-acetylneuraminic acid (CMP-Neu5Ac) as a sugar nucleotide donor substrate, given the presence of sialic acid in their surface carbohydrate structures. Candidate STs from commensals or pathogens were also identified. Such organisms sometimes display carbohydrate structures on their cell-surface that contain sialic acid. Again, candidate STs from these types of organisms are believed to be more likely to utilize CMP-Neu5Ac as a donor substrate and also to catalyze the linkage of sialic acid to useful acceptor oligosaccharides.

6 candidate STs with identities to Pst6-224 ranging from 8.9 to 26.1% at the amino acid level were selected from PSI-BLAST screens based on these criteria (Table 1). These proteins were often annotated in databases as "hypothetical proteins" and had no assigned name. For ease of description, the genes encoding these proteins were named bst for bacterial sialyltransferase, followed by a letter identifying them uniquely.

Database Screen Using MAC1268 From *Helicobacter acinonychis* (a lactose-utilizing α(2,6) ST) as the Search Probe A second sequence database screen was conducted using a second lactose-utilizing α(2,6) ST as the search probe (HAC1268 from *Helicobacter acinonychis* (Schur, M. J., et al. (2012). Glycobiology 22, 997-1006, SEQ ID NO: 8). HAC1268 is a member of the GT42 sialyltransferase family, possessing a predicted structural fold (the GT-A fold) distinct from the Pst6-224 ST sequence (that was used as the probe in the first database screen, described above, in).

Two candidate STs with identities to HAC1268 of 70.6% and 52.9% at the amino acid level (Table 2) were selected for further evaluation. FIG. 2 presents a pairwise % amino acid sequence identity comparison between the two α(2,6) ST probe sequences and the 8 identified ST candidates. Synthetic bst genes for these candidates were designed and codon-optimized in silica for *E. coli* expression using standard bioinformatic algorithms known to the art, and engineered with modified ribosomal binding sites to tune translation to appropriate levels in *E. coli.*

TABLE 2

Candidates identified and analyzed for further evaluation

| Gene name | Organism | Accession number | GT family | % identity to HAC1268 | SEQ ID # |
|---|---|---|---|---|---|
| HAC1268 | *Helicobacter acinonychis* | CAK00018.1 | GT42 | 100 | 8 |
| BstM | *Helicobacter pylori* | WP_000743106.1 | putative GT42 | 70.6 | 9 |
| BstN | *Helicobacter cetorum* | WP_014661583.1 | putative GT42 | 52.9 | 10 |

Of note, the first 20 residues of the amino acid sequence encoded by bstC were predicted to harbor a signal sequence that would direct the protein to the secretory pathway in *E. coli*, therefore a version of bstC lacking these residues (termed Δ20bstC) was designed and tested (SEQ ID NO: 18)

Also of note, the first 16 residues of the amino acid sequence of Pst6-224 were also predicted to harbor a signal sequence, therefore a version of the gene encoding Pst6-224 lacking these residues (termed Δ16Pst6-224) was designed and tested. Synthetic bst genes were synthesized in vitro by the Gibson Assembly method utilizing synthetic "gBlock" oligonucleotides (obtained from Integrated DNA Technologies), and cloned using standard molecular biological techniques into *E. coli* expression plasmids.

Expression and Transformation For Production of Sialyllactose (SL)

Expression Vector

Figure 3:
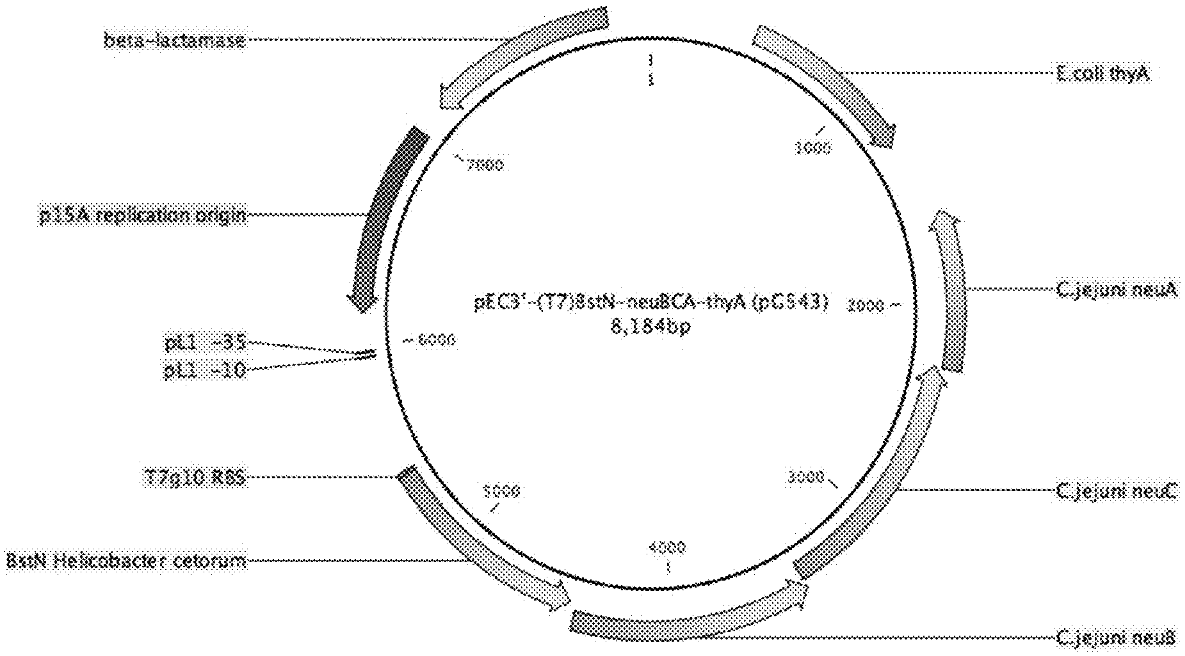
FIG. 3 is a map of an expression vector carrying one of the candidate ST genes, bstN (plasmid pG543, SEQ ID NO: 11).

The expression vector utilized to express the candidate bst genes, and to test for their ability to make sialyllactose, is a p15A origin-based plasmid carrying the strong bacteriophage λ pL promoter to drive expression of heterologous genes. In addition, the plasmid carries a β-lactamase (bla) gene for maintaining the plasmid in host strains using ampicillin selection (for convenience in the laboratory), and additionally it carries a native *E. coli* thyA (thymidylate synthase) gene as an alternative means of selection in thyA minus hosts. The plasmid also carries, downstream of the pL promoter and in an operon configuration downstream of the candidate bst gene, three heterologous biosynthetic genes from *Campylobacter jejuni* (neuB, neuC, and neuA; encoding N-acetylneuraminate synthase, UDP-N-acetylglucosamine 2-epimerase, and N-acetylneuraminate cytidylyltransferase respectively). These enzymes confer on *E. coli* the ability to convert UDP-GlcNAc into CMP-Neu5Ac. CMP-Neu5Ac is then available as a donor substrate for the candidate sialyltransferases to utilize in converting intracellular lactose to sialyllactose. FIG. 3 is a map of this expression vector carrying one of the candidate ST genes, bstN (plasmid pG543, SEQ ID NO: 11).

Development of Host Strain

Figure 4:
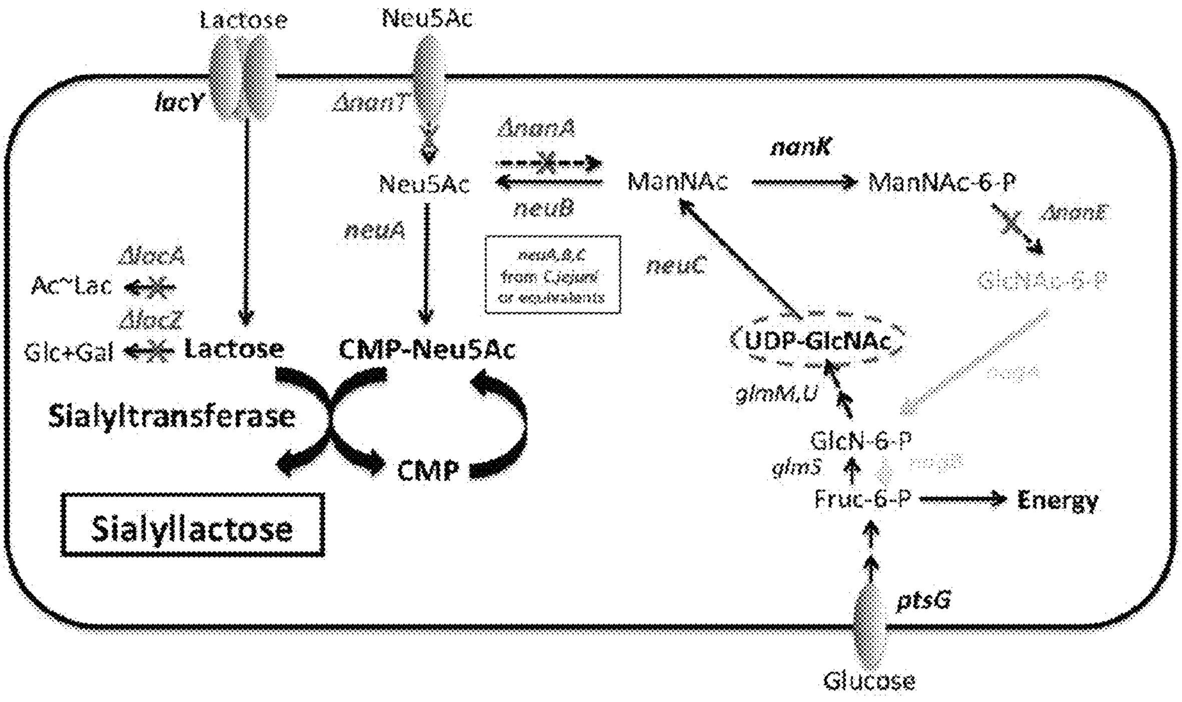
FIG. 4 is a diagram outlining the scheme for SL biosynthesis in engineered *E. coli.*

The candidate sialyltransferase gene expression plasmids were transformed into a host strain useful for the production of sialyllactose (SL). Biosynthesis of SL requires the generation of an enhanced cellular pool of both lactose and CMP-Neu5Ac (FIG. 4 outlines the scheme for SL biosynthesis in engineered *E. coli*). The wild-type *Escherichia coli* K12 prototrophic strain W3110 was selected as the starting point for engineering a host background to test the ability of the candidates to catalyze sialyllactose production (Bachmann, B. J. (1972). PBacteriol Rev 36, 525-557). The particular W3110 derivative employed was one that previously had been modified by the introduction (at the ampC locus) of a tryptophan-inducible $P_{trpB}$cI+ repressor cassette, generating an *E coli* strain known as GI724 (LaVallie et al., 2000).

Other features of GI724 include lacIq and lacPL8 promoter mutations. *E. coli* strain GI724 affords economical production of recombinant proteins from the phage λ $P_L$ promoter following induction with low levels of exogenous tryptophan (LaVallie, E. R., et al. (1993). Biotechnology (NY) 11, 187-193; Mieschendahl, Petri, and Hänggi (1986). *Bio/Technology* 4, 802-08). Additional genetic alterations were made to this strain to promote the biosynthesis of SL. This was achieved in strain GI724 through several manipulations of the chromosome using λ Red recombineering (Court, D. L., et al. (2002). Annu Rev Genet 36, 361-388) and generalized P1 phage transduction (Li, X. T., et al. (2013), Nucleic Acids Res 41, e204).

First: the ability of the *E. coli* host strain to accumulate intracellular lactose was engineered by deletion of the endogenous β-galactosidase gene (lacZ). The strain thus modified maintains its ability to transport lactose from the culture medium (via LacY, the lactose permease), but is deleted for the wild-type copy of the lacZ gene responsible for lactose catabolism. An intracellular lactose pool is therefore created when the modified strain is cultured in the presence of exogenous lactose. In addition, the lacA gene was deleted in order to eliminate production of acetyl-lactose from the enhanced pool of intracellular lactose. In a variation of this strain, the lacZ and lacI genes were simultaneously deleted such that the enhanced constitutive lacIq promoter was placed immediately upstream of the lactose permease gene lacY.

Second: A pool of the sugar nucleotide donor CMP-Neu5Ac was generated in the cytosol of the cell by co-expression of three genes from *Campylobacter jejuni* ATCC43484 (detailed above) encoding i) N-acetylneuraminate synthase (NeuB), ii) UDP-N-acetylglucosamine 2-epimerase (NeuC), and iii) N-acetylneuraminate cytidylyltransferase (NeuA). The neuBCA gene products function together in the enzymatic conversion of endogenous UDP-GlcNAc to CMP-Neu5Ac. The neuBCA genes are co-expressed in an operon, downstream from the bst gene on the plasmid expression vector and driven from the pL promoter, In addition, to prevent degradation of the Neu5Ac utilized to produce CMP-Neu5Ac, endogenous host cell genes encoding enzymes involved in sialic acid degradation were specifically deleted using λ red recombineering. The sialic acid catabolic pathway in *E. coli* is encoded by the nan operon, consisting of the nanRATEK genes (Hopkins, A. P., et al. (2013). FEMS Microbiol Lett 347, 14-22). Specifically, the nanATE genes were deleted to stabilize CMP-Neu5Ac pools within the cell.

In other embodiments of the SL production strain, a thyA (thymidylate synthase) mutation was introduced to the strain by almost entirely deleting the thyA gene and replacing it by an inserted functional, wild-type but promoter-less *E. coli* $lacZ^+$ gene carrying a weak ribosome binding site (ΔthyA::0.8RBS $lacZ^+$). This chromosomal modification was constructed utilizing λ red recombineering. In the absence of exogenous thymidine, thyA strains are unable to make DNA and die. This defect can be complemented in trans by supplying a wild-type thyA gene on a multi-copy plasmid (Belfort, M., et al. (1983), Proc Natl Acad Sci USA 80, 1858-861). This complementation scheme was used as a means of plasmid maintenance.

Further, the inserted 0.8RBS $lacZ^+$ cassette not only knocks out thyA, but also converts the $lacZ^-$ host back to both a $lacZ^+$ genotype and phenotype. The modified strain produced a minimal (albeit still readily detectable) level of β-galactosidase activity (0.3 units), which has very little impact on sialyllactose production during bioreactor production runs, but which is useful in removing residual lactose at the end of runs, and as an easily scorable phenotypic marker for moving the thyA region into other $lacZ^-$ *E. coli* strains by P1 phage transduction.

The final strain used the test the ST candidate genes (E1406) had the following genotype:

PlacIq-lacY, Δ(lacI-lacZ), ΔlacA, ΔthyA::(0.8RBS lacZ+), ampC::(Ptrp M13g8 RBS-λcI+, CAT), ΔnanATE::scar.

Transformants of this strain harboring the different ST (bst) candidate expression plasmids were evaluated for their ability to synthesize sialyllactose in 20×150 mm test tubes, containing 6 mL of IMC medium ("Induction Medium Casamino acids") (LaVallie, E. R., DiBlasio, E. A., Kovacic, S., Grant, K. L., Schendel, P. F., and McCoy, J. M. (1993). A thioredoxin gene fusion expression system that circumvents inclusion body formation in the *E. coli* cytoplasm. Biotechnology (NY) 11, 187-193, the entire content of which is incorporated herein by reference) of the following recipe:

$Na_2HPO_4$=6 g/L
$KH_2PO_4$=3 g/L
NaCl=0.5 g/L
$NH_4Cl$=1 g/L
1 mM $MgSO_4$
0.1 mM $CaCl_2$
0.5% glucose w/v
0.4% casamino acids (Difco technical)

In some embodiments, the glucose and/or casamino acids concentrations are varied in the 0.05-1% range.

Cell Growth Expression and Characterization

Figure 5:
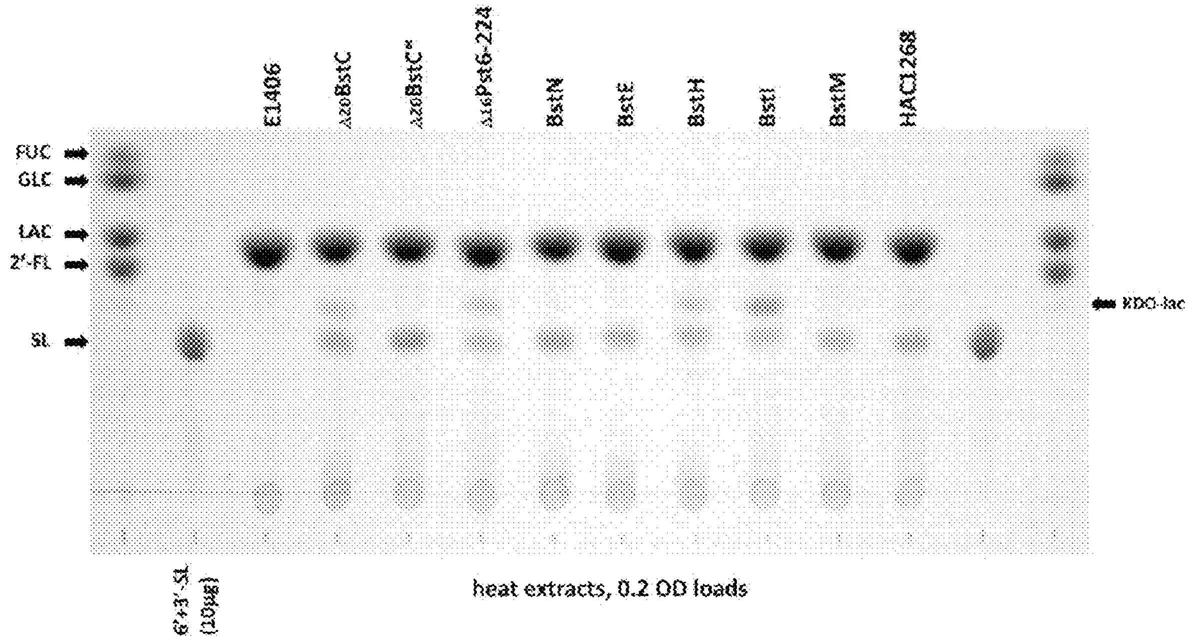
FIG. 5 is an image of a thin layer chromatography result. Prominent spots corresponding to the intracellular lactose pool are seen in the control strain (E1406, which does not contain and bst+neuBCA expression plasmid) and also in all bst candidate cultures.

Tubes were inoculated to 0.1 $OD_{600}$/mL with strains comprising E1406 transformed with individual candidate bst+neuBCA expression plasmids, and were then incubated at 30° C. for 120 minutes with continuous aeration on a roller drum. Tryptophan was then added to the cultures to a concentration of 200 μg/mL to induce bst gene and neuBCA operon expression, along with the addition of lactose as the acceptor sugar to a concentration of 1% w/v. The culture was left at 30° C. with roller drum aeration for a further 22 h. At the end of this period 20 $OD_{600}$ of cells from each culture were pelleted by centrifugation (14,000×g, 1 min), re-suspended in 200 μl of water and heated to 98° C. for 10 min to release cytoplasmic sugars. After clearing the suspension by centrifugation, 2 μl aliquots were applied to 10×20 cm aluminum-backed silica thin layer chromatography plates (Machery-Nagel #818163). Chromatograms were developed in n-butanol/acetic acid/water (2:1:1), and visualized by heating after spraying with 3% w/v α-napthol in 12% $H_2SO_4$/80% ethanol/8% water. FIG. 5 shows the result.

Prominent spots corresponding to the intracellular lactose pool were seen in the control strain (E1406, that does not contain an bst+neuBCA expression plasmid) and also in all bst candidate cultures. The E1406 control showed no spot corresponding to sialyllactose, whereas all other cultures displayed a spot co-migrating with a sialyllactose standard that comprised a mixture of 6'-SL and 3'-SL (these species do not resolve from each other in this TLC system). Not shown are cultures expressing candidate genes bstD and bstJ. Neither of these produced any detectable sialyllactose, and thus these genes most probably represent "false positive hits" in the database screen.

Figure 6A:
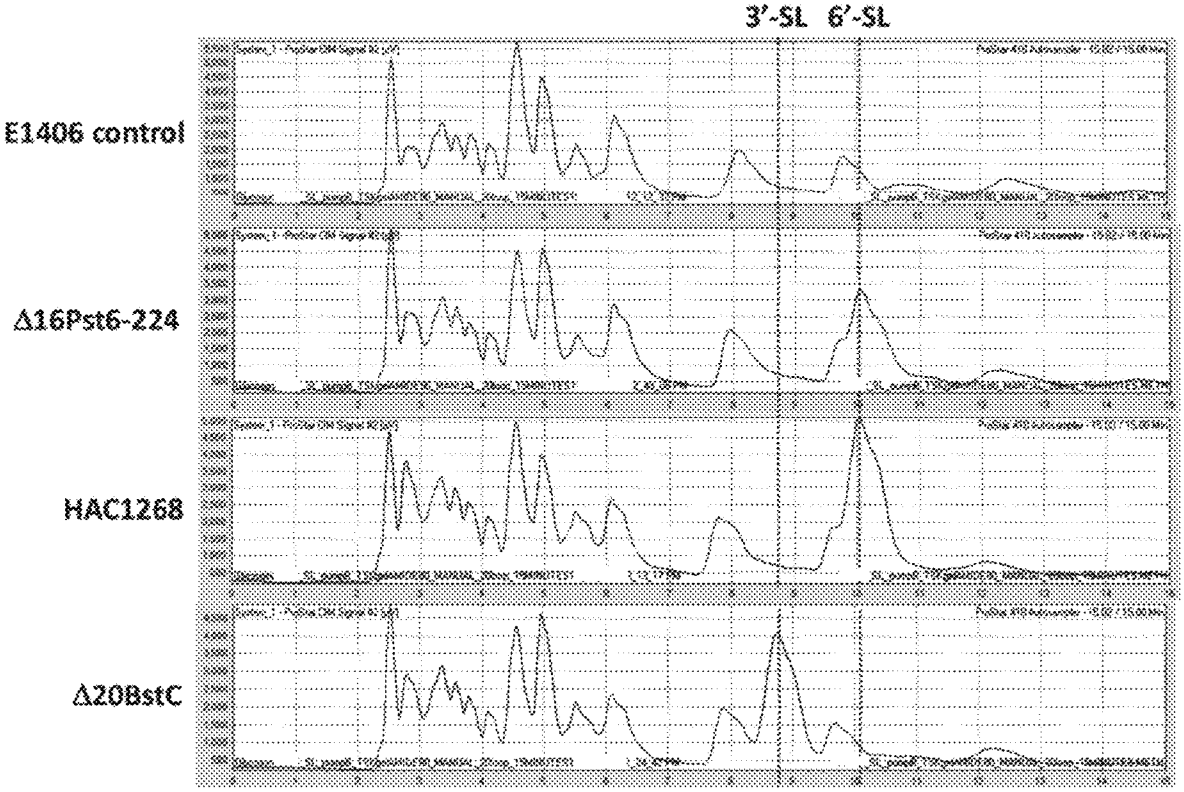
FIGS. 6A, 6B, and 6C are images showing UV traces from HPLC runs for the various heat extracts (E1406 control Δ16Pst60224, HAC1268, Δ20BstC, Δ20stC*, BstE, BstH, BstI, BstM, and BstN).
Figure 6B:
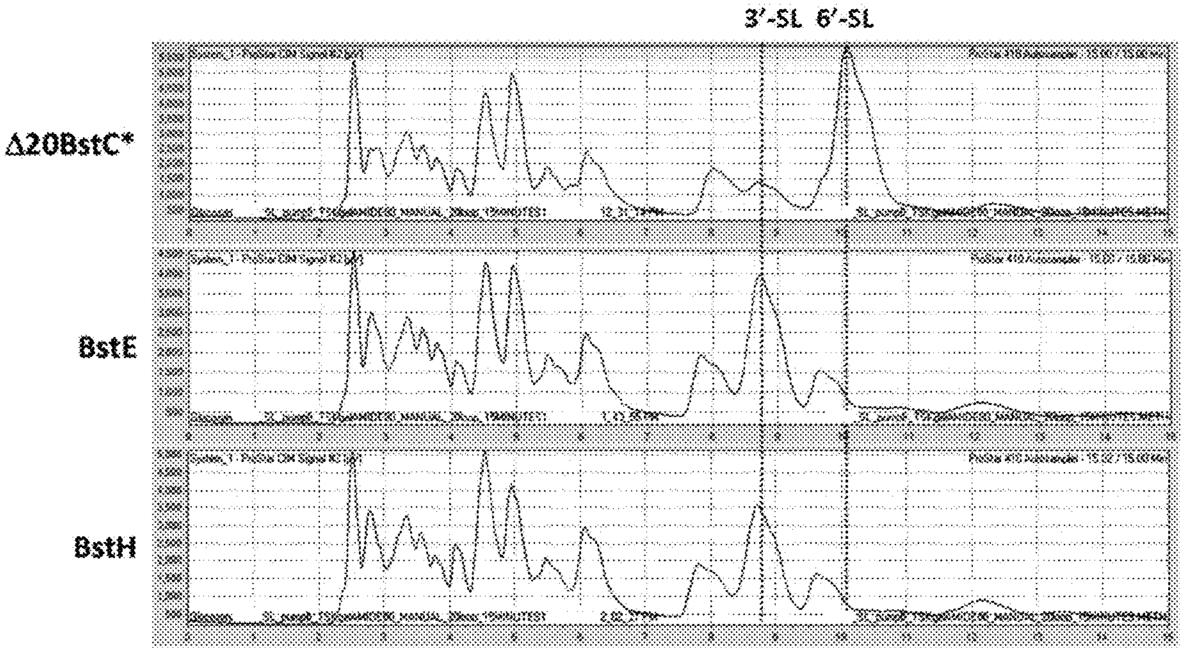
Figure 6C:
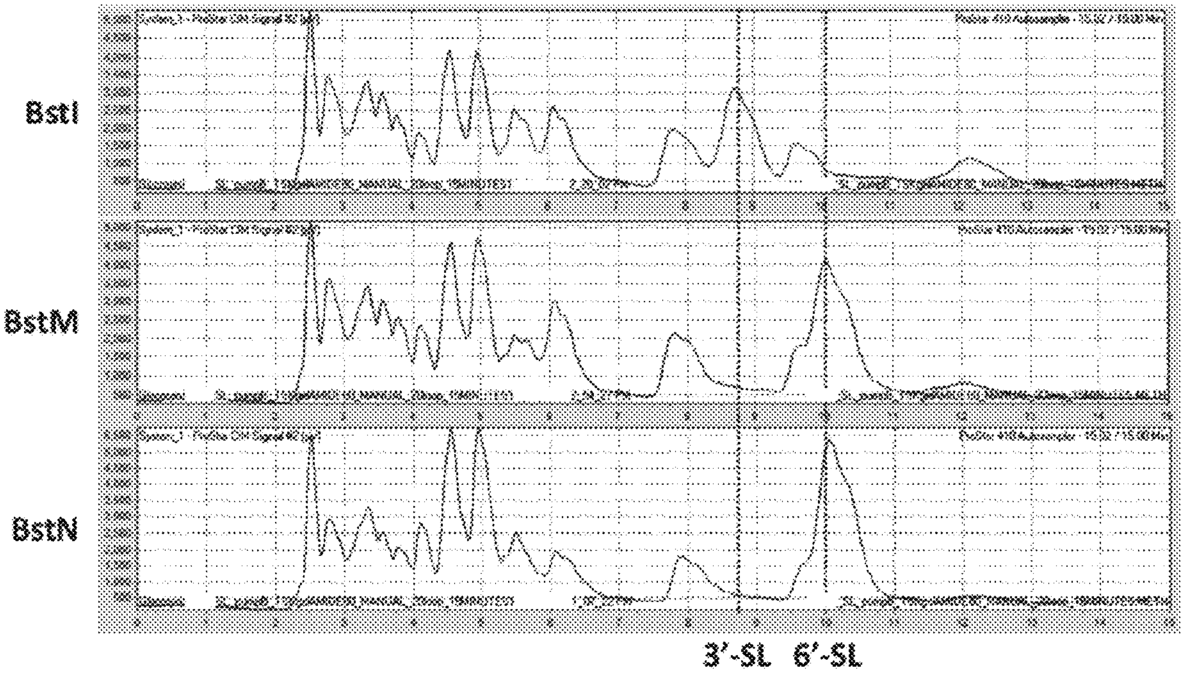

Of note in FIG. 5 is a spot running above sialyllactose in several of the candidates. This spot corresponds to KDO-lactose, and results from a linkage of the *E. coli* lipopolysaccharide precursor, 2-keto-3-deoxyoctulosonic acid (KDO) with lactose, as a result of relaxed substrate specificity exhibited by individual bst enzymes that utilize the endogenous *E. coli* pool of CMP-KDO as an alternative to the engineered pool of CMP-Neu5Ac as described herein. As can be seen in FIG. 5, Pst6-224 (as expected from the literature, Drouillard, S., et al. (2010). Carbohydr Res 345, 1394-99) generated the unwanted KDO-lactose product. However several of the bst candidates produced little if any KDO-lactose under the same culture conditions (e.g. BstE, BstM, BstN), highlighting the utility of these enzymes for the production of purer preparations of sialyl-oligosaccharides Identification of the Sialyl-Acceptor Sugar Bond Specificity Characterization and Identification Via HPLC ST enzymes Pst6-224 and HAC1268, whose amino acid sequences were used as probes for the database screens, have been previously characterized biochemically and are known to be α2,6 sialyltransferases (Drouillard, S., et al. (2010). Carbohydr Res 345, 1394-99, Schur, M. J., et al. (2012). Glycobiology 22, 997-1006). However the sialyl-acceptor sugar bond specificity (i.e. α(2,3)- or α(2,6)-) of the candidate bst enzymes of the present invention were unknown. To discover their sialyl-acceptor sugar bond specificity the same cytoplasmic extracts analyzed by TLC above (FIG. 5) were also analyzed utilizing a HPLC system capable of resolving 6'-SL from 3'-SL. The heat extract samples (described above) were made 15 mM in potassium phosphate (pH 4) and 60% in acetonitrile. They were then applied to a TSKgel Amide-80 column (5 μm particle size, 4.6×250 mm) and eluted under isocratic conditions of 67% acetonitrile/15 mM potassium phosphate, pH4.0, 1 mL/min, 60° C., with UV detection at 210 nm. FIGS. 6A, 6B, and 6C show UV traces from HPLC runs for the various heat extracts. In this system 3'-SL eluted at ~8.8 minutes, whereas 6'-SL eluted at ~10.1 minutes. Data is presented in Table 3.

TABLE 3

Summary of the discovered sialyl-acceptor sugar bond specificity of the new bst enzymes

| Gene name | Organism | Accession number | GT family | Sialyltransferase activity | SEQ ID # |
|---|---|---|---|---|---|
| Pst6-224 | *Photobacterium* sp. JT-ISH-224 | BAF92026.1 | GT80 | α(2,6) sialyltransferase | 1 |
| BstC | *Avibacterium paragallinarum* | WP_021724759.1 | putative GT80 | α(2,3) sialyltransferase | 2 |
| BstC* | *Avibacterium paragallinarum* | WP_021724759.1 | putative GT80 | α(2,6) + α(2,3) sialyltransferase | 15 |
| BstD | *Actinobacillus ureae* | WP_005625206.1 | n/a | unknown/ not an ST | 3 |
| BstE | *Haemophilus_ ducreyi* | AAP95068.1 | putative GT80 | α(2,3) sialyltransferase | 4 |
| BstH | *Alistipes* (multispecies) | WP_018695526.1 | putative GT80 | α(2,3) sialyltransferase | 5 |
| BstI | *Bibersteinia trealosi* | AGH37861.1 | putative GT80 | α(2,3) sialyltransferase | 6 |
| BstJ | *Shewanella piezotolerans* | YP_002314261.1 | n/a | unknown/ not an ST | 7 |
| HAC1268 | *Helicobacter acinonychis* | CAK00018.1 | GT42 | α(2,6) sialyltransferase | 8 |
| BstM | *Helicobacter pylori* | WP_000743106.1 | putative GT42 | α(2,6) sialyltransferase | 9 |
| BstN | *Helicobacter cetorum* | WP_014661583.1 | putative GT42 | α(2,6) sialyltransferase | 10 |

Characterization and Identification Via NMR

A secondary confirmation was sought through NMR (nuclear magnetic resonance) spectroscopy, for the structure of SL (6'-SL) produced utilizing the BstM and BstN enzymes.

Large Scale Production of SL

To this end, and to produce sufficient SL for the analyses, 2 L fermentation runs were performed on derivatives of strain E1406 harboring either BstM or BstN expression plasmids (i.e. pG549, SEQ ID NO: 12 or pG543, SEQ ID NO: 11) respectively. Strains were grown in Ferm 4a mineral medium to early exponential phase to produce a seed culture.

Composition of Ferm 4a Media Has the Following (Per Liter)

4 g $(NH_4)_2HPO_4$
10 g $KH_2PO_4$
0.25 g $MgSO_4.7H_2O$
0.4 g NaOH
17 g glucose
(adjusted to pH6.8 with additional NaOH if required)

A portion of this seed culture was then inoculated into a 2 L bioreactor containing 900 mL of the same medium (but containing an additional 0.75 g/L $MgSO_4.7H_2O$, 1 mL of DF204 antifoam, and 10 mL of trace metals solution).

Trace Metals Solution Has the Following (Per Liter):

13.4 g NTA (nitrilotriacetic acid)
5 g $FeSO_4.7H_2O$
0.85 g $MnCl_2.4H_2O$
0.9 g $ZnSO_4.7H_2O$
0.14 g $CoCl_2.6H_2O$
0.085 g $CuCl_2.2H_2O$
0.17 g $H_3BO_3$
0.09 g $Na_2MoO_4.2H_2O$ The optical density of cells in the fermenter vessel after inoculation was 0.006 at 600 nm ($OD_{600}$)

Strains were grown in the fermenter in batch mode at 30° C. with pH control to pH 6.8 (adjusted automatically with additions of 7.4M $NH_4OH$) for approximately 16 h, at which point glucose exhaustion occurred as indicated by an increase in dissolved oxygen levels and a decrease in agitation speed. A fed-batch continuous glucose feeding regimen was then initiated (9.1 g of a 50% w/v glucose feed solution/h) such that the culture was maintained under carbon-limitation. After 2 h a bolus of 45.5 g of a 11.4% w/v lactose solution was added, and a continuous lactose feed of 2.2 g/h of the same solution was initiated. Simultaneously a bolus of 41.2 g of a 2% w/v tryptophan solution was added to initiate bst expression. This bolus was repeated 2 more times at 24 h intervals during the ensuing fed-batch fermentation phase. which continued for a further 70 hours, during which 50% saturation of dissolved oxygen was maintained using an agitation to air enrichment cascade with initial 0.18 standard liter per minute aeration. Optical density was ~120 $OD_{600}$ at the end of fermentation. At harvest, whole fermentation broth was adjusted to 80 mM $CaCl_2$ by the addition of a 1M $CaCl_2$ stock solution, and after standing overnight at 4° C. was clarified by centrifugation at 4,000×g for 1 h.

NMR Analysis

A portion of the clarified culture supernatant was then used for purification of sialyllactose samples for NMR analysis using the following protocol:

1. Cations were removed (and proteins precipitated) by addition of solid Amberlite IR120 [H+ form] to the clarified $CaCl_2$-treated broth to reach pH 2.
2. The treated supernatant was clarified by centrifugation. Strong acids were subsequently removed by addition of Dowex 66 resin [free-base form] until pH 6 was reached. Clarified by centrifugation again.
3. Loaded onto a Dowex 1×4, 200-400 mesh column [$HCO_3^-$ form]. SL binds to this column.
4. The column washed with water.
5. SL was eluted from the column with 0.1M $NaHCO_3$
6. $Na^+$ was removed from the sialyllactose eluate by adding Amberlite IR120 [H+ form] to reach pH 3.
7. The SL solution was adjusted to pH to 6 with NaOH, rotary evaporated, then lyophilized to dryness.

Figure 7:
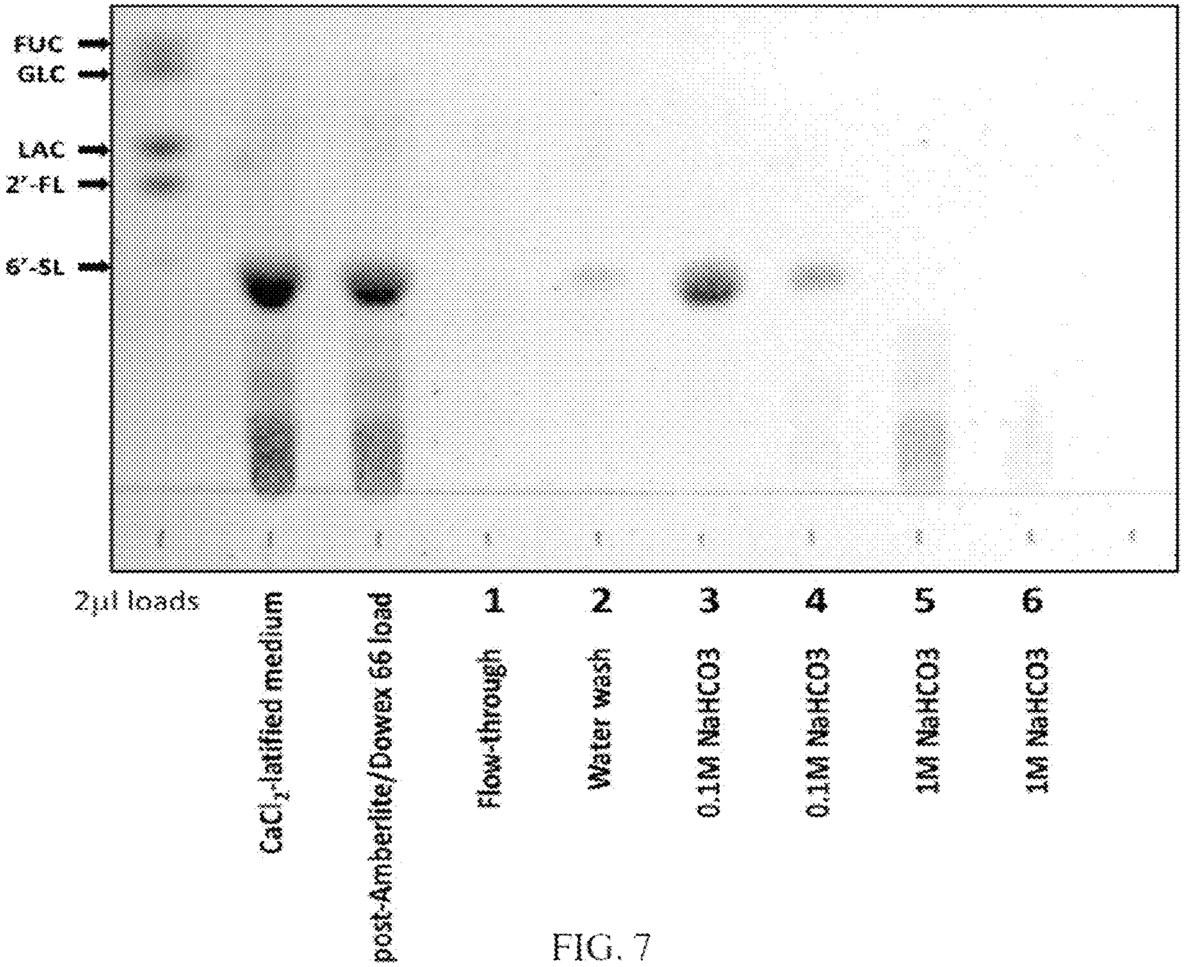
FIG. 7 is an image of thin layer chromatography of fractions from the Dowex 1×4 column. Typically, fraction 3 was the purest fraction and, after desalting, was suitable for NMR analysis.

FIG. 7 shows a typical thin layer chromatogram of fractions from the Dowex 1×4 column. Typically fraction 3 was the purest fraction and, after desalting, was suitable for NMR analysis.

Figure 8:
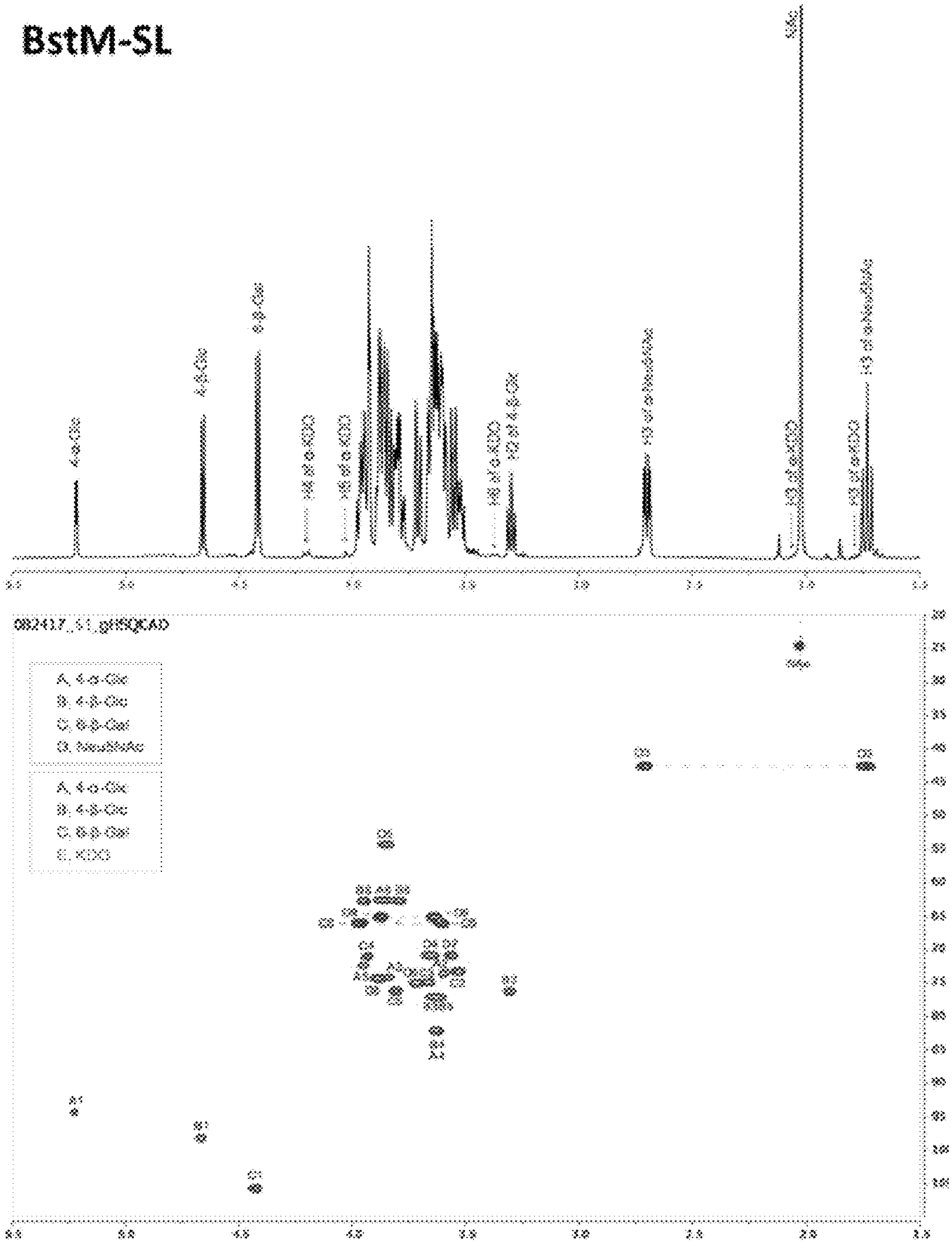
FIG. 8 is a 1D $^1$H NMR spectrum of SL samples produced by BstM (BstM-SL) which showed three anomeric signals: δ 5.22. (A), δ 4.66 (B), both attributed to a reducing-end Glcp, and δ 4.42 (C) assigned to β-Galp residue.
Figure 9:
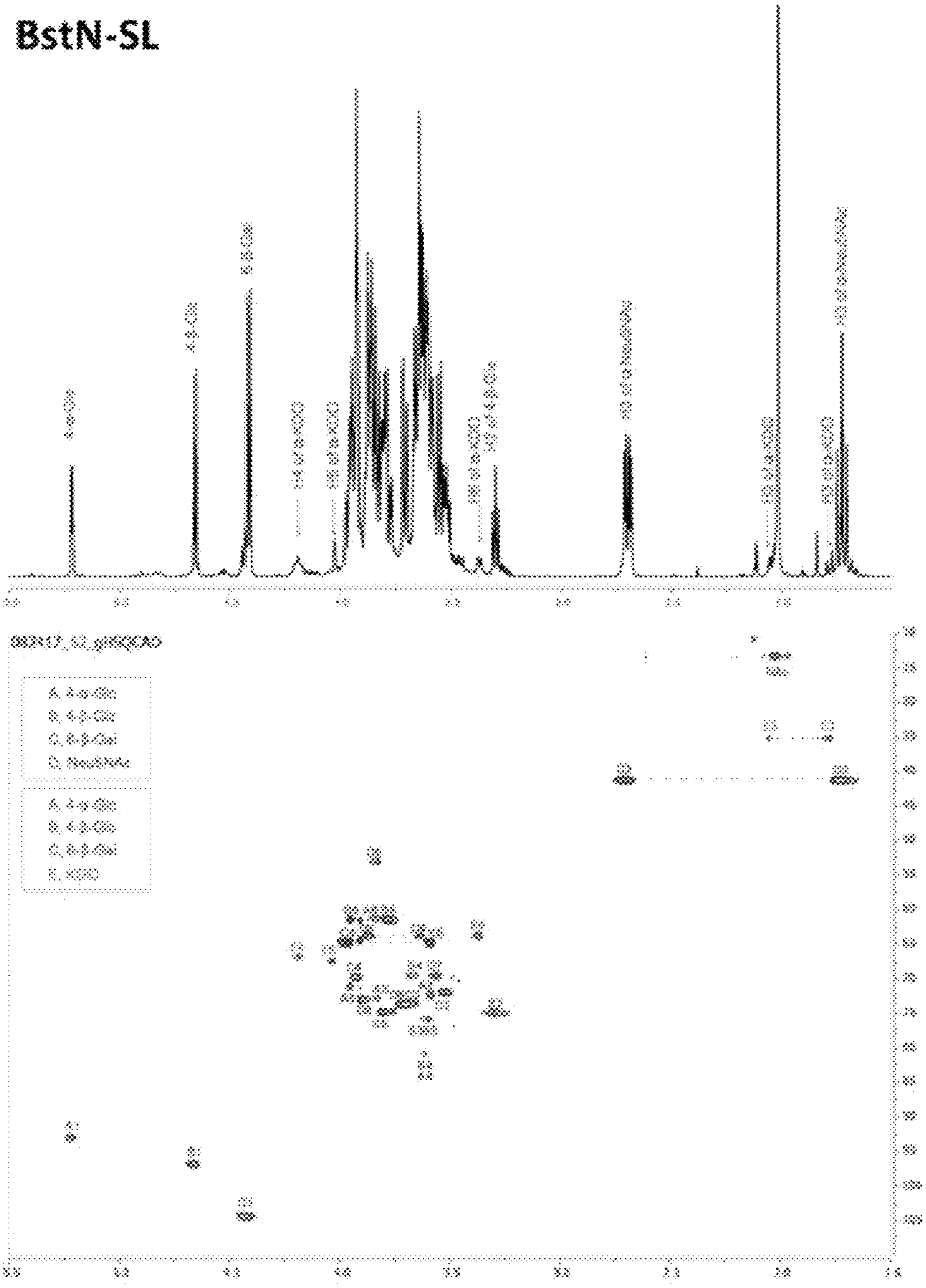
FIG. 9 is a 1D $^1$H NMR spectrum of SL samples produced by BstN (BstN-SL) which showed three anomeric signals: δ 5.22 (A), δ 4.66 (B), both attributed to a reducing-end Glcp, and δ 4.42 (C) assigned to β-Galp residue.

The 1D $^1H$ NMR spectrum of SL samples produced by BstM (BstM-SL) and BstN (BstN-SL), (FIG. 8 and FIG. 9 respectively), showed three anomeric signals: δ 5.22 (A), δ 4.66 (B), both attributed to a reducing-end Glcp, and δ 4.42 (C) assigned to β-Galp residue (Table 4). In the heteronuclear multiple bond correlation (HMBC) spectrum, a cross peak observed at $\delta_H$ 4.42/$\delta_C$ 80.8 indicated that β-Galp (C) is linked to the 4-position of reducing-end Glcp (A, B). In the heteronuclear single quantum coherence (HSQC) spectrum, a downfield shift observed for C-6 (δ 64.7) of β-Galp indicated that residue C is 6-substituted. In the HMBC spectrum, cross peaks observed at $\delta_H$ 3.59, 3.96/$\delta_C$ 101.5 (between H-6 of β-Gal and C-2 of α-Neu5NAc), indicated that terminal α-Neu5NAc (D) is linked to 6-position of β-Gal (C).

TABLE 4

Chemical shifts assignments of 6'-sialyllactose and 6'KDOlactose

| | Glycosyl Residue | Nuclei | 1 | 2 | 3 | 4 | 5 | 6 | 7 | 8 | 9 | 5-NAc $CH_3COO$ |
|---|---|---|---|---|---|---|---|---|---|---|---|---|
| A | 4-α-Glc | $^1H$ | 5.22 | 3.60 | 3.83 | 3.62 | 3.95 | 3.88/ | | | | |
| | | | (J = 3.7) | | | | | 3.80 | | | | |
| | | $^{13}C$ | 93.0 | 72.2 | 72.8 | 80.8 | 71.2 | 61.2 | | | | |
| B | 4-β-Glc | $^1H$ | 4.66 | 3.29 | 3.64 | 3.63 | 3.60 | 3.95/ | | | | |
| | | | (J = 8) | | | | | 3.77 | | | | |
| | | $^{13}C$ | 96.8 | 74.8 | 75.8 | 80.8 | 75.9 | 61.5 | | | | |
| C | 6-β-Gal | $^1H$ | 4.42 | 3.53 | 3.71 | 3.92 | 3.79 | 3.96/ | | | | |
| | | | (J = 8) | | | | | | | | | |
| | | $^{13}C$ | 104.3 | 72.1 | 73.6 | 69.8 | 74.9 | 64.7 | | | | |
| D | α-Neu5NAc | $^1H$ | — | — | 2.71/ | 3.66 | 3.84 | 3.66 | 3.55 | 3.88 | 3.87/ | 2.02 |
| | | | (J = 8) | | 1.74 | | | | | | 3.63 | |
| | | $^{13}C$ | 174.6 | 101.5 | 41.3 | 69.5 | 54.8 | 73.4 | 69.6 | 73.1 | 63.8 | 23.2/ |
| | | | | | | | | | | | | 176.0 |
| E | α-KDO | $^1H$ | — | — | 2.05/ | 4.19 | 4.03 | 3.37 | | | | |
| | | | | | 1.78 | | | | | | | |
| | | $^{13}C$ | 176.4 | 101.5 | 35.2 | 66.9 | 67.4 | 63.8 | | | | |

Taking into account 2D NMR data, the major compound present in both samples was 6'-sialyllactose. Minor levels of KDO-lactose were also found in both samples.

Enzyme Engineering to Alter the Regioselectivity of BstC and BstE From α(2,3)- to α(2,6)-Selective Several of the bst candidates that were selected and tested from the screen were α(2,3)-selective rather than α(2,6)-selective, including enzymes BstC, BstE, BstH and BstI. Enzyme engineering strategies to alter the regioselectivity of BstC and BstE from α(2,3)- to α(2,6)-selective were explored (Schmölzer, K., et al. (2015). Chem Commun (Camb) 51, 3083-86; Schmölzer, K., et al. (2013). Glycobiology 23, 1293-1304). A sialyltransferase from *Pasteurella dagmatis*, (PdST, accession #WP005762792.1, SEQ ID NO: 13) was shown to exhibit α(2,3)-selective activity when purified and used in vitro to catalyze SL formation from lactose and CMP-Neu5Ac precursors (Schmölzer, K., et al. (2015). Chem Commun (Camb) 51, 3083-86). A subsequent study from the same group demonstrated that structure-guided substitution of specific amino acids within the acceptor binding site of PdST completely switched the enzyme's regioselectivity from α(2,3)-selective to α(2,6)-selective. Specifically, double mutations of P7H and M117A in the PdST sequence had the effect of converting PdST from an α(2,3)-selective ST to a α(2,6)-selective ST in vitro (Schmölzer, K., et al. (2013). Glycobiology 23, 1293-1304).

Figure 10:
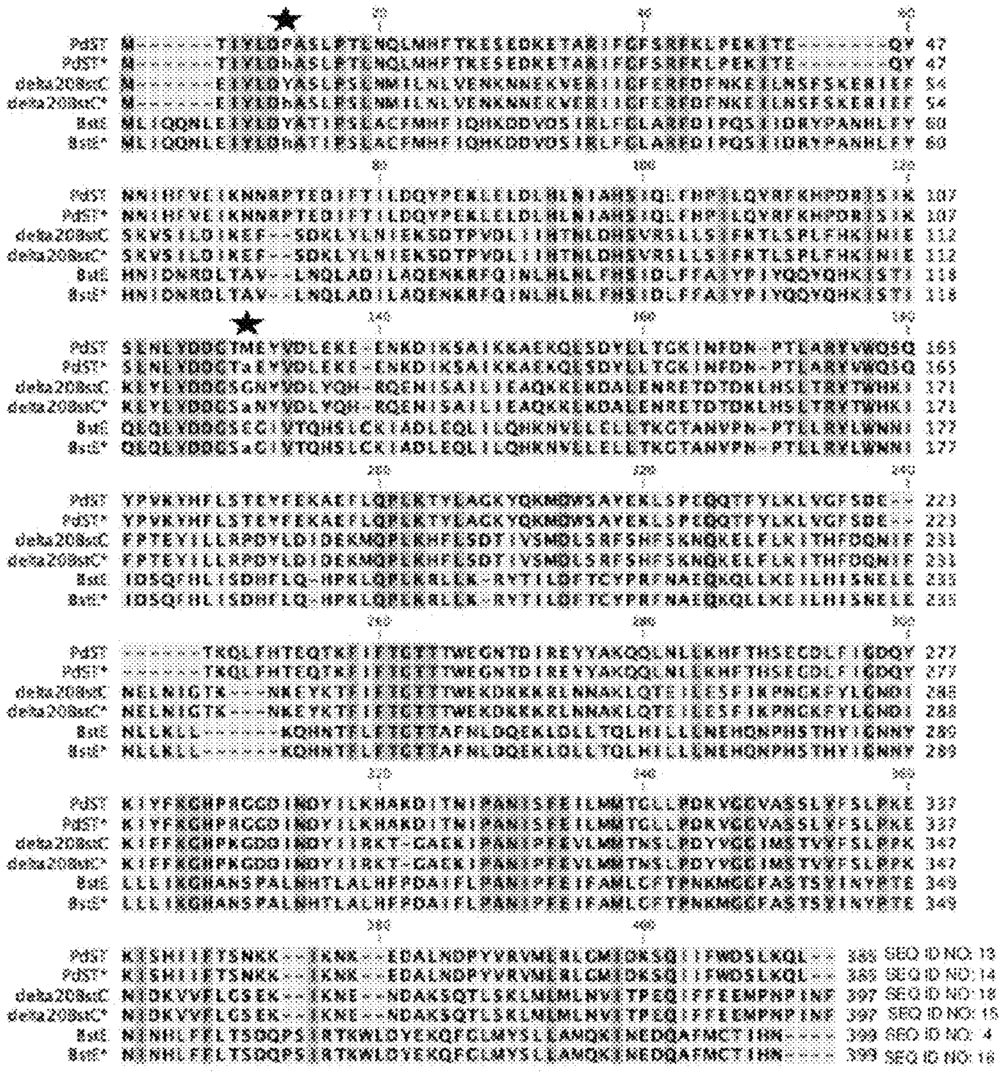
FIG. 10 is an image showing a sequence alignment of wild type PdST, Δ20BstC and BstE α(2,3) sialyltransferases.

Without being bound by any scientific theory, structurally equivalent mutations introduced into the acceptor binding site of the bst enzymes herein may produce a similar switch in regioselectivity. Two candidates, Δ20BstC and BstE, were selected to explore the approach. To this end, a Δ20bstC and bstE synthetic genes incorporating the appropriate codon changes (hereafter referred to a Δ20bstC* and bstE* were synthesized in vitro by the Gibson Assembly method from gBlock oligonucleotides, and cloned by standard molecular biological techniques into *E. coli* expression plasmids. FIG. 10 is an alignment of wild type PdST, Δ20BstC and BstE Δα(2,3) sialyltransferases. Also shown in the alignment are mutant forms of the three enzymes, named PdST* (SEQ ID NO: 14, the published mutant known be switched in regioselectivity from α(2,3) to α(2,6)), Δ20BstC* (SEQ ID NO: 15) and BstE* (SEQ ID NO: 16), mutants designed and tested herein. Mutated regions are indicated in the alignment by black stars and the mutated residues are shown in lower case. Specifically, the amino acid substitutions Y7H and G122A were introduced into the Δ20BstC sequence to generate Δ20BstC* while Y13H and E128A were introduced to the BstE sequence to generate BstE*.

Δ20bstC* (pG544, SEQ ID NO: 17) and bstE* expression plasmids were transformed into the engineered *E. coli* production host. Strains were grown in IMC media to early exponential phase at 30° C. before tryptophan (200 mg/mL) and lactose (1%) were simultaneously added to initiate SL biosynthesis. At the end of the synthesis period (24 h), equivalent $OD_{600}$ units of each strain were harvested, and cell lysates were prepared by heating for 10 minutes at 98° C. and centrifugation to release intracellular SL. Lysates containing synthesized SL were then treated with sialidase S (specific for α(2,3) linked Neu5Ac) or sialidase C (acts on both α(2,3) or α(2,6) linked Neu5Ac) to analyze whether engineered Δ20BstC* or BstE* were capable of catalyzing synthesis of 6'-SL rather than 3'-SL.

Figure 11:
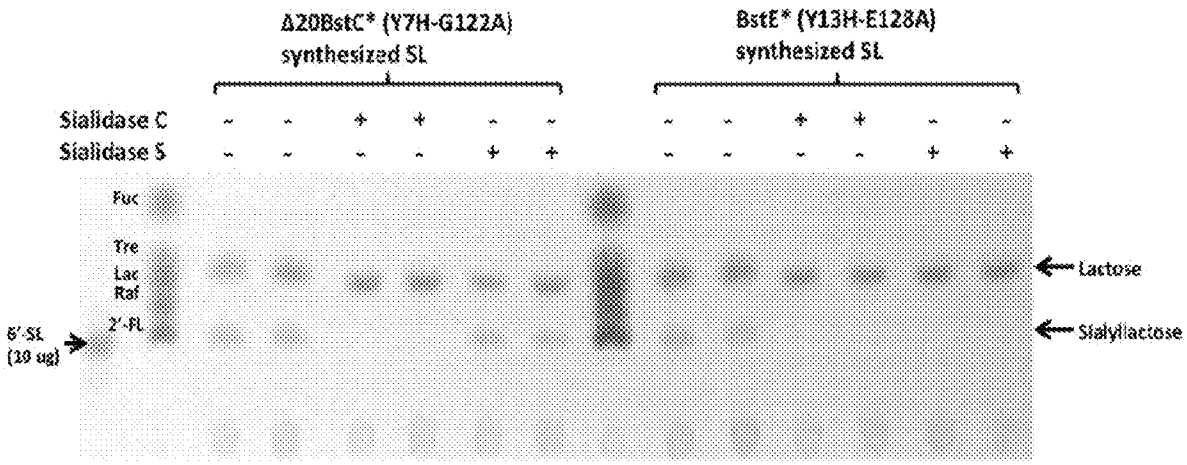
FIG. 11 is an image of thin layer chromatography showing that SL synthesized by BstE*-producing cells was efficiently converted to lactose by both sialidase S and sialidase C. This result indicated that BstE* still possessed exclusively α(2,3)-selective activity, and that the introduced mutations did not alter regioselectivity of the enzyme as was predicted.

As shown in FIG. 11, SL synthesized by BstE*-producing cells was efficiently converted to lactose by both sialidase S and sialidase C. This result indicates that bstE* still possessed exclusively α(2,3)-selective activity, and that the introduced mutations did not alter regioselectivity of the enzyme as was predicted. However in stark contrast, SL synthesized by Δ20BstC* remained susceptible to digestion with sialidase C but appeared largely resistant to treatment with sialidase S. This result demonstrates the regioselectivity of Δ20BstC* had been successfully altered from α(2,3) to α(2,6), and that the engineered enzyme primarily catalyzed 6'-SL synthesis rather than 3'-SL synthesis in the production strain.

Figure 12:
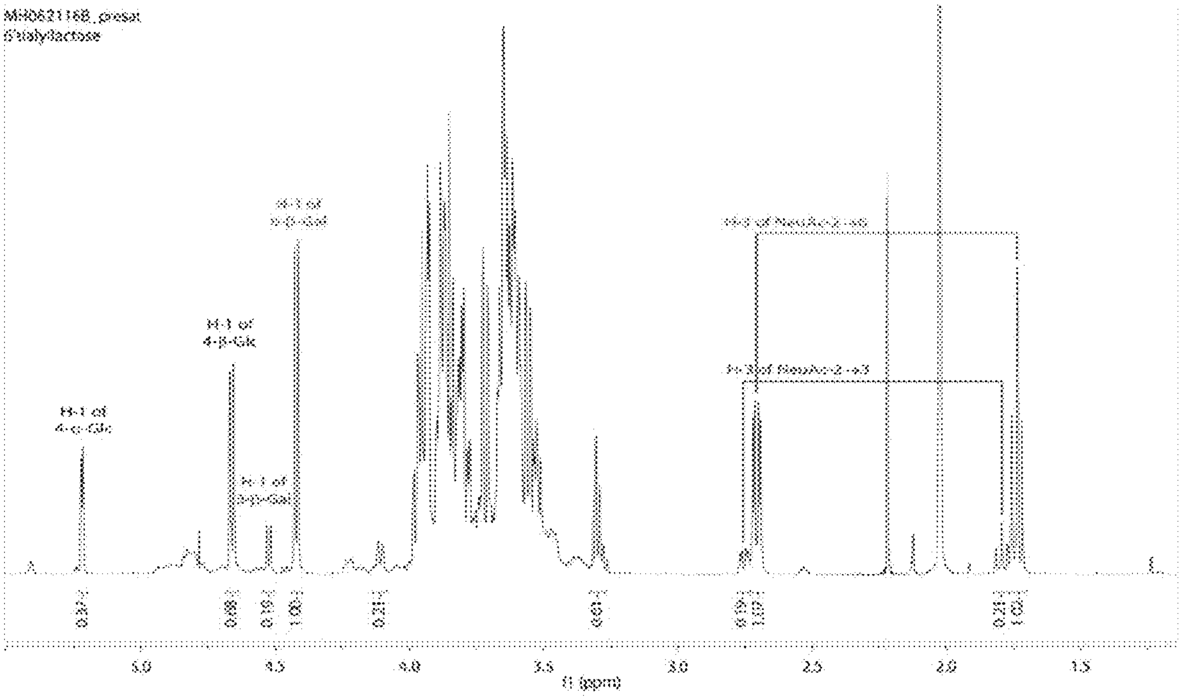
FIG. 12 is a 1D $^1$H NMR spectrum of SL produced by Δ20BstC*. Characteristic features of the spectrum were 4 distinct anomeric peaks and the up-field signals of axial and equatorial H-3 of sialic acid.
Figure 13:
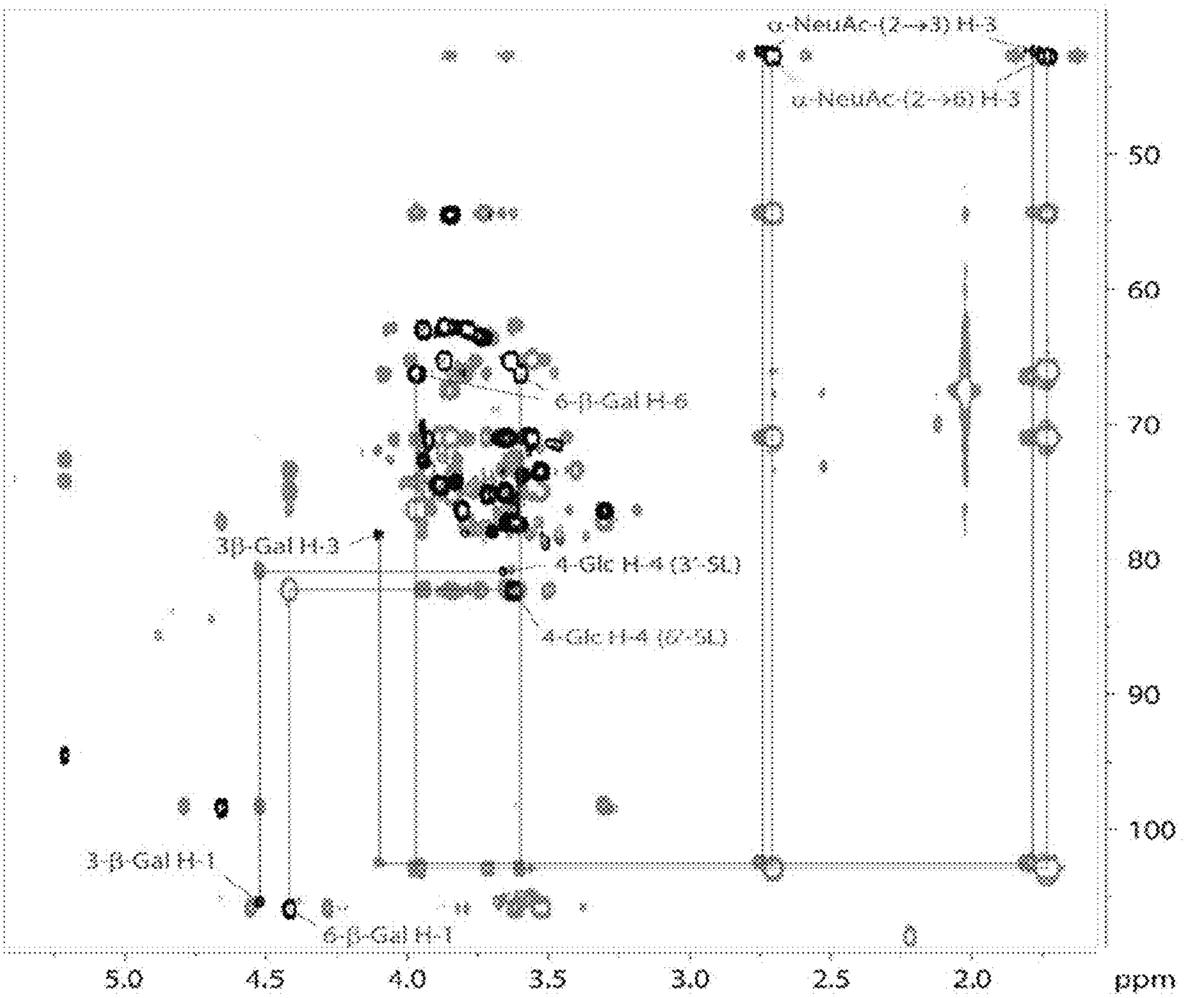
FIG. 13 is an image of overlaid HSQC and HMBC NMR spectra of sialyllactose synthesized by ΔBstC*-producing cells. NMR analysis showed that the larger signals belonged to 6'-sialyllactose, whereas the smaller one was part of contaminating 3-sialyllactose.

SL synthesized by the Δ20BstC* expressing strain was then purified and subjected to NMR spectroscopy to confirm its identity and purity. FIG. 12 shows the 1D-proton NMR spectrum of SL produced by Δ20BstC*. Characteristic features of the spectrum were 4 distinct anomeric peaks and the up-field signals of axial and equatorial H-3 of sialic acid. The latter consisted of two pairs of distinct signals in a ratio of about 5:1. Extensive 2-D NMR analysis (FIG. 13) showed that the larger signals belong to 6'-sialyllactose, whereas the smaller one was part of contaminating 3'-sialyllactose. The chemical shift assignment of these two components is listed in Table 5. The analysis revealed that the SL synthesized by Δ20BstC* was comprised of a mixture of 84% 6'-SL and 16% 3'-SL. Therefore, introduction of the Y7H-G122A mutations into the Δ20BstC* acceptor binding site strongly biased the regioselectivity of the enzyme towards forming α(2,6) Neu5Ac linkages and enabled strains producing Δ20BstC* to synthesize primarily 6'-SL rather than 3'-SL.

Surprisingly the engineered Δ20BstC* mutant protein generates much less KDO-lactose when used to produce sialyllactose in *E. coli* than does its wild-type parent, Δ20BstC (see FIG. 5). The active site mutations Y7H and G122A introduced into Δ20BstC to generate Δ20BstC* result not only in a switch of regiospecificity from α(2,3) to α(2,6), but also reduce the ability of the enzyme to utilize CMP-KDO as a substrate, thus leading to a purer sialyllactose product profile.

Enzyme Engineering to Further Improve the α(2,6)-Regioselectivity of Δ20BstC*

To improve upon the regioselectivity of the new enzyme variant Δ20BstC*, further enzyme engineering strategies were explored (Guo, Y, et al (2015) Enzyme and Microbial Technology 78, 54-62; McArthur, B. et al. (2017) Organic & Biomolecular Chemistry 15, 1700-1709). A double mutant P34H/M144L of a sialyltransferase from *Pasteurella multocida* (PmST1, accession #AAY89061) was found to increase the enzyme's regioselectivity from 3.9% to 98.7% α(2,6)-selective. Structurally equivalent amino acid substitutions at position 122 of the amino acid sequence of Δ20BstC* would improve the enzyme's α(2,6)-regioselectivity. Specifically, the amino acid substitutions A122V, A122L, A122M and A122F were introduced to Δ20BstC* to generate Δ20BstC*2 (SEQ ID NO: 27) Δ20BstC*3 (SEQ ID NO: 28), Δ20BstC*4 (SEQ ID NO: 29) and Δ20BstC*5 (SEQ ID NO: 30), respectively.

Δ20BstC*2, Δ20BstC*3, Δ20BstC*4 and Δ20BstC*5 expression plasmids were transformed into engineered *E. coli* production host. Strains were grown in Ferm 4a media to early exponential phase at 30° C. before tryptophan (200 mg/mL) and lactose (1%) were simultaneously added to initiate SL biosynthesis. At the end of the synthesis period (24 h), equivalent $OD_{600}$ units of each strain were harvested, and cell lysates were prepared by heating for 10 minutes at 98° C. and centrifugation to release intracellular SL. TLC analysis of the heat extracts showed SL synthesis, and also showed similarly reduced or negligible amounts of KDO-lactose production as was seen for Δ20BstC*, which was in contrast to the level of KDO-lactose synthesis that had been observed for the native wild-type enzyme Δ20BstC (FIG. 5).

To determine 6'SL to 3'SL ratios, the various mutant Δ20BstC* strains were harvested and extracted using 5 mM potassium phosphate (pH 4.0) in 70% acetonitrile and analyzed utilizing a HPLC system capable of resolving 6'-SL from 3'-SL. The extracted samples (described above) were applied to a TSKgel Amide-80 column (5 μm particle size, 4.6×250 mm) and eluted under isocratic conditions of 5 mM potassium phosphate (pH 4.0) in 70% acetonitrile, 1 mL/min, at room temperature with UV detection at 210 nm.

Figure 16:
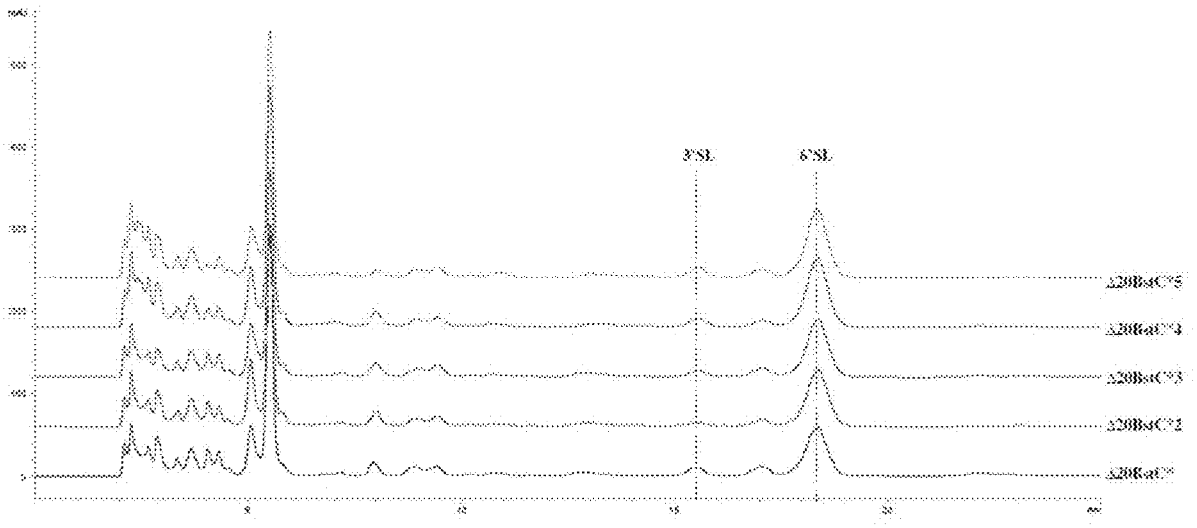
FIG. 16 is an image showing UV traces from HPLC runs for the various cell extracts (Δ20BstC*, Δ20BstC*2, Δ20BstC*3, Δ20BstC*4, Δ20BstC*5).

FIG. 16 shows exemplary HPLC for the various extracts. In this system, 3'SL eluted at about 15.5 minutes, whereas 6'SL eluted at about 18.3 minutes. Data is presented in Table 5. The analysis revealed that the mutations A122F, A122M, A122L, and A122V resulted in about 2%, 4%, 6% and 8% increase, respectively, in α(2,6)-regioselectivity compared to Δ20BstC*.

TABLE 5 shows HPLC analysis of regioselectivity of Δ20BstC* mutants.

| Sample | Mutation | Peak Area (mAu•min) 3'SL | 6'SL | % 6'SL |
|---|---|---|---|---|
| Δ20BstC* | — | 353.9 | 2260.8 | 86.5 |
| Δ20BstC*2 | A122V | 163.4 | 2608.6 | 94.1 |
| Δ20BstC*3 | A122L | 221.8 | 2585.9 | 92.1 |
| Δ20BstC*4 | A122M | 336.6 | 3150.6 | 90.3 |
| Δ20BstC*5 | A122F | 393.8 | 3096.3 | 88.7 |

Sialyltransferases For Use in the Production of Sialylated Oligosaccharides

In summary, wild-type Δ20BstC is a lactose utilizing α(2,3) sialyltransferase that produced 3'-SL in the engineered *E. coli* strain described herein. This enzyme was engineered by introducing two specific active site mutations each, to generate new enzyme variants with altered regio-specificity: Δ20BstC*, Δ20BstC*2, Δ20BstC*3, Δ20BstC*4 and Δ20BstC*5, that synthesize an 85:15, 94:6, 92:8, 90:10, and 89:9 mixture of 6'-SL:3'-SL, respectively. These enzyme variants enabled the production of two of the major sialylated hMOS from human milk (Bao, Y., Zhu, L, and Newburg, D. S. (2007) Anal Biochem 370, 206-214) in predictable ratios, while possessing an ability to generate reduced amounts of KDO-lactose. The ability to produce two sialyllactose species within the course of a single biofermentation, may offer significant advantages in terms of time and cost of production over two separate fermentations.

What is claimed is:

1. A method for producing a sialylated oligosaccharide in a bacterium comprising providing a bacterium comprising an exogenous lactose-utilizing sialyltransferase enzyme, wherein the enzyme comprises an amino acid sequence having at least 90% identity to the amino acid sequence of SEQ ID NO:27 having sialyltransferase activity.

2. The method of claim 1, wherein the amino acid sequence of the enzyme is less than 100% identical to the amino acid sequence of SEQ ID NO:27, SEQ ID NO: 18, or SEQ ID NO: 15.

3. The method of claim 1, wherein the enzyme comprises no deletions or insertions compared to the amino acid sequence of SEQ ID NO: 27, SEQ ID NO: 18, or SEQ ID NO: 15.

4. The method of claim 3, wherein the difference between the amino acid sequence of the enzyme and the amino acid sequence of SEQ ID NO: 27, SEQ ID NO: 18, or SEQ ID NO: 15 consists of one or more conservative amino acid substitutions.

5. The method of claim 1, wherein the naturally occurring enzyme is a bacterial GT80 family sialyltransferase.

6. The method of claim 5, wherein the bacterial GT80 family sialyltransferase comprises the GT-B structural fold.

7. The method of claim 1, wherein the enzyme is produced by a microbial organism.

8. The method of claim 7, wherein the microbial organism is a bacterium that is naturally present in the gastrointestinal tract of a mammal.

9. The method of claim 8, wherein the microbial organism is a bacterium within the genus *Photobacterium, Avibacterium, Shewanella, Bibersteinia, Haemophilus, Alistepes, Actinobacillus, or Helicobacter.*

10. The method of claim 1, wherein the sialyltransferase comprises an α(2,3) sialyltransferase or an α(2,6) sialyltransferase.

11. The method of claim 1, wherein the enzyme comprises a mutation compared to a naturally occurring α(2,3) sialyltransferase.

12. The method of claim 11, wherein the mutation that renders the enzyme more α(2,6)-selective than the naturally occurring α(2,3) sialyltransferase.

13. The method of claim 1, wherein the enzyme comprises an α(2,6) sialyltransferase.

14. The method of claim 1, wherein the $C_\alpha$ root-mean-square deviation (RMSD) between the backbone of the enzyme and a naturally occurring sialyltransferase is less than 3Å.

15. The method of claim 1, wherein the bacterium is in a culture medium.

16. The method of claim 1, wherein the bacterium is cultured in a biofermentor.

17. The method of claim 1, further comprising retrieving the sialylated oligosaccharide from the bacterium or from a culture supernatant of the bacterium.

18. The method of claim 1, wherein the sialylated oligosaccharide comprises a sialyllactose.

19. The method of claim 1, wherein the sialylated oligosaccharide comprises 3'-sialyllactose (3'-SL), 6'-sialyllactose (6'-SL), 3'-sialyl-3-fucosyllactose (3'-S3FL), sialyllacto-N-tetraose a (SLNT a), sialyllacto-N-tetraose b (SLNT b), disialyllacto-N-tetraose (DSLNT), sialyllacto-N-fucopentaose II (SLNFP II), or sialyllacto-N-tetraose c (SLNT c).

20. The method of claim 1, wherein the bacterium further comprises an exogenous or endogenous N-acetylneuraminate synthase, an exogenous or endogenous UDP-N-acetylglucosamine 2-epimerase, an exogenous or endogenous N-acetylneuraminate cytidylyltransferase, or any combination thereof.

21. The method of claim 20, wherein the bacterium comprises an exogenous N-acetylneuraminate synthase, UDP-N-acetylglucosamine 2-epimerase, and N-acetylneuraminate cytidylyltransferase from *Campylobacter jejuni.*

22. The method of claim 1, wherein the bacterium comprises a reduced level of β-galactosidase activity compared to a corresponding wild-type bacterium.

23. The method of claim 22, wherein the reduced level of β-galactosidase activity comprises reduced expression of a β-galactosidase gene or reduced β-galactosidase enzymatic activity.

24. The method of claim 22, wherein the reduced level is less than 10% the level of the corresponding wild-type bacterium in the presence of lactose.

25. The method of claim 22, wherein the bacterium comprises a deleted or inactivated endogenous β-galactosidase gene.

26. The method of claim 22, wherein the bacterium comprises a deleted or inactivated endogenous lacZ gene and/or a deleted or inactivated endogenous lacI gene.

27. The method of claim 22, wherein the bacterium comprises an endogenous β-galactosidase gene, wherein at least a portion of a promoter of the endogenous β-galactosidase gene has been deleted.

28. The method of claim 22, wherein the bacterium comprises an exogenous β-galactosidase enzyme with reduced enzymatic activity compared to an endogenous β-galactosidase enzyme in a corresponding wild-type bacterium.

29. The method of claim 22, wherein the bacterium comprises an exogenous β-galactosidase gene that is expressed at a lower level than to an endogenous β-galactosidase gene in a corresponding wild-type bacterium.

30. The method of claim 29, wherein the bacterium comprises less than 50 units of β-galactosidase activity when cultured in the presence of lactose.

31. The method of claim 1, wherein the bacterium comprises a lactose permease gene.

32. The method of claim 1, wherein the bacterium further comprises a mutation in a thyA gene.

33. The method of claim 1, wherein the bacterium does not express a β-galactoside transacetylase.

34. The method of claim 33, wherein the bacterium comprises a lacA mutation.

35. The method of claim 1, wherein the bacterium accumulates intracellular lactose in the presence of exogenous lactose.

36. The method of claim 1, wherein the bacterium is an *Escherichia coli* (*E. coli*) bacterium.

37. The method of claim 1, wherein the bacterium is a member of the *Bacillus, Pantoea, Lactobacillus, Lactococcus, Streptococcus, Proprionibacterium, Enterococcus, Bifidobacterium, Sporolactobacillus, Micromomospora, Micrococcus, Rhodococcus*, or *Pseudomonas* genus.

38. The method of claim 1, wherein the bacterium is a *Bacillus licheniformis, Bacillus subtilis, Bacillus coagulans, Bacillus thermophiles, Bacillus laterosporus, Bacillus megaterium, Bacillus mycoides, Bacillus pumilus, Bacillus lentus, Bacillus cereus, and Bacillus circulans, Erwinia herbicola* (*Pantoea agglomerans*), *Citrobacter freundii, Pantoea citrea, Pectobacterium carotovorum, Xanthomonas campestris Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Streptococcus thermophiles, Proprionibacterium freudenreichii, Enterococcus faecium, Enterococcus thermophiles*), *Bifidobacterium longum, Bifidobacterium infantis, Bifidobacterium bifidum, Pseudomonas fluorescens*, or *Pseudomonas aeruginosa* bacterium.

39. The method of claim 36, wherein the *E. coli* bacterium is a G1724 strain bacterium.

40. The method of claim 39, wherein the bacterium comprises a lacIq or lacPL8 promoter mutation.

41. The method of claim 1, wherein the bacterium comprises a nucleic acid construct comprising an isolated nucleic acid encoding the lactose-utilizing sialyltransferase enzyme.

42. The method of claim 1, wherein a chromosome of the bacterium comprises a nucleic acid construct comprising an isolated nucleic acid encoding the lactose-utilizing sialyltransferase enzyme.

43. The method of claim 41, wherein the nucleic acid is operably linked to a heterologous control sequence that directs the production of the enzyme in the bacterium.

44. The method of claim 43, wherein the heterologous control sequence comprises a bacterial promoter, a bacterial operator, a bacterial ribosome binding site, a bacterial transcriptional terminator, or a plasmid selectable marker.

45. The method of claim 1, wherein the bacterium comprises the following genotype: PlacIq-lacY, Δ(lacI-lacZ), ΔlacA, ΔthyA::(0.8RBS lacZ+), ampC::(Ptrp M13g8 RBS-λcI+, CAT), ΔnanATE::scar.

46. The method of claim 1, wherein the enzyme comprises the amino acid sequence of SEQ ID NO: 27.

47. The method of claim 1, wherein the enzyme comprises an amino acid sequence that is about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO: 27.

48. The method of claim 47, wherein the enzyme comprises a mutation at the position that aligns with position 122 of the amino acid sequence of SEQ ID NO: 15.

49. The method of claim 48, wherein the mutation is selected from the group consisting of A122V, A122L, A122M and A122F.

50. The method of claim 1, wherein the enzyme comprises the amino acid sequence of SEQ ID NO: 18.

51. The method of claim 1, wherein the enzyme comprises the amino acid sequence of SEQ ID NO: 15.

* * * * *

UNITED STATES PATENT AND TRADEMARK OFFICE

CERTIFICATE OF CORRECTION

PATENT NO. : 11,274,325 B2
APPLICATION NO. : 16/221193
DATED : March 15, 2022
INVENTOR(S) : Mallipeddi et al.

It is certified that error appears in the above-identified patent and that said Letters Patent is hereby corrected as shown below:

In the Claims

Column 147, Line 49 Claim 5, delete "naturally occurring" before "enzyme".

Signed and Sealed this
Tenth Day of May, 2022

Katherine Kelly Vidal

Katherine Kelly Vidal
*Director of the United States Patent and Trademark Office*

SEQUENCE LISTING

```
<160> NUMBER OF SEQ ID NOS: 30

<210> SEQ ID NO 1
<211> LENGTH: 514
<212> TYPE: PRT
<213> ORGANISM: Photobacterium sp.

<400> SEQUENCE: 1

Met Lys Asn Phe Leu Leu Leu Thr Leu Ile Leu Leu Thr Ala Cys Asn
1               5                   10                  15

Asn Ser Glu Glu Asn Thr Gln Ser Ile Ile Lys Asn Asp Ile Asn Lys
            20                  25                  30

Thr Ile Ile Asp Glu Glu Tyr Val Asn Leu Glu Pro Ile Asn Gln Ser
        35                  40                  45

Asn Ile Ser Phe Thr Lys His Ser Trp Val Gln Thr Cys Gly Thr Gln
    50                  55                  60

Gln Leu Leu Thr Glu Gln Asn Lys Glu Ser Ile Ser Leu Ser Val Val
65                  70                  75                  80

Ala Pro Arg Leu Asp Asp Asp Glu Lys Tyr Cys Phe Asp Phe Asn Gly
                85                  90                  95

Val Ser Asn Lys Gly Glu Lys Tyr Ile Thr Lys Val Thr Leu Asn Val
            100                 105                 110

Val Ala Pro Ser Leu Glu Val Tyr Val Asp His Ala Ser Leu Pro Thr
        115                 120                 125

Leu Gln Gln Leu Met Asp Ile Ile Lys Ser Glu Glu Glu Asn Pro Thr
    130                 135                 140

Ala Gln Arg Tyr Ile Ala Trp Gly Arg Ile Val Pro Thr Asp Glu Gln
145                 150                 155                 160

Met Lys Glu Leu Asn Ile Thr Ser Phe Ala Leu Ile Asn Asn His Thr
                165                 170                 175

Pro Ala Asp Leu Val Gln Glu Ile Val Lys Gln Ala Gln Thr Lys His
            180                 185                 190

Arg Leu Asn Val Lys Leu Ser Ser Asn Thr Ala His Ser Phe Asp Asn
        195                 200                 205

Leu Val Pro Ile Leu Lys Glu Leu Asn Ser Phe Asn Asn Val Thr Val
    210                 215                 220

Thr Asn Ile Asp Leu Tyr Asp Asp Gly Ser Ala Glu Tyr Val Asn Leu
225                 230                 235                 240

Tyr Asn Trp Arg Asp Thr Leu Asn Lys Thr Asp Asn Leu Lys Ile Gly
                245                 250                 255

Lys Asp Tyr Leu Glu Asp Val Ile Asn Gly Ile Asn Glu Asp Thr Ser
            260                 265                 270

Asn Thr Gly Thr Ser Ser Val Tyr Asn Trp Gln Lys Leu Tyr Pro Ala
        275                 280                 285

Asn Tyr His Phe Leu Arg Lys Asp Tyr Leu Thr Leu Glu Pro Ser Leu
    290                 295                 300

His Glu Leu Arg Asp Tyr Ile Gly Asp Ser Leu Lys Gln Met Gln Trp
```

-continued

```
305                 310                 315                 320

Asp Gly Phe Lys Lys Phe Asn Ser Lys Gln Gln Glu Leu Phe Leu Ser
                325                 330                 335

Ile Val Asn Phe Asp Lys Gln Lys Leu Gln Asn Glu Tyr Asn Ser Ser
            340                 345                 350

Asn Leu Pro Asn Phe Val Phe Thr Gly Thr Thr Val Trp Ala Gly Asn
        355                 360                 365

His Glu Arg Glu Tyr Tyr Ala Lys Gln Gln Ile Asn Val Ile Asn Asn
    370                 375                 380

Ala Ile Asn Glu Ser Ser Pro His Tyr Leu Gly Asn Ser Tyr Asp Leu
385                 390                 395                 400

Phe Phe Lys Gly His Pro Gly Gly Gly Ile Ile Asn Thr Leu Ile Met
                405                 410                 415

Gln Asn Tyr Pro Ser Met Val Asp Ile Pro Ser Lys Ile Ser Phe Glu
            420                 425                 430

Val Leu Met Met Thr Asp Met Leu Pro Asp Ala Val Ala Gly Ile Ala
        435                 440                 445

Ser Ser Leu Tyr Phe Thr Ile Pro Ala Glu Lys Ile Lys Phe Ile Val
    450                 455                 460

Phe Thr Ser Thr Glu Thr Ile Thr Asp Arg Glu Thr Ala Leu Arg Ser
465                 470                 475                 480

Pro Leu Val Gln Val Met Ile Lys Leu Gly Ile Val Lys Glu Glu Asn
                485                 490                 495

Val Leu Phe Trp Ala Asp Leu Pro Asn Cys Glu Thr Gly Val Cys Ile
            500                 505                 510

Ala Val


<210> SEQ ID NO 2
<211> LENGTH: 417
<212> TYPE: PRT
<213> ORGANISM: Avibacterium paragallinarum

<400> SEQUENCE: 2

Met Arg Lys Ile Ile Thr Phe Phe Ser Leu Phe Phe Ser Ile Ser Ala
1               5                   10                  15

Trp Cys Gln Lys Met Glu Ile Tyr Leu Asp Tyr Ala Ser Leu Pro Ser
            20                  25                  30

Leu Asn Met Ile Leu Asn Leu Val Glu Asn Lys Asn Asn Glu Lys Val
        35                  40                  45

Glu Arg Ile Ile Gly Phe Glu Arg Phe Asp Phe Asn Lys Glu Ile Leu
    50                  55                  60

Asn Ser Phe Ser Lys Glu Arg Ile Glu Phe Ser Lys Val Ser Ile Leu
65                  70                  75                  80

Asp Ile Lys Glu Phe Ser Asp Lys Leu Tyr Leu Asn Ile Glu Lys Ser
                85                  90                  95

Asp Thr Pro Val Asp Leu Ile Ile His Thr Asn Leu Asp His Ser Val
            100                 105                 110

Arg Ser Leu Leu Ser Ile Phe Lys Thr Leu Ser Pro Leu Phe His Lys
        115                 120                 125

Ile Asn Ile Glu Lys Leu Tyr Leu Tyr Asp Asp Gly Ser Gly Asn Tyr
    130                 135                 140

Val Asp Leu Tyr Gln His Arg Gln Glu Asn Ile Ser Ala Ile Leu Ile
145                 150                 155                 160

Glu Ala Gln Lys Lys Leu Lys Asp Ala Leu Glu Asn Arg Glu Thr Asp
```

```
                165                 170                 175

Thr Asp Lys Leu His Ser Leu Thr Arg Tyr Thr Trp His Lys Ile Phe
            180                 185                 190

Pro Thr Glu Tyr Ile Leu Leu Arg Pro Asp Tyr Leu Asp Ile Asp Glu
        195                 200                 205

Lys Met Gln Pro Leu Lys His Phe Leu Ser Asp Thr Ile Val Ser Met
    210                 215                 220

Asp Leu Ser Arg Phe Ser His Phe Ser Lys Asn Gln Lys Glu Leu Phe
225                 230                 235                 240

Leu Lys Ile Thr His Phe Asp Gln Asn Ile Phe Asn Glu Leu Asn Ile
                245                 250                 255

Gly Thr Lys Asn Lys Glu Tyr Lys Thr Phe Ile Phe Thr Gly Thr Thr
            260                 265                 270

Thr Trp Glu Lys Asp Lys Lys Lys Arg Leu Asn Asn Ala Lys Leu Gln
        275                 280                 285

Thr Glu Ile Leu Glu Ser Phe Ile Lys Pro Asn Gly Lys Phe Tyr Leu
    290                 295                 300

Gly Asn Asp Ile Lys Ile Phe Phe Lys Gly His Pro Lys Gly Asp Asp
305                 310                 315                 320

Ile Asn Asp Tyr Ile Ile Arg Lys Thr Gly Ala Glu Lys Ile Pro Ala
                325                 330                 335

Asn Ile Pro Phe Glu Val Leu Met Met Thr Asn Ser Leu Pro Asp Tyr
            340                 345                 350

Val Gly Gly Ile Met Ser Thr Val Tyr Phe Ser Leu Pro Pro Lys Asn
        355                 360                 365

Ile Asp Lys Val Val Phe Leu Gly Ser Glu Lys Ile Lys Asn Glu Asn
    370                 375                 380

Asp Ala Lys Ser Gln Thr Leu Ser Lys Leu Met Leu Met Leu Asn Val
385                 390                 395                 400

Ile Thr Pro Glu Gln Ile Phe Phe Glu Glu Met Pro Asn Pro Ile Asn
                405                 410                 415

Phe


<210> SEQ ID NO 3
<211> LENGTH: 264
<212> TYPE: PRT
<213> ORGANISM: Actinobacillus ureae

<400> SEQUENCE: 3

Met Phe Lys Ile Lys Ser Tyr Gly Lys Asn Pro Gln Leu Gln Ala Val
1               5                   10                  15

Asp Ile Tyr Ile Asp Phe Ala Thr Ile Pro Ser Leu Ser Tyr Phe Leu
            20                  25                  30

His Phe Leu Lys His Lys His Asp His Gln Arg Leu Arg Leu Phe Ser
        35                  40                  45

Leu Ala Arg Phe Glu Met Pro Gln Thr Val Ile Glu Gln Tyr Glu Gly
    50                  55                  60

Ile Ile Gln Phe Ser Arg Asn Val Glu His Asn Val Glu Pro Leu Leu
65                  70                  75                  80

Glu Gln Leu Gln Thr Ile Leu Ser Gln Glu Gly Lys Gln Phe Glu Leu
                85                  90                  95

His Leu His Leu Asn Leu Phe His Ser Phe Glu Met Phe Leu Asn Leu
            100                 105                 110

Ser Pro Thr Tyr Thr Lys Tyr Lys Glu Lys Ile Ser Lys Ile Val Leu
```

-continued

```
        115                 120                 125

His Leu Tyr Asp Asp Gly Ser Glu Gly Val Met Lys Gln Tyr Gln Leu
    130                 135                 140

Gln Lys Ser Ser Ser Leu Val Gln Asp Leu Ala Ala Thr Lys Ala Ser
145                 150                 155                 160

Leu Val Ser Leu Phe Glu Asn Gly Glu Gly Ser Phe Ser Gln Ile Asp
                165                 170                 175

Leu Ile Arg Tyr Val Trp Asn Ala Val Leu Glu Thr His Tyr Tyr Leu
            180                 185                 190

Leu Ser Asp His Phe Leu Leu Asp Glu Lys Leu Gln Pro Leu Lys Ala
        195                 200                 205

Glu Leu Gly His Tyr Gln Leu Leu Asn Leu Ser Thr Tyr Gln Tyr Leu
    210                 215                 220

Ser Ser Glu Asp Leu Leu Trp Leu Lys Gln Ile Leu Lys Ile Asp Ala
225                 230                 235                 240

Glu Leu Glu Ser Leu Met Gln Lys Leu Thr Ala Gln Pro Val Tyr Phe
                245                 250                 255

Phe Ser Gly Thr Thr Phe Leu Gly
            260


<210> SEQ ID NO 4
<211> LENGTH: 399
<212> TYPE: PRT
<213> ORGANISM: Haemophilus ducreyi

<400> SEQUENCE: 4

Met Leu Ile Gln Gln Asn Leu Glu Ile Tyr Leu Asp Tyr Ala Thr Ile
1               5                   10                  15

Pro Ser Leu Ala Cys Phe Met His Phe Ile Gln His Lys Asp Asp Val
            20                  25                  30

Asp Ser Ile Arg Leu Phe Gly Leu Ala Arg Phe Asp Ile Pro Gln Ser
        35                  40                  45

Ile Ile Asp Arg Tyr Pro Ala Asn His Leu Phe Tyr His Asn Ile Asp
    50                  55                  60

Asn Arg Asp Leu Thr Ala Val Leu Asn Gln Leu Ala Asp Ile Leu Ala
65                  70                  75                  80

Gln Glu Asn Lys Arg Phe Gln Ile Asn Leu His Leu Asn Leu Phe His
                85                  90                  95

Ser Ile Asp Leu Phe Phe Ala Ile Tyr Pro Ile Tyr Gln Gln Tyr Gln
            100                 105                 110

His Lys Ile Ser Thr Ile Gln Leu Gln Leu Tyr Asp Asp Gly Ser Glu
        115                 120                 125

Gly Ile Val Thr Gln His Ser Leu Cys Lys Ile Ala Asp Leu Glu Gln
    130                 135                 140

Leu Ile Leu Gln His Lys Asn Val Leu Leu Glu Leu Leu Thr Lys Gly
145                 150                 155                 160

Thr Ala Asn Val Pro Asn Pro Thr Leu Leu Arg Tyr Leu Trp Asn Asn
                165                 170                 175

Ile Ile Asp Ser Gln Phe His Leu Ile Ser Asp His Phe Leu Gln His
            180                 185                 190

Pro Lys Leu Gln Pro Leu Lys Arg Leu Leu Lys Arg Tyr Thr Ile Leu
        195                 200                 205

Asp Phe Thr Cys Tyr Pro Arg Phe Asn Ala Glu Gln Lys Gln Leu Leu
    210                 215                 220
```

```
Lys Glu Ile Leu His Ile Ser Asn Glu Leu Glu Asn Leu Leu Lys Leu
225                 230                 235                 240

Leu Lys Gln His Asn Thr Phe Leu Phe Thr Gly Thr Thr Ala Phe Asn
                245                 250                 255

Leu Asp Gln Glu Lys Leu Asp Leu Leu Thr Gln Leu His Ile Leu Leu
            260                 265                 270

Leu Asn Glu His Gln Asn Pro His Ser Thr His Tyr Ile Gly Asn Asn
        275                 280                 285

Tyr Leu Leu Leu Ile Lys Gly His Ala Asn Ser Pro Ala Leu Asn His
    290                 295                 300

Thr Leu Ala Leu His Phe Pro Asp Ala Ile Phe Leu Pro Ala Asn Ile
305                 310                 315                 320

Pro Phe Glu Ile Phe Ala Met Leu Gly Phe Thr Pro Asn Lys Met Gly
                325                 330                 335

Gly Phe Ala Ser Thr Ser Tyr Ile Asn Tyr Pro Thr Glu Asn Ile Asn
            340                 345                 350

His Leu Phe Phe Leu Thr Ser Asp Gln Pro Ser Ile Arg Thr Lys Trp
        355                 360                 365

Leu Asp Tyr Glu Lys Gln Phe Gly Leu Met Tyr Ser Leu Leu Ala Met
    370                 375                 380

Gln Lys Ile Asn Glu Asp Gln Ala Phe Met Cys Thr Ile His Asn
385                 390                 395


<210> SEQ ID NO 5
<211> LENGTH: 498
<212> TYPE: PRT
<213> ORGANISM: Artificial Sequence
<220> FEATURE:
<223> OTHER INFORMATION: Hypothetical protein (Alistipes)

<400> SEQUENCE: 5

Met Lys Arg Leu Phe Arg Leu Phe Leu Cys Leu Ala Leu Leu Ser Gly
1               5                   10                  15

Thr Ala Ala Cys Ser Asp Asp Glu Val Ser Gln Asn Leu Ile Val Ile
            20                  25                  30

Asn Gly Gly Glu His Phe Leu Ser Leu Asp Gly Leu Ala Arg Ala Gly
        35                  40                  45

Lys Ile Ser Val Leu Ala Pro Ala Pro Trp Arg Val Thr Lys Ala Ala
    50                  55                  60

Gly Asp Thr Trp Phe Arg Leu Ser Ala Thr Glu Gly Pro Ala Gly Tyr
65                  70                  75                  80

Ser Glu Val Glu Leu Ser Leu Asp Glu Asn Pro Gly Ala Ala Arg Ser
                85                  90                  95

Ala Gln Leu Ala Phe Ala Cys Gly Asp Ala Ile Val Pro Phe Arg Leu
            100                 105                 110

Ser Gln Gly Ala Leu Ser Ala Gly Tyr Asp Ser Pro Asp Tyr Tyr Phe
        115                 120                 125

Tyr Val Thr Phe Gly Thr Met Pro Thr Leu Tyr Ala Gly Ile His Leu
    130                 135                 140

Leu Ser His Asp Lys Pro Gly Tyr Val Phe Tyr Ser Arg Ser Lys Thr
145                 150                 155                 160

Phe Asp Pro Ala Glu Phe Pro Ala Arg Ala Glu Val Thr Thr Ala Ala
                165                 170                 175

Asp Arg Thr Ala Asp Ala Thr Gln Ala Glu Met Glu Ala Met Ala Arg
            180                 185                 190
```

```
Glu Met Lys Arg Arg Ile Leu Glu Ile Asn Ser Ala Asp Pro Thr Ala
        195                 200                 205

Val Phe Gly Leu Tyr Val Asp Asp Leu Arg Cys Arg Ile Gly Tyr Asp
    210                 215                 220

Trp Phe Val Ala Gln Gly Ile Asp Ser Ala Arg Val Lys Val Ser Met
225                 230                 235                 240

Leu Ser Asp Gly Thr Gly Thr Tyr Asn Asn Phe Tyr Asn Tyr Phe Gly
                245                 250                 255

Asp Ala Ala Thr Ala Glu Gln Asn Trp Glu Ser Tyr Ala Ser Glu Val
            260                 265                 270

Glu Ala Leu Asp Trp Asn His Gly Gly Arg Tyr Pro Glu Thr Arg Ser
        275                 280                 285

Leu Pro Glu Phe Glu Ser Tyr Thr Trp Pro Tyr Tyr Leu Ser Thr Arg
    290                 295                 300

Pro Asp Tyr Arg Leu Val Val Gln Asp Gly Ser Leu Leu Glu Ser Ser
305                 310                 315                 320

Cys Pro Phe Ile Thr Glu Lys Leu Gly Glu Met Glu Ile Glu Ser Ile
                325                 330                 335

Gln Pro Tyr Glu Met Leu Ser Ala Leu Pro Glu Ser Ser Arg Lys Arg
            340                 345                 350

Phe Tyr Asp Met Ala Gly Phe Asp Tyr Asp Lys Phe Ala Ala Leu Phe
        355                 360                 365

Asp Ala Ser Pro Lys Lys Asn Leu Ile Ile Ile Gly Thr Ser His Ala
    370                 375                 380

Asp Asp Ala Ser Ala Arg Leu Gln Arg Asp Tyr Val Ala Arg Ile Met
385                 390                 395                 400

Glu Gln Tyr Gly Ala Gln Tyr Asp Val Phe Phe Lys Pro His Pro Ala
                405                 410                 415

Asp Thr Thr Ser Ala Gly Tyr Glu Thr Glu Phe Pro Gly Leu Thr Leu
            420                 425                 430

Leu Pro Gly Gln Met Pro Phe Glu Ile Phe Val Trp Ser Leu Ile Asp
        435                 440                 445

Arg Val Asp Met Ile Gly Gly Tyr Pro Ser Thr Val Phe Leu Thr Val
    450                 455                 460

Pro Val Asp Lys Val Arg Phe Ile Phe Ala Ala Asp Ala Ala Ser Leu
465                 470                 475                 480

Val Arg Pro Leu Asn Ile Leu Phe Arg Asp Ala Thr Asp Val Glu Trp
                485                 490                 495

Met Gln


<210> SEQ ID NO 6
<211> LENGTH: 410
<212> TYPE: PRT
<213> ORGANISM: Bibersteinia trealosi

<400> SEQUENCE: 6

Met Glu Phe Cys Lys Met Ala Thr Thr Gln Lys Ile Cys Val Tyr Leu
1               5                   10                  15

Asp Tyr Ala Thr Ile Pro Ser Leu Asn Tyr Ile Leu His Phe Ala Gln
            20                  25                  30

His Phe Glu Asp Gln Glu Thr Ile Arg Leu Phe Gly Leu Ser Arg Phe
        35                  40                  45

His Ile Pro Glu Ser Val Ile Gln Arg Tyr Pro Lys Gly Val Val Gln
    50                  55                  60
```

```
Phe Tyr Pro Asn Gln Glu Lys Asp Phe Ser Ala Leu Leu Leu Ala Leu
65                  70                  75                  80

Lys Asn Ile Leu Ile Glu Val Lys Gln Gln Gln Arg Lys Cys Glu Ile
                85                  90                  95

Glu Leu His Leu Asn Leu Phe His Tyr Gln Leu Leu Leu Leu Pro Phe
            100                 105                 110

Leu Ser Leu Tyr Leu Asp Thr Gln Asp Tyr Cys His Leu Thr Leu Lys
        115                 120                 125

Phe Tyr Asp Asp Gly Ser Glu Ala Ile Ser Ala Leu Gln Glu Leu Ala
    130                 135                 140

Leu Ala Pro Asp Leu Ala Ala Gln Ile Gln Phe Glu Lys Gln Gln Phe
145                 150                 155                 160

Asp Glu Leu Val Val Lys Lys Ser Phe Lys Leu Ser Leu Leu Ser Arg
                165                 170                 175

Tyr Phe Trp Gly Lys Leu Phe Glu Ser Glu Tyr Ile Trp Phe Asn Gln
            180                 185                 190

Ala Ile Leu Gln Lys Ala Glu Leu Gln Ile Leu Lys Gln Glu Ile Ser
        195                 200                 205

Ser Ser Arg Gln Met Asp Phe Ala Ile Tyr Gln Gln Met Ser Asp Glu
    210                 215                 220

Gln Lys Gln Leu Val Leu Glu Ile Leu Asn Ile Asp Leu Asn Lys Val
225                 230                 235                 240

Ala Tyr Leu Lys Gln Leu Met Glu Asn Gln Pro Ser Phe Leu Phe Leu
                245                 250                 255

Gly Thr Thr Leu Phe Asn Ile Thr Gln Glu Thr Lys Thr Trp Leu Met
            260                 265                 270

Gln Met His Val Asp Leu Ile Gln Gln Tyr Cys Leu Pro Ser Gly Gln
        275                 280                 285

Phe Phe Asn Asn Lys Ala Gly Tyr Leu Cys Phe Tyr Lys Gly His Pro
    290                 295                 300

Asn Glu Lys Glu Met Asn Gln Met Ile Leu Ser Gln Phe Lys Asn Leu
305                 310                 315                 320

Ile Ala Leu Pro Asp Asp Ile Pro Leu Glu Ile Leu Leu Leu Leu Gly
                325                 330                 335

Val Ile Pro Ser Lys Val Gly Gly Phe Ala Ser Ser Ala Leu Phe Asn
            340                 345                 350

Phe Thr Pro Ala Gln Ile Glu Asn Ile Ile Phe Phe Thr Pro Arg Tyr
        355                 360                 365

Phe Glu Lys Asp Asn Arg Leu His Ala Thr Gln Tyr Arg Leu Met Gln
    370                 375                 380

Gly Leu Ile Glu Leu Gly Tyr Leu Asp Ala Glu Lys Ser Val Thr His
385                 390                 395                 400

Phe Glu Ile Met Gln Leu Leu Thr Lys Glu
                405                 410


<210> SEQ ID NO 7
<211> LENGTH: 367
<212> TYPE: PRT
<213> ORGANISM: Shewanella piezotolerans

<400> SEQUENCE: 7

Met Leu Val Asn Asn Gln Ser His Asn Pro Lys Leu Ile Cys Trp Gln
1               5                   10                  15

Arg His Pro Val Asn Asp Glu Ala Leu Leu Gln Gly Ile Asn Ala Ala
            20                  25                  30
```

-continued

```
Ser Phe Val Ser Ile Ala Ser Leu Cys Gln His Ala Ala Thr Leu Leu
        35                  40                  45

Ala Gly His Pro His Ser His Ile Thr Ile Tyr Gly Asn Thr Tyr Trp
    50                  55                  60

Ser Lys Asp Leu Ala Arg Leu Ile Arg Tyr Leu Thr Arg Ile Ser Gly
65                  70                  75                  80

Val Glu Ile Lys Lys Leu Glu Leu Ile Asp Asp Gly Ser Ser Glu Tyr
                85                  90                  95

Gln Lys Met Phe Tyr Trp Gln Arg Leu Ser Ser Glu Glu Gln Thr Arg
            100                 105                 110

Asp Leu Ala Thr Gly Leu Lys Asn Leu Lys Ser Tyr Leu Ser Gly Asn
        115                 120                 125

Asp Asn Lys Leu Leu Arg Leu Leu Thr Gly His Ser Asn Lys Leu Pro
    130                 135                 140

Arg Arg Leu Ser Ser Phe Met Asn Trp His Gln Leu Phe Pro Thr Thr
145                 150                 155                 160

Tyr His Met Leu Arg Met Asp Tyr Leu Asp Lys Pro Glu Leu His Gln
                165                 170                 175

Leu Lys Gln Tyr Leu Gly Asn Asn Ala Gln Gln Ile Arg Trp Asn Tyr
            180                 185                 190

Ile Ala Asp Asn Leu Phe Asp Asp Glu Gln Gln Ser Leu Phe Tyr Gln
        195                 200                 205

Leu Leu Gly Ile Ser Leu Ala Glu Gln Lys Gln Leu Arg Ala Gly Arg
    210                 215                 220

Gln Gln Leu His Asp Phe Met Phe Ile Gly Val Asp Ser Ser Asn Ala
225                 230                 235                 240

Ser Ser Lys Leu Gln Ile Asn Val Ile Ala Asp Ser Arg Gln Glu Ser
                245                 250                 255

Gly Ile Ile Pro Thr Ile Thr Ala Lys Lys Met Leu Phe Lys Gly His
            260                 265                 270

Pro Phe Ala Asn Phe Asn Gln Thr Ile Val Asp Ala His Gln Met Gly
        275                 280                 285

Glu Met Pro Ala Met Ile Pro Phe Glu Thr Leu Ile Met Thr Gly Asn
    290                 295                 300

Leu Pro Gln Lys Val Gly Gly Met Ala Ser Ser Leu Tyr Phe Ser Leu
305                 310                 315                 320

Pro Asn Asn Tyr His Ile Glu Tyr Ile Val Phe Ser Gly Ser Lys Lys
                325                 330                 335

Asp Leu Glu Gln His Ala Leu Leu Gln Ile Met Leu Tyr Leu Lys Val
            340                 345                 350

Ile Ser Pro Glu Arg Val Tyr Phe Ser Glu Gln Phe Lys Ser Cys
        355                 360                 365
```

<210> SEQ ID NO 8
<211> LENGTH: 422
<212> TYPE: PRT
<213> ORGANISM: Helicobacter acinonychis

<400> SEQUENCE: 8

```
Met Gly Thr Ile Lys Lys Pro Leu Ile Ile Ala Gly Asn Gly Pro Ser
1               5                   10                  15

Ile Lys Asp Leu Asp Tyr Ala Leu Phe Pro Lys Asp Phe Asp Val Phe
            20                  25                  30

Arg Cys Asn Gln Phe Tyr Phe Glu Asp Lys Tyr Tyr Leu Gly Arg Glu
```

-continued

```
        35                  40                  45

Ile Lys Gly Val Phe Phe Asn Pro Cys Val Leu Ser Ser Gln Met Gln
    50                  55                  60

Thr Val Gln Tyr Leu Met Asp Asn Gly Glu Tyr Ser Ile Glu Arg Phe
65                  70                  75                  80

Phe Cys Ser Val Ser Thr Asp Arg His Asp Phe Asp Gly Asp Tyr Gln
                85                  90                  95

Thr Ile Leu Pro Val Asp Gly Tyr Leu Lys Ala His Tyr Pro Phe Val
            100                 105                 110

Cys Asp Thr Phe Ser Leu Phe Lys Gly His Glu Glu Ile Leu Lys His
        115                 120                 125

Val Lys Tyr His Leu Lys Thr Tyr Ser Lys Glu Leu Ser Ala Gly Val
    130                 135                 140

Leu Met Leu Leu Ser Ala Val Val Leu Gly Tyr Lys Glu Ile Tyr Leu
145                 150                 155                 160

Val Gly Ile Asp Phe Gly Ala Ser Ser Trp Gly His Phe Tyr Asp Glu
                165                 170                 175

Ser Gln Ser Gln His Phe Ser Asn His Met Ala Asp Cys His Asn Ile
            180                 185                 190

Tyr Tyr Asp Met Leu Thr Ile Cys Leu Cys Gln Lys Tyr Ala Lys Leu
        195                 200                 205

Tyr Ala Leu Ala Pro Asn Ser Pro Leu Ser His Leu Leu Thr Leu Asn
    210                 215                 220

Pro Gln Ala Lys Tyr Pro Phe Glu Leu Leu Asp Lys Pro Ile Gly Tyr
225                 230                 235                 240

Thr Ser Asp Leu Ile Ile Ser Ser Pro Leu Glu Glu Lys Leu Leu Glu
                245                 250                 255

Phe Lys Asn Ile Glu Glu Lys Leu Leu Glu Phe Lys Asn Ile Glu Glu
            260                 265                 270

Lys Leu Leu Glu Phe Lys Asn Ile Glu Glu Lys Leu Leu Glu Phe Lys
        275                 280                 285

Asn Ile Glu Glu Lys Leu Leu Glu Phe Lys Asn Ile Glu Glu Lys Leu
    290                 295                 300

Leu Glu Phe Lys Asn Ile Glu Glu Lys Leu Leu Glu Phe Lys Asn Ile
305                 310                 315                 320

Glu Glu Lys Leu Leu Glu Phe Lys Asn Ile Glu Glu Lys Leu Leu Glu
                325                 330                 335

Phe Lys Asn Ile Glu Glu Lys Leu Leu Glu Phe Lys Asn Ile Glu Glu
            340                 345                 350

Lys Leu Leu Glu Phe Lys Asn Ile Glu Glu Lys Leu Leu Glu Phe Lys
        355                 360                 365

Asn Ile Glu Glu Lys Leu Leu Glu Phe Lys Asn Ile Glu Glu Lys Leu
    370                 375                 380

Leu Ala Ser Arg Leu Asn Asn Ile Leu Arg Lys Ile Lys Arg Lys Ile
385                 390                 395                 400

Leu Pro Phe Phe Trp Gly Gly Gly Val Thr Pro Thr Leu Lys Val Ser
                405                 410                 415

Phe Arg Trp Gly Ala Ala
            420
```

<210> SEQ ID NO 9
<211> LENGTH: 318
<212> TYPE: PRT
<213> ORGANISM: Helicobacter pylori -continued

<400> SEQUENCE: 9

```
Met Lys Lys Pro Leu Ile Ile Ala Gly Asn Gly Pro Ser Ile Lys Asp
1               5                   10                  15

Leu Asp Tyr Ser Leu Phe Pro Lys Asp Phe Glu Val Phe Arg Cys Asn
            20                  25                  30

Gln Phe Tyr Phe Glu Asp Lys Tyr Tyr Leu Gly Arg Glu Ile Lys Gly
        35                  40                  45

Val Phe Phe Asn Pro Cys Val Leu Ser Ser Gln Met Gln Thr Ala Gln
    50                  55                  60

Tyr Leu Met Asp Asn Gly Glu Tyr Ser Ile Glu Arg Phe Phe Cys Ser
65                  70                  75                  80

Val Ser Thr Asp Arg His Asp Phe Asp Gly Asp Tyr Gln Thr Ile Leu
                85                  90                  95

Pro Val Glu Gly Tyr Leu Lys Ala His Tyr Pro Phe Val Cys Asp Thr
            100                 105                 110

Phe Ser Leu Phe Lys Gly His Glu Glu Ile Leu Arg His Val Lys Tyr
        115                 120                 125

His Leu Lys Thr Tyr Ser Lys Glu Leu Ser Ala Gly Val Leu Met Leu
    130                 135                 140

Leu Ser Ala Val Val Leu Gly Tyr Lys Glu Ile Tyr Leu Val Gly Ile
145                 150                 155                 160

Asp Phe Gly Ala Ser Ser Trp Gly His Phe Tyr Asp Glu Ser Gln Ser
                165                 170                 175

Gln His Phe Ser Asn His Met Ala Asp Cys His Asn Ile Tyr Tyr Asp
            180                 185                 190

Met Phe Thr Ile Cys Leu Cys Gln Lys Tyr Ala Lys Leu Tyr Ala Leu
        195                 200                 205

Ala Pro Asn Ser Pro Leu Arg His Ile Leu Ala Leu Asn Pro Gln Ala
    210                 215                 220

Lys Tyr His Phe Glu Leu Leu Asp Lys Pro Ile Gly Tyr Thr Ser Asp
225                 230                 235                 240

Leu Ile Val Ser Leu Pro Leu Glu Glu Lys Leu Leu Glu Phe Lys Asn
                245                 250                 255

Ile Glu Glu Lys Leu Leu Glu Phe Lys Asn Ile Glu Glu Lys Leu Leu
            260                 265                 270

Glu Phe Lys Asn Ile Glu Glu Lys Leu Leu Val Asn Arg Leu Lys Asn
        275                 280                 285

Ile Leu Arg Lys Ile Lys Arg Lys Ile Leu Pro Phe Trp Gly Gly Gly
    290                 295                 300

Gly Asn Thr His Leu Lys Val Ser Phe Arg Trp Gly Val Ala
305                 310                 315
```

<210> SEQ ID NO 10
<211> LENGTH: 314
<212> TYPE: PRT
<213> ORGANISM: Helicobacter cetorum

<400> SEQUENCE: 10

```
Met Ser Glu Lys Ile Phe Ser Gln Val Asp Glu Lys Asn Gln Lys Lys
1               5                   10                  15

Pro Leu Ile Ile Ala Gly Asn Gly Pro Ser Ile Lys Asp Leu Asp Tyr
            20                  25                  30

Ser Leu Phe Pro Lys Asp Phe Asp Val Phe Arg Cys Asn Gln Phe Tyr
        35                  40                  45
```

```
Phe Glu Asp Lys Tyr Tyr Leu Gly Lys Glu Val Lys Gly Val Phe Phe
    50                  55                  60

Asn Pro Cys Val Phe His Asn Gln Met Asn Thr Ala Lys His Leu Ile
65                  70                  75                  80

Asp Asn Asn Glu Tyr Tyr Ile Glu Gln Phe Phe Cys Ser Val Ser Lys
                85                  90                  95

Glu Gln His Asp Phe Asn Gly Asp Tyr Gln Thr Ile Leu Ser Val Asp
            100                 105                 110

Glu Tyr Leu Arg Ala Asn Tyr Pro Phe Val Arg Asp Thr Phe Ser Leu
        115                 120                 125

Phe Gly Glu His Glu Glu Ile Leu Asn His Val Lys Tyr His Leu Lys
    130                 135                 140

Thr Tyr Ser Lys Glu Leu Ser Ala Gly Val Leu Met Leu Leu Ser Ala
145                 150                 155                 160

Ile Val Leu Gly Tyr Lys Glu Ile Tyr Leu Val Gly Val Asp Phe Gly
                165                 170                 175

Ala Asn Ser Trp Gly His Phe Tyr Asp Asp Asn Gln Ser Gln His Phe
            180                 185                 190

Ile Asn His Met Ala Asp Cys His Asn Ile Tyr Tyr Asp Met Leu Thr
        195                 200                 205

Ile Tyr Leu Cys Gln Lys Tyr Ala Lys Leu Tyr Ala Leu Val Pro Asn
    210                 215                 220

Ser Pro Leu Asn His Leu Leu Pro Leu Asn Leu Gln Ala Asn His Val
225                 230                 235                 240

Phe Glu Leu Leu Asp Lys Pro Ile Gly Tyr Thr Ser Asp Leu Ile Val
                245                 250                 255

Ser Ser Pro Leu Glu Glu Lys Leu Leu Glu Ser Lys Asn Ile Asp Glu
            260                 265                 270

Arg Phe Ser Gln Asn Lys Ser Phe Lys Asn Tyr Leu Gln Arg Leu Lys
        275                 280                 285

Asp Lys Phe Leu Gln Met Ile Phe Arg Gly Gly Gly Val Ile Thr Ile
    290                 295                 300

Pro Arg Val Ile Phe Lys Gly Lys Phe Ala
305                 310
```

<210> SEQ ID NO 11
<211> LENGTH: 8184
<212> TYPE: DNA
<213> ORGANISM: Artificial Sequence
<220> FEATURE:
<223> OTHER INFORMATION: Synthetic construct

<400> SEQUENCE: 11

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatatg cggtgtgaaa taccgcacag atgcgtaagg agaaaatacc gcatcaggcg    240

cctcctcaac ctgtatattc gtaaaccacg cccaatggga gctgtctcag gtttgttcct    300

gattggttac ggcgcgtttc gcatcattgt tgagtttttc cgccagcccg acgcgcagtt    360

taccggtgcc tgggtgcagt acatcagcat ggggcaaatt ctttccatcc cgatgattgt    420

cgcgggtgtg atcatgatgg tctgggcata tcgtcgcagc ccacagcaac acgtttcctg    480

aggaaccatg aaacagtatt tagaactgat gcaaaaagtg ctcgacgaag gcacacagaa    540
```

-continued

```
aaacgaccgt accggaaccg gaacgctttc catttttggt catcagatgc gttttaacct    600
gcaagatgga ttcccgctgg tgacaactaa acgttgccac ctgcgttcca tcatccatga    660
actgctgtgg tttctgcagg gcgacactaa cattgcttat ctacacgaaa acaatgtcac    720
catctgggac gaatgggccg atgaaaacgg cgacctcggg ccagtgtatg gtaaacagtg    780
gcgcgcctgg ccaacgccag atggtcgtca tattgaccag atcactacgg tactgaacca    840
gctgaaaaac gacccggatt cgcgccgcat tattgtttca gcgtggaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta aacccgaatc   1200
catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggttttttt accctccgtt aaattcttcg agacgccttc ccgaaggcgc cattcgccat   1380
tcaggctgcg caactgttgg gaagggcgat cggtgcgggc ctcttcgcta ttacgccagc   1440
tggcgaaagg gggatgtgct gcaaggcgat taagttgggt aacgccaggg ttttcccagt   1500
cacgacgttg taaaacgacg gccagtgcca agcttactgc tcacaagaaa aaaggcacgt   1560
catctgacgt gccttttttta tttgtactac cctgtacgat tactgcaggt cgacttattt   1620
tttccatatc tgttcaacct tttttaaatc ctccaaacag tcaatatcta aacttgagct   1680
ttcgtccatt aaaaaatgct tggttttgct ttgtaaaaag ctaggattgt ttaaaaattc   1740
ttttatcttt aaaatataaa ttgcaccatt gctcatataa gttttaggca atttttgcct   1800
tggcataaaa ggatattcat cattacaaat ccctgctaaa tcgccacaat cattacaaac   1860
aaaggctttt agaattttat tatcacattc gcttacgcta attagggcat ttgcattgct   1920
atttttataa agattaaaag cttcattaat atgaatattt gttcttagcg gtgaagtggg   1980
ttgtaaaaaa actacatctt cataatcttt ataaaatttt agagcatgta acagcacttt   2040
atcgcttgtg gtatcatctt gtgcaaggct aattgggcgt tttaaaatat caacattttg   2100
actttttgca taatttaaaa tttcatcact atcactgctt acaacaactt tactaatgct   2160
tttagcattt agtgcagctt tgatcgtgta gtaaattaaa ggtttattgt ttaataaaac   2220
caaattttta tttttaatac cctttgagcc accacgagca gggattattg ctaagctcat   2280
tttatatcct taaaaacttt ttgtgtgctg agtttaaaaa aatctccgct ttgtaaatat   2340
tcaaaaaata attttgagct atctaaaatc tctaacttag cgctaaataa atcttgtttt   2400
ttatgaatag tgttaatagc ttttagtatt tcatcactat ttgcattaac ttttagtgta   2460
ttttcattgc caagtcttcc attttgtctt gagccaacta aaatccctgc tgtttttaag   2520
tataaggcct cttttaaaat acaacttgaa ttacctatta taaaatcagc atttttttaac   2580
aaagttataa aatactcaaa tctaagcgat ggaaaaagct taaatctagg gttattttta   2640
aactcttcat agctttgcaa gattaattca aaacctaaat cattatttgg ataaataaca   2700
atataatttt tattactttg tatcagtgct tttactaaat tgtctgcttg atttttaatg   2760
ctagtaattt cagttgtaac aggatgaaac ataagcaaag cgtagttttc ataatttata   2820
tcataatatt tttttgcttc gctaagtgaa attttattat cgtttaaaag ttctaaatca   2880
```

-continued

```
ggcgaaccta tgataaaaat agatttttca tcttctccaa gctgcattaa acgccttttt   2940
gcaaactcat catttactaa atgaatatga gctagttttg atatagcgtg gcgtaagcta   3000
tcgtcaatag ttcctgaaat ctctccgcct tcaatatgcg ctactaagat attatttaat   3060
gctccaacaa tagctgctgc taaaggctca attctatctc catgtactac gattaaatca   3120
ggttttagct catttgcata ccttgaaaat ccatcaattg tagtagctaa agccttatca   3180
gtttgataat atttatcata atttataaat tcataaatat ttttaaagcc atttttataa   3240
agttctttaa ctgtatagcc aaaattttta cttaagtgca ttcctgttgc aaagatgtaa   3300
agttcaaatt cgcttgagtt ttgcaccctg tacattaaag atttaatctt agaataatca   3360
gccctagagc ctgttataaa aaggattttt ttcacgcaaa atcctcatag cttaactgag   3420
catcattttc tatatctctt aatgcttttt tgcctaaaat attttcaaat tcagccgcac   3480
taattccacc aagtccaggt cttttaaccc aaatattatc catagataaa acttcgcctt   3540
ttttaatatc tttaatgcta actacacttg caaaggcaaa atcaattgta acttgttctt   3600
gtttagccgc tttttttactt tcattatttc ctcttattat agccatttgc tcactttgta   3660
taattagctc ttttaaagcc tttgtatcca tagaacaaac tatatcaggg ccacttctat   3720
gcatactatc agtaaaatgt ctttcaagca cacaagctcc aagtacaact gcacctaaac   3780
acgcaagatt atctgttgtg tggtcgctta agcctaccat acaagaaaat tcttttttta   3840
actcaagcat agcgtttaat cttacaagat tatgcggggt tgggtaaaga ttggtcgtgt   3900
gcattaaaac aaaaggaatt tcattgtcta ataagatttt tacagttggt tttatacttt   3960
caatactatt cattcctgtg ctaactatca taggcttttt aaaggctgct atgtgtttaa   4020
taagcggata attattacac tcacctgaac caatcttaaa agcactaact cccatatctt   4080
ctaagcggtt cgcacctgca cgagaaaaag gtgtgctaag ataaacaaga cctaattttt   4140
ctgtgtattc tttaagtgct agctcatctt tataatccaa agcacatttt tgcataatct   4200
cataaatgct tatttttgca ttaccaggaa ttactttttt agcggcctta ctcatctcat   4260
cttcaacaat atgagtttga tgctttataa tcttagcacc tgcgctaaag gctgcatcta   4320
ccataatttt agctagttct aaactgccat tatgattaat gcctatttca ggtacgacta   4380
agggtgcttt ttcttcactt atgattatat tttgtatttt tatttctttc atttattttc   4440
ctccttagtc gacggtaccc ttaagcgaat tttcctttaa agatcacgcg gggaattgta   4500
atgactccac ccccacggaa gatcatttga agaaacttat ctttaagacg ttgaagatag   4560
tttttgaagg acttattctg agagaagcgc tcgtcgatgt tcttcgactc taacagtttt   4620
tcttctaaag gggagctaac gattaaatcc gacgtgtagc cgatgggctt atcaagcagc   4680
tcaaatacat ggtttgcctg taagttcaac ggtaaaagat ggttcagagg actgttaggt   4740
actaaagcat ataatttggc gtatttttga caaaggtaaa tagtcaacat gtcataataa   4800
atgttatggc agtcagccat gtggttaata aagtgctgac tctggttgtc atcgtaaaaa   4860
tgtccccagc tatttgcgcc aaaatcgaca ccgactaagt agatttcctt gtatcctaaa   4920
acaattgcgc tcaacaacat aaggaccccc gcagataatt cttttgaata tgtcttcaga   4980
tggtatttga catggtttaa gatttcctca tgctccccaa acaagctaaa ggtgtcacgt   5040
acaaacgggt agtttgcacg aaggtattcg tccaccgata agatggtctg gtaatcaccg   5100
ttaaaatcgt gttgttcttt cgacacacta caaaagaact gctcgatgta gtattcgttg   5160
ttgtcaatta aatgcttcgc ggtattcatt tgattatgga agacgcacgg attaaagaat   5220
acacctttga cctctttgcc caagtaatac ttatcttcga aatagaattg gttacagcgg   5280
```

-continued

```
aaaacgtcga aatcttttgg gaacaacgaa tagtcaaggt ctttgattga tggtccgttg   5340
cccgcgataa tcaagggctt tttttggttc ttctcgtcaa cctggctgaa gatttttttcc  5400
gacatatgta tatctccttc ttgaattcta acaattgatt gaatgtatgc aaataaatgc   5460
atacaccata ggtgtggttt aatttgatgc cctttttcag ggctggaatg tgtaagagcg   5520
gggttattta tgctgttgtt tttttgttac tcgggaaggg ctttacctct tccgcataaa   5580
cgcttccatc agcgtttata gttaaaaaaa tctttcggaa ctggttttgc gcttacccca   5640
accaacaggg gatttgctgc tttccattga gcctgtttct ctgcgcgacg ttcgcggcgg   5700
cgtgtttgtg catccatctg gattctcctg tcagttagct ttggtggtgt gtggcagttg   5760
tagtcctgaa cgaaaacccc ccgcgattgg cacattggca gctaatccgg aatcgcactt   5820
acggccaatg cttcgtttcg tatcacacac cccaaagcct tctgctttga atgctgccct   5880
tcttcagggc ttaattttta agagcgtcac cttcatggtg gtcagtgcgt cctgctgatg   5940
tgctcagtat caccgccagt ggtatttatg tcaacaccgc cagagataat ttatcaccgc   6000
agatggttat ctgtatgttt tttatatgaa tttatttttt gcagggggc attgtttggt    6060
aggtgagaga tcaattctgc attaatgaat cggccaacgc gcggggagag gcggtttgcg   6120
tattgggcgc tcttccgctg ctagcggagt gtatactggc ttactatgtt ggcactgatg   6180
agggtgtcag tgaagtgctt catgtggcag gagaaaaaag gctgcaccgg tgcgtcagca   6240
gaatatgtga tacaggatat attccgcttc ctcgctcact gactcgctac gctcggtcgt   6300
tcgactgcgg cgagcggaaa tggcttacga acggggcgga gatttcctgg aagatgccag   6360
gaagatactt aacagggaag tgagagggcc gcggcaaagc cgtttttcca taggctccgc   6420
ccccctgaca agcatcacga aatctgacgc tcaaatcagt ggtggcgaaa cccgacagga   6480
ctataaagat accaggcgtt tccccctggc ggctccctcg tgcgctctcc tgttcctgcc   6540
tttcggttta ccggtgtcat tccgctgtta tggccgcgtt tgtctcattc cacgcctgac   6600
actcagttcc gggtaggcag ttcgctccaa gctggactgt atgcacgaac cccccgttca   6660
gtccgaccgc tgcgccttat ccggtaacta tcgtcttgag tccaacccgg aaagacatgc   6720
aaaagcacca ctggcagcag ccactggtaa ttgatttaga ggagttagtc ttgaagtcat   6780
gcgccggtta aggctaaact gaaaggacaa gttttggtga ctgcgctcct ccaagccagt   6840
tacctcggtt caaagagttg gtagctcaga gaaccttcga aaaaccgccc tgcaaggcgg   6900
tttttcgtt ttcagagcaa gagattacgc gcagaccaaa acgatctcaa gaagatcatc    6960
ttattaatca gataaaatat ttctaggcgg ccgcgaacga aaactcacgt taagggattt   7020
tggtcatgag attatcaaaa aggatcttca cctagatcct tttaaattaa aaatgaagtt   7080
ttaaatcaat ctaaagtata tatgagtaaa cttggtctga cagttaccaa tgcttaatca   7140
gtgaggcacc tatctcagcg atctgtctat ttcgttcatc catagttgcc tgactccccg   7200
tcgtgtagat aactacgata cgggagggct taccatctgg ccccagtgct gcaatgatac   7260
cgcgagaccc acgctcaccg gctccagatt tatcagcaat aaaccagcca gccggaaggg   7320
ccgagcgcag aagtggtcct gcaactttat ccgcctccat ccagtctatt aattgttgcc   7380
gggaagctag agtaagtagt tcgccagtta atagtttgcg caacgttgtt gccattgcta   7440
caggcatcgt ggtgtcacgc tcgtcgtttg gtatggcttc attcagctcc ggttcccaac   7500
gatcaaggcg agttacatga tcccccatgt tgtgcaaaaa agcggttagc tccttcggtc   7560
ctccgatcgt tgtcagaagt aagttggccg cagtgttatc actcatggtt atggcagcac   7620
```

tgcataattc tcttactgtc atgccatccg taagatgctt ttctgtgact ggtgagtact 7680
caaccaagtc attctgagaa tagtgtatgc ggcgaccgag ttgctcttgc ccggcgtcaa 7740
tacgggataa taccgcgcca catagcagaa ctttaaaagt gctcatcatt ggaaaacgtt 7800
cttcggggcg aaaactctca aggatcttac cgctgttgag atccagttcg atgtaaccca 7860
ctcgtgcacc caactgatct tcagcatctt ttactttcac cagcgtttct gggtgagcaa 7920
aaacaggaag gcaaaatgcc gcaaaaaagg gaataagggc gacacggaaa tgttgaatac 7980
tcatactctt cctttttcaa tattattgaa gcatttatca gggttattgt ctcatgagcg 8040
gatacatatt tgaatgtatt tagaaaaata aacaaatagg ggttccgcgc acatttcccc 8100
gaaaagtgcc acctgacgtc taagaaacca ttattatcat gacattaacc tataaaaata 8160
ggcgtatcac gaggcccttt cgtc 8184

<210> SEQ ID NO 12
<211> LENGTH: 8196
<212> TYPE: DNA
<213> ORGANISM: Artificial Sequence
<220> FEATURE:
<223> OTHER INFORMATION: Synthetic construct

<400> SEQUENCE: 12
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatatg cggtgtgaaa taccgcacag atgcgtaagg agaaaatacc gcatcaggcg 240
cctcctcaac ctgtatattc gtaaaccacg cccaatggga gctgtctcag gtttgttcct 300
gattggttac ggcgcgtttc gcatcattgt tgagtttttc cgccagcccg acgcgcagtt 360
taccggtgcc tgggtgcagt acatcagcat ggggcaaatt ctttccatcc cgatgattgt 420
cgcgggtgtg atcatgatgg tctgggcata tcgtcgcagc ccacagcaac acgtttcctg 480
aggaaccatg aaacagtatt tagaactgat gcaaaaagtg ctcgacgaag gcacacagaa 540
aaacgaccgt accggaaccg gaacgctttc catttttggt catcagatgc gttttaacct 600
gcaagatgga ttcccgctgg tgacaactaa acgttgccac ctgcgttcca tcatccatga 660
actgctgtgg tttctgcagg gcgacactaa cattgcttat ctacacgaaa acaatgtcac 720
catctgggac gaatgggccg atgaaaacgg cgacctcggg ccagtgtatg gtaaacagtg 780
gcgcgcctgg ccaacgccag atggtcgtca tattgaccag atcactacgg tactgaacca 840
gctgaaaaac gacccggatt cgcgccgcat tattgtttca gcgtggaacg taggcgaact 900
ggataaaatg gcgctggcac cgtgccatgc attcttccag ttctatgtgg cagacggcaa 960
actctcttgc cagctttatc agcgctcctg tgacgtcttc ctcggcctgc cgttcaacat 1020
tgccagctac gcgttattgg tgcatatgat ggcgcagcag tgcgatctgg aagtgggtga 1080
ttttgtctgg accggtggcg acacgcatct gtacagcaac catatggatc aaactcatct 1140
gcaattaagc cgcgaaccgc gtccgctgcc gaagttgatt atcaaacgta aacccgaatc 1200
catcttcgac taccgtttcg aagactttga gattgaaggc tacgatccgc atccgggcat 1260
taaagcgccg gtggctatct aattacgaaa catcctgcca gagccgacgc cagtgtgcgt 1320
cggttttttt accctccgtt aaattcttcg agacgccttc ccgaaggcgc cattcgccat 1380
tcaggctgcg caactgttgg gaagggcgat cggtgcgggc ctcttcgcta ttacgccagc 1440
tggcgaaagg gggatgtgct gcaaggcgat taagttgggt aacgccaggg ttttcccagt 1500

-continued

```
cacgacgttg taaaacgacg gccagtgcca agcttactgc tcacaagaaa aaaggcacgt   1560
catctgacgt gcctttttta tttgtactac cctgtacgat tactgcaggt cgacttattt   1620
tttccatatc tgttcaacct tttttaaatc ctccaaacag tcaatatcta aacttgagct   1680
ttcgtccatt aaaaaatgct tggttttgct ttgtaaaaag ctaggattgt ttaaaaattc   1740
ttttatcttt aaaatataaa ttgcaccatt gctcatataa gttttaggca atttttgcct   1800
tggcataaaa ggatattcat cattacaaat ccctgctaaa tcgccacaat cattacaaac   1860
aaaggctttt agaattttat tatcacattc gcttacgcta attagggcat ttgcattgct   1920
atttttataa agattaaaag cttcattaat atgaatattt gttcttagcg gtgaagtggg   1980
ttgtaaaaaa actacatctt cataatcttt ataaaatttt agagcatgta acagcacttt   2040
atcgcttgtg gtatcatctt gtgcaaggct aattgggcgt tttaaaatat caacattttg   2100
actttttgca taatttaaaa tttcatcact atcactgctt acaacaactt tactaatgct   2160
tttagcattt agtgcagctt tgatcgtgta gtaaattaaa ggtttattgt ttaataaaac   2220
caaattttta tttttaatac cctttgagcc accacgagca gggattattg ctaagctcat   2280
tttatatcct taaaaacttt ttgtgtgctg agtttaaaaa aatctccgct ttgtaaatat   2340
tcaaaaaata attttgagct atctaaaatc tctaacttag cgctaaataa atcttgtttt   2400
ttatgaatag tgttaatagc ttttagtatt tcatcactat ttgcattaac ttttagtgta   2460
ttttcattgc caagtcttcc attttgtctt gagccaacta aaatccctgc tgtttttaag   2520
tataaggcct cttttaaaat acaacttgaa ttacctatta taaaatcagc atttttttaac   2580
aaagttataa aatactcaaa tctaagcgat ggaaaaagct taaatctagg gttattttta   2640
aactcttcat agctttgcaa gattaattca aaacctaaat cattatttgg ataaataaca   2700
atataatttt tattactttg tatcagtgct tttactaaat tgtctgcttg atttttaatg   2760
ctagtaattt cagttgtaac aggatgaaac ataagcaaag cgtagttttc ataatttata   2820
tcataatatt tttttgcttc gctaagtgaa attttattat cgtttaaaag ttctaaatca   2880
ggcgaaccta tgataaaaat agatttttca tcttctccaa gctgcattaa acgccttttt   2940
gcaaactcat catttactaa atgaatatga gctagttttg atatagcgtg gcgtaagcta   3000
tcgtcaatag ttcctgaaat ctctccgcct tcaatatgcg ctactaagat attatttaat   3060
gctccaacaa tagctgctgc taaaggctca attctatctc catgtactac gattaaatca   3120
ggttttagct catttgcata ccttgaaaat ccatcaattg tagtagctaa agccttatca   3180
gtttgataat atttatcata atttataaat tcataaatat ttttaaagcc atttttataa   3240
agttctttaa ctgtatagcc aaaattttta cttaagtgca ttcctgttgc aaagatgtaa   3300
agttcaaatt cgcttgagtt ttgcaccctg tacattaaag atttaatctt agaataatca   3360
gccctagagc ctgttataaa aaggattttt ttcacgcaaa atcctcatag cttaactgag   3420
catcattttc tatatctctt aatgcttttt tgcctaaaat attttcaaat tcagccgcac   3480
taattccacc aagtccaggt cttttaaccc aaatattatc catagataaa acttcgcctt   3540
ttttaatatc tttaatgcta actacacttg caaaggcaaa atcaattgta acttgttctt   3600
gtttagccgc tttttttactt tcattatttc ctcttattat agccatttgc tcactttgta   3660
taattagctc ttttaaagcc tttgtatcca tagaacaaac tatatcaggg ccacttctat   3720
gcatactatc agtaaaatgt ctttcaagca cacaagctcc aagtacaact gcacctaaac   3780
acgcaagatt atctgttgtg tggtcgctta agcctaccat acaagaaaat tcttttttta   3840
```

-continued

```
actcaagcat agcgtttaat cttacaagat tatgcggggt tgggtaaaga ttggtcgtgt   3900
gcattaaaac aaaaggaatt tcattgtcta ataagatttt tacagttggt tttatacttt   3960
caatactatt cattcctgtg ctaactatca taggcttttt aaaggctgct atgtgtttaa   4020
taagcggata attattacac tcacctgaac caatcttaaa agcactaact cccatatctt   4080
ctaagcggtt cgcacctgca cgagaaaaag gtgtgctaag ataaacaaga cctaattttt   4140
ctgtgtattc tttaagtgct agctcatctt tataatccaa agcacatttt tgcataatct   4200
cataaatgct tatttttgca ttaccaggaa ttactttttt agcggcctta ctcatctcat   4260
cttcaacaat atgagtttga tgctttataa tcttagcacc tgcgctaaag gctgcatcta   4320
ccataatttt agctagttct aaactgccat tatgattaat gcctatttca ggtacgacta   4380
agggtgcttt ttcttcactt atgattatat tttgtatttt tatttctttc atttattttc   4440
ctccttagtc gacggtaccc ttaagccacc ccccagcgga acgacacttt aagatgcgta   4500
ttgccgccac ccccccaaaa cggcaggatc ttacgtttga tcttacgcag gatgttctta   4560
agacgattca caagaagctt ctcttcaata ttcttgaact caagcaactt ttcctcgata   4620
tttttgaact ctaaaagttt ctcctcgatg tttttaaatt ccagaagctt ctcctcaagg   4680
ggaagcgata caatcaggtc acttgtatag ccgatcggtt tatcaagcaa ctcgaagtgg   4740
tattttgctt gcgggttcag tgccaggatg tgacgaagcg gagagttcgg tgctaaggcg   4800
taaagttttg catacttttg acacaggcag attgtgaaca tgtcatagta aatgttgtgg   4860
caatcggcca tgtgattgct gaagtgctgg gactgactct catcgtagaa gtggccccag   4920
cttgacgcac caaagtcaat cccgaccaag taaatctcct tataccccaa aaccacggcc   4980
gacaacagca ttaagactcc ggcactcaat tctttactat aagtttttaa gtggtacttc   5040
acatggcgaa ggatttcctc atggccctta aaaaggctga atgtgtcaca aacaaatggg   5100
tagtgggcct tcaaataacc ctccaccgga aggatcgtct gataatcgcc gtcgaagtca   5160
tggcggtctg tcgagacact gcagaagaag cgttcgatgg aatattcacc gttgtccatc   5220
agatattgag ctgtttgcat ttgagaagat aacacacagg gattgaagaa tacgccttta   5280
atctcacgtc caaggtaata cttatcctcg aaataaaact gattacagcg aaagacttcg   5340
aaatccttgg gaaataaact atagtccagg tctttgatgg atggcccgtt ccccgcaata   5400
attaagggtt tcttcatatg tatatctcct tcttgaattc taacaattga ttgaatgtat   5460
gcaaataaat gcatacacca taggtgtggt ttaatttgat gcccttttc agggctggaa    5520
tgtgtaagag cggggttatt tatgctgttg tttttttgtt actcgggaag ggctttacct   5580
cttccgcata aacgcttcca tcagcgttta tagttaaaaa aatctttcgg aactggtttt   5640
gcgcttaccc caaccaacag gggatttgct gctttccatt gagcctgttt ctctgcgcga   5700
cgttcgcggc ggcgtgtttg tgcatccatc tggattctcc tgtcagttag ctttggtggt   5760
gtgtggcagt tgtagtcctg aacgaaaacc ccccgcgatt ggcacattgg cagctaatcc   5820
ggaatcgcac ttacggccaa tgcttcgttt cgtatcacac accccaaagc cttctgcttt   5880
gaatgctgcc cttcttcagg gcttaatttt taagagcgtc accttcatgg tggtcagtgc   5940
gtcctgctga tgtgctcagt atcaccgcca gtggtattta tgtcaacacc gccagagata   6000
atttatcacc gcagatggtt atctgtatgt tttttatatg aatttatttt ttgcaggggg   6060
gcattgtttg gtaggtgaga gatcaattct gcattaatga atcggccaac gcgcggggag   6120
aggcggtttg cgtattgggc gctcttccgc tgctagcgga gtgtatactg gcttactatg   6180
ttggcactga tgagggtgtc agtgaagtgc ttcatgtggc aggagaaaaa aggctgcacc   6240
```

-continued

```
ggtgcgtcag cagaatatgt gatacaggat atattccgct tcctcgctca ctgactcgct   6300

acgctcggtc gttcgactgc ggcgagcgga aatggcttac gaacggggcg gagatttcct   6360

ggaagatgcc aggaagatac ttaacaggga agtgagaggg ccgcggcaaa gccgtttttc   6420

cataggctcc gcccccctga caagcatcac gaaatctgac gctcaaatca gtggtggcga   6480

aacccgacag gactataaag ataccaggcg tttccccctg gcggctccct cgtgcgctct   6540

cctgttcctg cctttcggtt taccggtgtc attccgctgt tatggccgcg tttgtctcat   6600

tccacgcctg acactcagtt ccgggtaggc agttcgctcc aagctggact gtatgcacga   6660

accccccgtt cagtccgacc gctgcgcctt atccggtaac tatcgtcttg agtccaaccc   6720

ggaaagacat gcaaaagcac cactggcagc agccactggt aattgattta gaggagttag   6780

tcttgaagtc atgcgccggt taaggctaaa ctgaaaggac aagttttggt gactgcgctc   6840

ctccaagcca gttacctcgg ttcaaagagt tggtagctca gagaaccttc gaaaaaccgc   6900

cctgcaaggc ggtttttcg ttttcagagc aagagattac gcgcagacca aaacgatctc   6960

aagaagatca tcttattaat cagataaaat atttctaggc ggccgcgaac gaaaactcac   7020

gttaagggat tttggtcatg agattatcaa aaaggatctt cacctagatc cttttaaatt   7080

aaaaatgaag ttttaaatca atctaaagta tatatgagta aacttggtct gacagttacc   7140

aatgcttaat cagtgaggca cctatctcag cgatctgtct atttcgttca tccatagttg   7200

cctgactccc cgtcgtgtag ataactacga tacgggaggg cttaccatct ggccccagtg   7260

ctgcaatgat accgcgagac ccacgctcac cggctccaga tttatcagca ataaaccagc   7320

cagccggaag ggccgagcgc agaagtggtc ctgcaacttt atccgcctcc atccagtcta   7380

ttaattgttg ccgggaagct agagtaagta gttcgccagt taatagtttg cgcaacgttg   7440

ttgccattgc tacaggcatc gtggtgtcac gctcgtcgtt tggtatggct tcattcagct   7500

ccggttccca acgatcaagg cgagttacat gatcccccat gttgtgcaaa aaagcggtta   7560

gctccttcgg tcctccgatc gttgtcagaa gtaagttggc cgcagtgtta tcactcatgg   7620

ttatggcagc actgcataat tctcttactg tcatgccatc cgtaagatgc ttttctgtga   7680

ctggtgagta ctcaaccaag tcattctgag aatagtgtat gcggcgaccg agttgctctt   7740

gcccggcgtc aatacgggat aataccgcgc cacatagcag aactttaaaa gtgctcatca   7800

ttggaaaacg ttcttcgggg cgaaaactct caaggatctt accgctgttg agatccagtt   7860

cgatgtaacc cactcgtgca cccaactgat cttcagcatc ttttactttc accagcgttt   7920

ctgggtgagc aaaaacagga aggcaaaatg ccgcaaaaaa gggaataagg gcgacacgga   7980

aatgttgaat actcatactc ttcctttttc aatattattg aagcatttat cagggttatt   8040

gtctcatgag cggatacata tttgaatgta tttagaaaaa taaacaaata ggggttccgc   8100

gcacatttcc ccgaaaagtg ccacctgacg tctaagaaac cattattatc atgacattaa   8160

cctataaaaa taggcgtatc acgaggccct ttcgtc                             8196
```

<210> SEQ ID NO 13
<211> LENGTH: 385
<212> TYPE: PRT
<213> ORGANISM: Pasteurella dagmatis

<400> SEQUENCE: 13

```
Met Thr Ile Tyr Leu Asp Pro Ala Ser Leu Pro Thr Leu Asn Gln Leu
1               5                   10                  15

Met His Phe Thr Lys Glu Ser Glu Asp Lys Glu Thr Ala Arg Ile Phe
```

```
            20                  25                  30

Gly Phe Ser Arg Phe Lys Leu Pro Glu Lys Ile Thr Glu Gln Tyr Asn
        35                  40                  45

Asn Ile His Phe Val Glu Ile Lys Asn Asn Arg Pro Thr Glu Asp Ile
    50                  55                  60

Phe Thr Ile Leu Asp Gln Tyr Pro Glu Lys Leu Glu Leu Asp Leu His
65                  70                  75                  80

Leu Asn Ile Ala His Ser Ile Gln Leu Phe His Pro Ile Leu Gln Tyr
                85                  90                  95

Arg Phe Lys His Pro Asp Arg Ile Ser Ile Lys Ser Leu Asn Leu Tyr
            100                 105                 110

Asp Asp Gly Thr Met Glu Tyr Val Asp Leu Glu Lys Glu Glu Asn Lys
        115                 120                 125

Asp Ile Lys Ser Ala Ile Lys Lys Ala Glu Lys Gln Leu Ser Asp Tyr
    130                 135                 140

Leu Leu Thr Gly Lys Ile Asn Phe Asp Asn Pro Thr Leu Ala Arg Tyr
145                 150                 155                 160

Val Trp Gln Ser Gln Tyr Pro Val Lys Tyr His Phe Leu Ser Thr Glu
                165                 170                 175

Tyr Phe Glu Lys Ala Glu Phe Leu Gln Pro Leu Lys Thr Tyr Leu Ala
            180                 185                 190

Gly Lys Tyr Gln Lys Met Asp Trp Ser Ala Tyr Glu Lys Leu Ser Pro
        195                 200                 205

Glu Gln Gln Thr Phe Tyr Leu Lys Leu Val Gly Phe Ser Asp Glu Thr
    210                 215                 220

Lys Gln Leu Phe His Thr Glu Gln Thr Lys Phe Ile Phe Thr Gly Thr
225                 230                 235                 240

Thr Thr Trp Glu Gly Asn Thr Asp Ile Arg Glu Tyr Tyr Ala Lys Gln
                245                 250                 255

Gln Leu Asn Leu Leu Lys His Phe Thr His Ser Glu Gly Asp Leu Phe
            260                 265                 270

Ile Gly Asp Gln Tyr Lys Ile Tyr Phe Lys Gly His Pro Arg Gly Gly
        275                 280                 285

Asp Ile Asn Asp Tyr Ile Leu Lys His Ala Lys Asp Ile Thr Asn Ile
    290                 295                 300

Pro Ala Asn Ile Ser Phe Glu Ile Leu Met Met Thr Gly Leu Leu Pro
305                 310                 315                 320

Asp Lys Val Gly Gly Val Ala Ser Ser Leu Tyr Phe Ser Leu Pro Lys
                325                 330                 335

Glu Lys Ile Ser His Ile Ile Phe Thr Ser Asn Lys Lys Ile Lys Asn
            340                 345                 350

Lys Glu Asp Ala Leu Asn Asp Pro Tyr Val Arg Val Met Leu Arg Leu
        355                 360                 365

Gly Met Ile Asp Lys Ser Gln Ile Ile Phe Trp Asp Ser Leu Lys Gln
    370                 375                 380

Leu
385
```

<210> SEQ ID NO 14
<211> LENGTH: 385
<212> TYPE: PRT
<213> ORGANISM: Artificial Sequence
<220> FEATURE:
<223> OTHER INFORMATION: Mutant form of PdST.

```
<400> SEQUENCE: 14

Met Thr Ile Tyr Leu Asp His Ala Ser Leu Pro Thr Leu Asn Gln Leu
1               5                   10                  15

Met His Phe Thr Lys Glu Ser Glu Asp Lys Glu Thr Ala Arg Ile Phe
            20                  25                  30

Gly Phe Ser Arg Phe Lys Leu Pro Glu Lys Ile Thr Glu Gln Tyr Asn
        35                  40                  45

Asn Ile His Phe Val Glu Ile Lys Asn Asn Arg Pro Thr Glu Asp Ile
    50                  55                  60

Phe Thr Ile Leu Asp Gln Tyr Pro Glu Lys Leu Glu Leu Asp Leu His
65                  70                  75                  80

Leu Asn Ile Ala His Ser Ile Gln Leu Phe His Pro Ile Leu Gln Tyr
                85                  90                  95

Arg Phe Lys His Pro Asp Arg Ile Ser Ile Lys Ser Leu Asn Leu Tyr
            100                 105                 110

Asp Asp Gly Thr Ala Glu Tyr Val Asp Leu Glu Lys Glu Glu Asn Lys
        115                 120                 125

Asp Ile Lys Ser Ala Ile Lys Lys Ala Glu Lys Gln Leu Ser Asp Tyr
    130                 135                 140

Leu Leu Thr Gly Lys Ile Asn Phe Asp Asn Pro Thr Leu Ala Arg Tyr
145                 150                 155                 160

Val Trp Gln Ser Gln Tyr Pro Val Lys Tyr His Phe Leu Ser Thr Glu
                165                 170                 175

Tyr Phe Glu Lys Ala Glu Phe Leu Gln Pro Leu Lys Thr Tyr Leu Ala
            180                 185                 190

Gly Lys Tyr Gln Lys Met Asp Trp Ser Ala Tyr Glu Lys Leu Ser Pro
        195                 200                 205

Glu Gln Gln Thr Phe Tyr Leu Lys Leu Val Gly Phe Ser Asp Glu Thr
    210                 215                 220

Lys Gln Leu Phe His Thr Glu Gln Thr Lys Phe Ile Phe Thr Gly Thr
225                 230                 235                 240

Thr Thr Trp Glu Gly Asn Thr Asp Ile Arg Glu Tyr Tyr Ala Lys Gln
                245                 250                 255

Gln Leu Asn Leu Leu Lys His Phe Thr His Ser Glu Gly Asp Leu Phe
            260                 265                 270

Ile Gly Asp Gln Tyr Lys Ile Tyr Phe Lys Gly His Pro Arg Gly Gly
        275                 280                 285

Asp Ile Asn Asp Tyr Ile Leu Lys His Ala Lys Asp Ile Thr Asn Ile
    290                 295                 300

Pro Ala Asn Ile Ser Phe Glu Ile Leu Met Met Thr Gly Leu Leu Pro
305                 310                 315                 320

Asp Lys Val Gly Gly Val Ala Ser Ser Leu Tyr Phe Ser Leu Pro Lys
                325                 330                 335

Glu Lys Ile Ser His Ile Ile Phe Thr Ser Asn Lys Lys Ile Lys Asn
            340                 345                 350

Lys Glu Asp Ala Leu Asn Asp Pro Tyr Val Arg Val Met Leu Arg Leu
        355                 360                 365

Gly Met Ile Asp Lys Ser Gln Ile Ile Phe Trp Asp Ser Leu Lys Gln
    370                 375                 380

Leu
385

<210> SEQ ID NO 15
```

<211> LENGTH: 397
<212> TYPE: PRT
<213> ORGANISM: Artificial Sequence
<220> FEATURE:
<223> OTHER INFORMATION: Mutant form of PdST

<400> SEQUENCE: 15

```
Met Glu Ile Tyr Leu Asp His Ala Ser Leu Pro Ser Leu Asn Met Ile
1               5                   10                  15

Leu Asn Leu Val Glu Asn Lys Asn Asn Glu Lys Val Glu Arg Ile Ile
            20                  25                  30

Gly Phe Glu Arg Phe Asp Phe Asn Lys Glu Ile Leu Asn Ser Phe Ser
        35                  40                  45

Lys Glu Arg Ile Glu Phe Ser Lys Val Ser Ile Leu Asp Ile Lys Glu
    50                  55                  60

Phe Ser Asp Lys Leu Tyr Leu Asn Ile Glu Lys Ser Asp Thr Pro Val
65                  70                  75                  80

Asp Leu Ile Ile His Thr Asn Leu Asp His Ser Val Arg Ser Leu Leu
                85                  90                  95

Ser Ile Phe Lys Thr Leu Ser Pro Leu Phe His Lys Ile Asn Ile Glu
            100                 105                 110

Lys Leu Tyr Leu Tyr Asp Asp Gly Ser Ala Asn Tyr Val Asp Leu Tyr
        115                 120                 125

Gln His Arg Gln Glu Asn Ile Ser Ala Ile Leu Ile Glu Ala Gln Lys
    130                 135                 140

Lys Leu Lys Asp Ala Leu Glu Asn Arg Glu Thr Asp Thr Asp Lys Leu
145                 150                 155                 160

His Ser Leu Thr Arg Tyr Thr Trp His Lys Ile Phe Pro Thr Glu Tyr
                165                 170                 175

Ile Leu Leu Arg Pro Asp Tyr Leu Asp Ile Asp Glu Lys Met Gln Pro
            180                 185                 190

Leu Lys His Phe Leu Ser Asp Thr Ile Val Ser Met Asp Leu Ser Arg
        195                 200                 205

Phe Ser His Phe Ser Lys Asn Gln Lys Glu Leu Phe Leu Lys Ile Thr
    210                 215                 220

His Phe Asp Gln Asn Ile Phe Asn Glu Leu Asn Ile Gly Thr Lys Asn
225                 230                 235                 240

Lys Glu Tyr Lys Thr Phe Ile Phe Thr Gly Thr Thr Thr Trp Glu Lys
                245                 250                 255

Asp Lys Lys Lys Arg Leu Asn Asn Ala Lys Leu Gln Thr Glu Ile Leu
            260                 265                 270

Glu Ser Phe Ile Lys Pro Asn Gly Lys Phe Tyr Leu Gly Asn Asp Ile
        275                 280                 285

Lys Ile Phe Phe Lys Gly His Pro Lys Gly Asp Asp Ile Asn Asp Tyr
    290                 295                 300

Ile Ile Arg Lys Thr Gly Ala Glu Lys Ile Pro Ala Asn Ile Pro Phe
305                 310                 315                 320

Glu Val Leu Met Met Thr Asn Ser Leu Pro Asp Tyr Val Gly Gly Ile
                325                 330                 335

Met Ser Thr Val Tyr Phe Ser Leu Pro Pro Lys Asn Ile Asp Lys Val
            340                 345                 350

Val Phe Leu Gly Ser Glu Lys Ile Lys Asn Glu Asn Asp Ala Lys Ser
        355                 360                 365

Gln Thr Leu Ser Lys Leu Met Leu Met Leu Asn Val Ile Thr Pro Glu
    370                 375                 380
```

-continued

```
Gln Ile Phe Phe Glu Glu Met Pro Asn Pro Ile Asn Phe
385                 390                 395
```

<210> SEQ ID NO 16
<211> LENGTH: 399
<212> TYPE: PRT
<213> ORGANISM: Artificial Sequence
<220> FEATURE:
<223> OTHER INFORMATION: Mutant form of BstE

<400> SEQUENCE: 16

```
Met Leu Ile Gln Gln Asn Leu Glu Ile Tyr Leu Asp His Ala Thr Ile
1               5                   10                  15

Pro Ser Leu Ala Cys Phe Met His Phe Ile Gln His Lys Asp Asp Val
            20                  25                  30

Asp Ser Ile Arg Leu Phe Gly Leu Ala Arg Phe Asp Ile Pro Gln Ser
        35                  40                  45

Ile Ile Asp Arg Tyr Pro Ala Asn His Leu Phe Tyr His Asn Ile Asp
    50                  55                  60

Asn Arg Asp Leu Thr Ala Val Leu Asn Gln Leu Ala Asp Ile Leu Ala
65                  70                  75                  80

Gln Glu Asn Lys Arg Phe Gln Ile Asn Leu His Leu Asn Leu Phe His
                85                  90                  95

Ser Ile Asp Leu Phe Phe Ala Ile Tyr Pro Ile Tyr Gln Gln Tyr Gln
            100                 105                 110

His Lys Ile Ser Thr Ile Gln Leu Gln Leu Tyr Asp Asp Gly Ser Ala
        115                 120                 125

Gly Ile Val Thr Gln His Ser Leu Cys Lys Ile Ala Asp Leu Glu Gln
    130                 135                 140

Leu Ile Leu Gln His Lys Asn Val Leu Leu Glu Leu Leu Thr Lys Gly
145                 150                 155                 160

Thr Ala Asn Val Pro Asn Pro Thr Leu Leu Arg Tyr Leu Trp Asn Asn
                165                 170                 175

Ile Ile Asp Ser Gln Phe His Leu Ile Ser Asp His Phe Leu Gln His
            180                 185                 190

Pro Lys Leu Gln Pro Leu Lys Arg Leu Leu Lys Arg Tyr Thr Ile Leu
        195                 200                 205

Asp Phe Thr Cys Tyr Pro Arg Phe Asn Ala Glu Gln Lys Gln Leu Leu
    210                 215                 220

Lys Glu Ile Leu His Ile Ser Asn Glu Leu Glu Asn Leu Leu Lys Leu
225                 230                 235                 240

Leu Lys Gln His Asn Thr Phe Leu Phe Thr Gly Thr Thr Ala Phe Asn
                245                 250                 255

Leu Asp Gln Glu Lys Leu Asp Leu Leu Thr Gln Leu His Ile Leu Leu
            260                 265                 270

Leu Asn Glu His Gln Asn Pro His Ser Thr His Tyr Ile Gly Asn Asn
        275                 280                 285

Tyr Leu Leu Leu Ile Lys Gly His Ala Asn Ser Pro Ala Leu Asn His
    290                 295                 300

Thr Leu Ala Leu His Phe Pro Asp Ala Ile Phe Leu Pro Ala Asn Ile
305                 310                 315                 320

Pro Phe Glu Ile Phe Ala Met Leu Gly Phe Thr Pro Asn Lys Met Gly
                325                 330                 335

Gly Phe Ala Ser Thr Ser Tyr Ile Asn Tyr Pro Thr Glu Asn Ile Asn
            340                 345                 350
```

-continued

His Leu Phe Phe Leu Thr Ser Asp Gln Pro Ser Ile Arg Thr Lys Trp
        355                 360                 365

Leu Asp Tyr Glu Lys Gln Phe Gly Leu Met Tyr Ser Leu Leu Ala Met
    370                 375                 380

Gln Lys Ile Asn Glu Asp Gln Ala Phe Met Cys Thr Ile His Asn
385                 390                 395

<210> SEQ ID NO 17
<211> LENGTH: 8433
<212> TYPE: DNA
<213> ORGANISM: Artificial Sequence
<220> FEATURE:
<223> OTHER INFORMATION: Synthetic construct

<400> SEQUENCE: 17
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatatg cggtgtgaaa taccgcacag atgcgtaagg agaaaatacc gcatcaggcg 240
cctcctcaac ctgtatattc gtaaaccacg cccaatggga gctgtctcag gtttgttcct 300
gattggttac ggcgcgtttc gcatcattgt tgagtttttc cgccagcccg acgcgcagtt 360
taccggtgcc tgggtgcagt acatcagcat ggggcaaatt ctttccatcc cgatgattgt 420
cgcgggtgtg atcatgatgg tctgggcata tcgtcgcagc ccacagcaac acgtttcctg 480
aggaaccatg aaacagtatt tagaactgat gcaaaaagtg ctcgacgaag gcacacagaa 540
aaacgaccgt accggaaccg gaacgctttc catttttggt catcagatgc gttttaacct 600
gcaagatgga ttcccgctgg tgacaactaa acgttgccac ctgcgttcca tcatccatga 660
actgctgtgg tttctgcagg gcgacactaa cattgcttat ctacacgaaa acaatgtcac 720
catctgggac gaatgggccg atgaaaacgg cgacctcggg ccagtgtatg gtaaacagtg 780
gcgcgcctgg ccaacgccag atggtcgtca tattgaccag atcactacgg tactgaacca 840
gctgaaaaac gacccggatt cgcgccgcat tattgtttca gcgtggaacg taggcgaact 900
ggataaaatg gcgctggcac cgtgccatgc attcttccag ttctatgtgg cagacggcaa 960
actctcttgc cagctttatc agcgctcctg tgacgtcttc ctcggcctgc cgttcaacat 1020
tgccagctac gcgttattgg tgcatatgat ggcgcagcag tgcgatctgg aagtgggtga 1080
ttttgtctgg accggtggcg acacgcatct gtacagcaac catatggatc aaactcatct 1140
gcaattaagc cgcgaaccgc gtccgctgcc gaagttgatt atcaaacgta aacccgaatc 1200
catcttcgac taccgtttcg aagactttga gattgaaggc tacgatccgc atccgggcat 1260
taaagcgccg gtggctatct aattacgaaa catcctgcca gagccgacgc cagtgtgcgt 1320
cggttttttt accctccgtt aaattcttcg agacgccttc ccgaaggcgc cattcgccat 1380
tcaggctgcg caactgttgg gaagggcgat cggtgcgggc ctcttcgcta ttacgccagc 1440
tggcgaaagg gggatgtgct gcaaggcgat taagttgggt aacgccaggg ttttcccagt 1500
cacgacgttg taaaacgacg gccagtgcca agcttactgc tcacaagaaa aaaggcacgt 1560
catctgacgt gccttttta tttgtactac cctgtacgat tactgcaggt cgacttattt 1620
tttccatatc tgttcaacct tttttaaatc ctccaaacag tcaatatcta aacttgagct 1680
ttcgtccatt aaaaaatgct tggttttgct ttgtaaaaag ctaggattgt ttaaaaattc 1740
ttttatcttt aaaatataaa ttgcaccatt gctcatataa gttttaggca atttttgcct 1800

```
tggcataaaa ggatattcat cattacaaat ccctgctaaa tcgccacaat cattacaaac   1860
aaaggctttt agaattttat tatcacattc gcttacgcta attagggcat ttgcattgct   1920
atttttataa agattaaaag cttcattaat atgaatattt gttcttagcg gtgaagtggg   1980
ttgtaaaaaa actacatctt cataatcttt ataaaatttt agagcatgta acagcacttt   2040
atcgcttgtg gtatcatctt gtgcaaggct aattgggcgt tttaaaatat caacattttg   2100
actttttgca taatttaaaa tttcatcact atcactgctt acaacaactt tactaatgct   2160
tttagcattt agtgcagctt tgatcgtgta gtaaattaaa ggtttattgt ttaataaaac   2220
caaattttta tttttaatac cctttgagcc accacgagca gggattattg ctaagctcat   2280
tttatatcct taaaaacttt ttgtgtgctg agtttaaaaa aatctccgct ttgtaaatat   2340
tcaaaaaata attttgagct atctaaaatc tctaacttag cgctaaataa atcttgtttt   2400
ttatgaatag tgttaatagc ttttagtatt tcatcactat ttgcattaac ttttagtgta   2460
ttttcattgc caagtcttcc attttgtctt gagccaacta aaatccctgc tgtttttaag   2520
tataaggcct cttttaaaat acaacttgaa ttacctatta taaaatcagc atttttttaac  2580
aaagttataa aatactcaaa tctaagcgat ggaaaaagct taaatctagg gttattttta   2640
aactcttcat agctttgcaa gattaattca aaacctaaat cattatttgg ataaataaca   2700
atataatttt tattactttg tatcagtgct tttactaaat tgtctgcttg atttttaatg   2760
ctagtaattt cagttgtaac aggatgaaac ataagcaaag cgtagttttc ataatttata   2820
tcataatatt tttttgcttc gctaagtgaa attttattat cgtttaaaag ttctaaatca   2880
ggcgaaccta tgataaaaat agatttttca tcttctccaa gctgcattaa acgccttttt   2940
gcaaactcat catttactaa atgaatatga gctagttttg atatagcgtg gcgtaagcta   3000
tcgtcaatag ttcctgaaat ctctccgcct tcaatatgcg ctactaagat attatttaat   3060
gctccaacaa tagctgctgc taaaggctca attctatctc catgtactac gattaaatca   3120
ggttttagct catttgcata ccttgaaaat ccatcaattg tagtagctaa agccttatca   3180
gtttgataat atttatcata atttataaat tcataaatat ttttaaagcc atttttataa   3240
agttctttaa ctgtatagcc aaaattttta cttaagtgca ttcctgttgc aaagatgtaa   3300
agttcaaatt cgcttgagtt ttgcaccctg tacattaaag atttaatctt agaataatca   3360
gccctagagc ctgttataaa aaggattttt ttcacgcaaa atcctcatag cttaactgag   3420
catcattttc tatatctctt aatgcttttt tgcctaaaat attttcaaat tcagccgcac   3480
taattccacc aagtccaggt cttttaaccc aaatattatc catagataaa acttcgcctt   3540
ttttaatatc tttaatgcta actacacttg caaaggcaaa atcaattgta acttgttctt   3600
gtttagccgc tttttttactt tcattatttc ctcttattat agccatttgc tcactttgta  3660
taattagctc ttttaaagcc tttgtatcca tagaacaaac tatatcaggg ccacttctat   3720
gcatactatc agtaaaatgt ctttcaagca cacaagctcc aagtacaact gcacctaaac   3780
acgcaagatt atctgttgtg tggtcgctta agcctaccat acaagaaaat tcttttttta   3840
actcaagcat agcgtttaat cttacaagat tatgcggggt tgggtaaaga ttggtcgtgt   3900
gcattaaaac aaaaggaatt tcattgtcta ataagatttt tacagttggt tttatacttt   3960
caatactatt cattcctgtg ctaactatca taggcttttt aaaggctgct atgtgtttaa   4020
taagcggata attattacac tcacctgaac caatcttaaa agcactaact cccatatctt   4080
ctaagcggtt cgcacctgca cgagaaaaag gtgtgctaag ataaacaaga cctaattttt   4140
```

ctgtgtattc tttaagtgct agctcatctt tataatccaa agcacatttt tgcataatct 4200
cataaatgct tatttttgca ttaccaggaa ttactttttt agcggcctta ctcatctcat 4260
cttcaacaat atgagtttga tgctttataa tcttagcacc tgcgctaaag gctgcatcta 4320
ccataatttt agctagttct aaactgccat tatgattaat gcctatttca ggtacgacta 4380
agggtgcttt ttcttcactt atgattatat tttgtatttt tatttctttc atttattttc 4440
ctccttagtc gacggtacac ttaaaagttg atcggattcg gcatttcttc aaaaaaaatc 4500
tgttccggag taataacgtt cagcatcagc atcagtttgc tcagggtctg ggatttggca 4560
tcgttttcat ttttgatttt ttcggagccc aggaatacta ctttatcgat gtttttcggt 4620
ggcaggctaa agtacacggt agacatgatg ccacctacat agtccggcag agagttggtc 4680
atcatcagaa cttcgaacgg gatgttggcc gggatttttt ccgcaccggt tttgcggata 4740
atatagtcgt tgatatcgtc gcctttcggg tggcctttga agaagatttt aatgtcgtta 4800
cccagataga atttgccgtt cggtttgata aaggattcca ggatttccgt ctgcagtttc 4860
gcgttgttca gacgtttttt tttatctttc tcccaggtgg tggtaccggt gaagatgaaa 4920
gttttatatt ctttgttttt ggtaccaatg ttcagttcgt tgaagatgtt ctgatcaaag 4980
tgagtaattt tcaggaacag ttctttctgg ttcttagaga agtgagaaaa gcggctcaga 5040
tccatgctaa caatggtgtc agacaggaaa tgcttcagcg gctgcatctt ttcgtcgata 5100
tccagatagt ccgggcgcag cagaatgtat tcggtcggaa aaatcttgtg ccaagtgtaa 5160
cgggtcagag aatgcagttt gtcggtatca gtttcacggt tctccagtgc gtccttcagc 5220
tttttctgtg cttcgatcag gattgcgctg atgttttcct gacgatgctg atacagatct 5280
acgtagttac cagagccgtc gtcgtacaga tacagctttt cgatgttgat cttgtggaac 5340
agcggggaca gggttttgaa aatagacagc agagaacgaa cagaatgatc caggttagtg 5400
tgaataatca ggtccaccgg ggtatcgctt ttttcgatgt tcaggtacag tttgtcgctg 5460
aactccttaa tgtccagaat gctcactttg gagaactcga tgcgctcttt ggagaaagag 5520
ttcagaattt ctttgttgaa atcgaagcgt tcaaaaccga tgatacgttc cactttctca 5580
ttatttttgt tttcaaccag attcaggatc atgttcaggc taggcaggga tgcgtagtcc 5640
aggtaaattt ccatatgtat atctccttct tgaattctaa caattgattg aatgtatgca 5700
aataaatgca tacaccatag gtgtggttta atttgatgcc ctttttcagg gctggaatgt 5760
gtaagagcgg ggttatttat gctgttgttt ttttgttact cgggaagggc tttacctctt 5820
ccgcataaac gcttccatca gcgtttatag ttaaaaaaat ctttcggaac tggttttgcg 5880
cttaccccaa ccaacagggg atttgctgct ttccattgag cctgtttctc tgcgcgacgt 5940
tcgcggcggc gtgtttgtgc atccatctgg attctcctgt cagttagctt tggtggtgtg 6000
tggcagttgt agtcctgaac gaaaaccccc cgcgattggc acattggcag ctaatccgga 6060
atcgcactta cggccaatgc ttcgtttcgt atcacacacc ccaaagcctt ctgctttgaa 6120
tgctgccctt cttcagggct taatttttaa gagcgtcacc ttcatggtgg tcagtgcgtc 6180
ctgctgatgt gctcagtatc accgccagtg gtatttatgt caacaccgcc agagataatt 6240
tatcaccgca gatggttatc tgtatgtttt ttatatgaat ttattttttg caggggggca 6300
ttgtttggta ggtgagagat caattctgca ttaatgaatc ggccaacgcg cggggagagg 6360
cggtttgcgt attgggcgct cttccgctgc tagcggagtg tatactggct tactatgttg 6420
gcactgatga gggtgtcagt gaagtgcttc atgtggcagg agaaaaaagg ctgcaccggt 6480
gcgtcagcag aatatgtgat acaggatata ttccgcttcc tcgctcactg actcgctacg 6540

-continued

```
ctcggtcgtt cgactgcggc gagcggaaat ggcttacgaa cggggcggag atttcctgga   6600

agatgccagg aagatactta acagggaagt gagagggccg cggcaaagcc gtttttccat   6660

aggctccgcc cccctgacaa gcatcacgaa atctgacgct caaatcagtg gtggcgaaac   6720

ccgacaggac tataaagata ccaggcgttt ccccctggcg gctccctcgt gcgctctcct   6780

gttcctgcct ttcggtttac cggtgtcatt ccgctgttat ggccgcgttt gtctcattcc   6840

acgcctgaca ctcagttccg ggtaggcagt tcgctccaag ctggactgta tgcacgaacc   6900

ccccgttcag tccgaccgct gcgccttatc cggtaactat cgtcttgagt ccaacccgga   6960

aagacatgca aaagcaccac tggcagcagc cactggtaat tgatttagag gagttagtct   7020

tgaagtcatg cgccggttaa ggctaaactg aaaggacaag ttttggtgac tgcgctcctc   7080

caagccagtt acctcggttc aaagagttgg tagctcagag aaccttcgaa aaaccgccct   7140

gcaaggcggt tttttcgttt tcagagcaag agattacgcg cagaccaaaa cgatctcaag   7200

aagatcatct tattaatcag ataaaatatt tctaggcggc cgcgaacgaa aactcacgtt   7260

aagggatttt ggtcatgaga ttatcaaaaa ggatcttcac ctagatcctt ttaaattaaa   7320

aatgaagttt taaatcaatc taaagtatat atgagtaaac ttggtctgac agttaccaat   7380

gcttaatcag tgaggcacct atctcagcga tctgtctatt tcgttcatcc atagttgcct   7440

gactccccgt cgtgtagata actacgatac gggagggctt accatctggc cccagtgctg   7500

caatgatacc gcgagaccca cgctcaccgg ctccagattt atcagcaata aaccagccag   7560

ccggaagggc cgagcgcaga agtggtcctg caactttatc cgcctccatc cagtctatta   7620

attgttgccg ggaagctaga gtaagtagtt cgccagttaa tagtttgcgc aacgttgttg   7680

ccattgctac aggcatcgtg gtgtcacgct cgtcgtttgg tatggcttca ttcagctccg   7740

gttcccaacg atcaaggcga gttacatgat cccccatgtt gtgcaaaaaa gcggttagct   7800

ccttcggtcc tccgatcgtt gtcagaagta agttggccgc agtgttatca ctcatggtta   7860

tggcagcact gcataattct cttactgtca tgccatccgt aagatgcttt tctgtgactg   7920

gtgagtactc aaccaagtca ttctgagaat agtgtatgcg gcgaccgagt tgctcttgcc   7980

cggcgtcaat acgggataat accgcgccac atagcagaac tttaaaagtg ctcatcattg   8040

gaaaacgttc ttcggggcga aaactctcaa ggatcttacc gctgttgaga tccagttcga   8100

tgtaacccac tcgtgcaccc aactgatctt cagcatcttt tactttcacc agcgtttctg   8160

ggtgagcaaa aacaggaagg caaaatgccg caaaaaaggg aataagggcg acacggaaat   8220

gttgaatact catactcttc ctttttcaat attattgaag catttatcag ggttattgtc   8280

tcatgagcgg atacatattt gaatgtattt agaaaaataa acaaataggg gttccgcgca   8340

catttccccg aaaagtgcca cctgacgtct aagaaaccat tattatcatg acattaacct   8400

ataaaaatag gcgtatcacg aggccctttc gtc                                8433
```

<210> SEQ ID NO 18
<211> LENGTH: 397
<212> TYPE: PRT
<213> ORGANISM: Artificial Sequence
<220> FEATURE:
<223> OTHER INFORMATION: Mutant version of BstC

<400> SEQUENCE: 18

```
Met Glu Ile Tyr Leu Asp Tyr Ala Ser Leu Pro Ser Leu Asn Met Ile
1               5                   10                  15

Leu Asn Leu Val Glu Asn Lys Asn Asn Glu Lys Val Glu Arg Ile Ile
```

```
            20                  25                  30

Gly Phe Glu Arg Phe Asp Phe Asn Lys Glu Ile Leu Asn Ser Phe Ser
        35                  40                  45

Lys Glu Arg Ile Glu Phe Ser Lys Val Ser Ile Leu Asp Ile Lys Glu
    50                  55                  60

Phe Ser Asp Lys Leu Tyr Leu Asn Ile Glu Lys Ser Asp Thr Pro Val
65                  70                  75                  80

Asp Leu Ile Ile His Thr Asn Leu Asp His Ser Val Arg Ser Leu Leu
                85                  90                  95

Ser Ile Phe Lys Thr Leu Ser Pro Leu Phe His Lys Ile Asn Ile Glu
            100                 105                 110

Lys Leu Tyr Leu Tyr Asp Asp Gly Ser Gly Asn Tyr Val Asp Leu Tyr
        115                 120                 125

Gln His Arg Gln Glu Asn Ile Ser Ala Ile Leu Ile Glu Ala Gln Lys
    130                 135                 140

Lys Leu Lys Asp Ala Leu Glu Asn Arg Glu Thr Asp Thr Asp Lys Leu
145                 150                 155                 160

His Ser Leu Thr Arg Tyr Thr Trp His Lys Ile Phe Pro Thr Glu Tyr
                165                 170                 175

Ile Leu Leu Arg Pro Asp Tyr Leu Asp Ile Asp Glu Lys Met Gln Pro
            180                 185                 190

Leu Lys His Phe Leu Ser Asp Thr Ile Val Ser Met Asp Leu Ser Arg
        195                 200                 205

Phe Ser His Phe Ser Lys Asn Gln Lys Glu Leu Phe Leu Lys Ile Thr
    210                 215                 220

His Phe Asp Gln Asn Ile Phe Asn Glu Leu Asn Ile Gly Thr Lys Asn
225                 230                 235                 240

Lys Glu Tyr Lys Thr Phe Ile Phe Thr Gly Thr Thr Thr Trp Glu Lys
                245                 250                 255

Asp Lys Lys Lys Arg Leu Asn Asn Ala Lys Leu Gln Thr Glu Ile Leu
            260                 265                 270

Glu Ser Phe Ile Lys Pro Asn Gly Lys Phe Tyr Leu Gly Asn Asp Ile
        275                 280                 285

Lys Ile Phe Phe Lys Gly His Pro Lys Gly Asp Asp Ile Asn Asp Tyr
    290                 295                 300

Ile Ile Arg Lys Thr Gly Ala Glu Lys Ile Pro Ala Asn Ile Pro Phe
305                 310                 315                 320

Glu Val Leu Met Met Thr Asn Ser Leu Pro Asp Tyr Val Gly Gly Ile
                325                 330                 335

Met Ser Thr Val Tyr Phe Ser Leu Pro Pro Lys Asn Ile Asp Lys Val
            340                 345                 350

Val Phe Leu Gly Ser Glu Lys Ile Lys Asn Glu Asn Asp Ala Lys Ser
        355                 360                 365

Gln Thr Leu Ser Lys Leu Met Leu Met Leu Asn Val Ile Thr Pro Glu
    370                 375                 380

Gln Ile Phe Phe Glu Glu Met Pro Asn Pro Ile Asn Phe
385                 390                 395
```

<210> SEQ ID NO 19
<211> LENGTH: 417
<212> TYPE: PRT
<213> ORGANISM: Artificial Sequence
<220> FEATURE:
<223> OTHER INFORMATION: Mutant version of BstC

<400> SEQUENCE: 19

```
Met Arg Lys Ile Ile Thr Phe Phe Ser Leu Phe Phe Ser Ile Ser Ala
1               5                   10                  15

Trp Cys Gln Lys Met Glu Ile Tyr Leu Asp Tyr His Ser Leu Pro Ser
            20                  25                  30

Leu Asn Met Ile Leu Asn Leu Val Glu Asn Lys Asn Asn Glu Lys Val
        35                  40                  45

Glu Arg Ile Ile Gly Phe Glu Arg Phe Asp Phe Asn Lys Glu Ile Leu
    50                  55                  60

Asn Ser Phe Ser Lys Glu Arg Ile Glu Phe Ser Lys Val Ser Ile Leu
65                  70                  75                  80

Asp Ile Lys Glu Phe Ser Asp Lys Leu Tyr Leu Asn Ile Glu Lys Ser
                85                  90                  95

Asp Thr Pro Val Asp Leu Ile Ile His Thr Asn Leu Asp His Ser Val
            100                 105                 110

Arg Ser Leu Leu Ser Ile Phe Lys Thr Leu Ser Pro Leu Phe His Lys
        115                 120                 125

Ile Asn Ile Glu Lys Leu Tyr Leu Tyr Asp Asp Gly Ser Ala Asn Tyr
    130                 135                 140

Val Asp Leu Tyr Gln His Arg Gln Glu Asn Ile Ser Ala Ile Leu Ile
145                 150                 155                 160

Glu Ala Gln Lys Lys Leu Lys Asp Ala Leu Glu Asn Arg Glu Thr Asp
                165                 170                 175

Thr Asp Lys Leu His Ser Leu Thr Arg Tyr Thr Trp His Lys Ile Phe
            180                 185                 190

Pro Thr Glu Tyr Ile Leu Leu Arg Pro Asp Tyr Leu Asp Ile Asp Glu
        195                 200                 205

Lys Met Gln Pro Leu Lys His Phe Leu Ser Asp Thr Ile Val Ser Met
    210                 215                 220

Asp Leu Ser Arg Phe Ser His Phe Ser Lys Asn Gln Lys Glu Leu Phe
225                 230                 235                 240

Leu Lys Ile Thr His Phe Asp Gln Asn Ile Phe Asn Glu Leu Asn Ile
                245                 250                 255

Gly Thr Lys Asn Lys Glu Tyr Lys Thr Phe Ile Phe Thr Gly Thr Thr
            260                 265                 270

Thr Trp Glu Lys Asp Lys Lys Lys Arg Leu Asn Asn Ala Lys Leu Gln
        275                 280                 285

Thr Glu Ile Leu Glu Ser Phe Ile Lys Pro Asn Gly Lys Phe Tyr Leu
    290                 295                 300

Gly Asn Asp Ile Lys Ile Phe Phe Lys Gly His Pro Lys Gly Asp Asp
305                 310                 315                 320

Ile Asn Asp Tyr Ile Ile Arg Lys Thr Gly Ala Glu Lys Ile Pro Ala
                325                 330                 335

Asn Ile Pro Phe Glu Val Leu Met Met Thr Asn Ser Leu Pro Asp Tyr
            340                 345                 350

Val Gly Gly Ile Met Ser Thr Val Tyr Phe Ser Leu Pro Pro Lys Asn
        355                 360                 365

Ile Asp Lys Val Val Phe Leu Gly Ser Glu Lys Ile Lys Asn Glu Asn
    370                 375                 380

Asp Ala Lys Ser Gln Thr Leu Ser Lys Leu Met Leu Met Leu Asn Val
385                 390                 395                 400

Ile Thr Pro Glu Gln Ile Phe Phe Glu Glu Met Pro Asn Pro Ile Asn
                405                 410                 415
```

Phe

<210> SEQ ID NO 20
<211> LENGTH: 264
<212> TYPE: PRT
<213> ORGANISM: Artificial Sequence
<220> FEATURE:
<223> OTHER INFORMATION: Mutant version of BstD

<400> SEQUENCE: 20

```
Met Phe Lys Ile Lys Ser Tyr Gly Lys Asn Pro Gln Leu Gln Ala Val
1               5                   10                  15

Asp Ile Tyr Ile Asp His Ala Thr Ile Pro Ser Leu Ser Tyr Phe Leu
            20                  25                  30

His Phe Leu Lys His Lys His Asp His Gln Arg Leu Arg Leu Phe Ser
        35                  40                  45

Leu Ala Arg Phe Glu Met Pro Gln Thr Val Ile Glu Gln Tyr Glu Gly
    50                  55                  60

Ile Ile Gln Phe Ser Arg Asn Val Glu His Asn Val Glu Pro Leu Leu
65                  70                  75                  80

Glu Gln Leu Gln Thr Ile Leu Ser Gln Glu Gly Lys Gln Phe Glu Leu
                85                  90                  95

His Leu His Leu Asn Leu Phe His Ser Phe Glu Met Phe Leu Asn Leu
            100                 105                 110

Ser Pro Thr Tyr Thr Lys Tyr Lys Glu Lys Ile Ser Lys Ile Val Leu
        115                 120                 125

His Leu Tyr Asp Asp Gly Ser Ala Gly Val Met Lys Gln Tyr Gln Leu
    130                 135                 140

Gln Lys Ser Ser Ser Leu Val Gln Asp Leu Ala Ala Thr Lys Ala Ser
145                 150                 155                 160

Leu Val Ser Leu Phe Glu Asn Gly Glu Gly Ser Phe Ser Gln Ile Asp
                165                 170                 175

Leu Ile Arg Tyr Val Trp Asn Ala Val Leu Glu Thr His Tyr Tyr Leu
            180                 185                 190

Leu Ser Asp His Phe Leu Leu Asp Glu Lys Leu Gln Pro Leu Lys Ala
        195                 200                 205

Glu Leu Gly His Tyr Gln Leu Leu Asn Leu Ser Thr Tyr Gln Tyr Leu
    210                 215                 220

Ser Ser Glu Asp Leu Leu Trp Leu Lys Gln Ile Leu Lys Ile Asp Ala
225                 230                 235                 240

Glu Leu Glu Ser Leu Met Gln Lys Leu Thr Ala Gln Pro Val Tyr Phe
                245                 250                 255

Phe Ser Gly Thr Thr Phe Leu Gly
            260
```

<210> SEQ ID NO 21
<211> LENGTH: 399
<212> TYPE: PRT
<213> ORGANISM: Artificial Sequence
<220> FEATURE:
<223> OTHER INFORMATION: Mutant version of BstE

<400> SEQUENCE: 21

```
Met Leu Ile Gln Gln Asn Leu Glu Ile Tyr Leu Asp His Ala Thr Ile
1               5                   10                  15

Pro Ser Leu Ala Cys Phe Met His Phe Ile Gln His Lys Asp Asp Val
            20                  25                  30
```

```
Asp Ser Ile Arg Leu Phe Gly Leu Ala Arg Phe Asp Ile Pro Gln Ser
        35                  40                  45

Ile Ile Asp Arg Tyr Pro Ala Asn His Leu Phe Tyr His Asn Ile Asp
    50                  55                  60

Asn Arg Asp Leu Thr Ala Val Leu Asn Gln Leu Ala Asp Ile Leu Ala
65                  70                  75                  80

Gln Glu Asn Lys Arg Phe Gln Ile Asn Leu His Leu Asn Leu Phe His
                85                  90                  95

Ser Ile Asp Leu Phe Phe Ala Ile Tyr Pro Ile Tyr Gln Gln Tyr Gln
            100                 105                 110

His Lys Ile Ser Thr Ile Gln Leu Gln Leu Tyr Asp Asp Gly Ser Ala
        115                 120                 125

Gly Ile Val Thr Gln His Ser Leu Cys Lys Ile Ala Asp Leu Glu Gln
    130                 135                 140

Leu Ile Leu Gln His Lys Asn Val Leu Leu Glu Leu Leu Thr Lys Gly
145                 150                 155                 160

Thr Ala Asn Val Pro Asn Pro Thr Leu Leu Arg Tyr Leu Trp Asn Asn
                165                 170                 175

Ile Ile Asp Ser Gln Phe His Leu Ile Ser Asp His Phe Leu Gln His
            180                 185                 190

Pro Lys Leu Gln Pro Leu Lys Arg Leu Leu Lys Arg Tyr Thr Ile Leu
        195                 200                 205

Asp Phe Thr Cys Tyr Pro Arg Phe Asn Ala Glu Gln Lys Gln Leu Leu
    210                 215                 220

Lys Glu Ile Leu His Ile Ser Asn Glu Leu Glu Asn Leu Leu Lys Leu
225                 230                 235                 240

Leu Lys Gln His Asn Thr Phe Leu Phe Thr Gly Thr Thr Ala Phe Asn
                245                 250                 255

Leu Asp Gln Glu Lys Leu Asp Leu Leu Thr Gln Leu His Ile Leu Leu
            260                 265                 270

Leu Asn Glu His Gln Asn Pro His Ser Thr His Tyr Ile Gly Asn Asn
        275                 280                 285

Tyr Leu Leu Leu Ile Lys Gly His Ala Asn Ser Pro Ala Leu Asn His
    290                 295                 300

Thr Leu Ala Leu His Phe Pro Asp Ala Ile Phe Leu Pro Ala Asn Ile
305                 310                 315                 320

Pro Phe Glu Ile Phe Ala Met Leu Gly Phe Thr Pro Asn Lys Met Gly
                325                 330                 335

Gly Phe Ala Ser Thr Ser Tyr Ile Asn Tyr Pro Thr Glu Asn Ile Asn
            340                 345                 350

His Leu Phe Phe Leu Thr Ser Asp Gln Pro Ser Ile Arg Thr Lys Trp
        355                 360                 365

Leu Asp Tyr Glu Lys Gln Phe Gly Leu Met Tyr Ser Leu Leu Ala Met
    370                 375                 380

Gln Lys Ile Asn Glu Asp Gln Ala Phe Met Cys Thr Ile His Asn
385                 390                 395
```

<210> SEQ ID NO 22
<211> LENGTH: 498
<212> TYPE: PRT
<213> ORGANISM: Artificial Sequence
<220> FEATURE:
<223> OTHER INFORMATION: Mutant version of BstH

<400> SEQUENCE: 22

```
Met Lys Arg Leu Phe Arg Leu Phe Leu Cys Leu Ala Leu Leu Ser Gly
1               5                   10                  15

Thr Ala Ala Cys Ser Asp Asp Glu Val Ser Gln Asn Leu Ile Val Ile
            20                  25                  30

Asn Gly Gly Glu His Phe Leu Ser Leu Asp Gly Leu Ala Arg Ala Gly
        35                  40                  45

Lys Ile Ser Val Leu Ala Pro Ala Pro Trp Arg Val Thr Lys Ala Ala
    50                  55                  60

Gly Asp Thr Trp Phe Arg Leu Ser Ala Thr Glu Gly Pro Ala Gly Tyr
65                  70                  75                  80

Ser Glu Val Glu Leu Ser Leu Asp Glu Asn Pro Gly Ala Ala Arg Ser
                85                  90                  95

Ala Gln Leu Ala Phe Ala Cys Gly Asp Ala Ile Val Pro Phe Arg Leu
            100                 105                 110

Ser Gln Gly Ala Leu Ser Ala Gly Tyr Asp Ser Pro Asp Tyr Tyr Phe
        115                 120                 125

Tyr Val Thr His Gly Thr Met Pro Thr Leu Tyr Ala Gly Ile His Leu
    130                 135                 140

Leu Ser His Asp Lys Pro Gly Tyr Val Phe Tyr Ser Arg Ser Lys Thr
145                 150                 155                 160

Phe Asp Pro Ala Glu Phe Pro Ala Arg Ala Glu Val Thr Thr Ala Ala
                165                 170                 175

Asp Arg Thr Ala Asp Ala Thr Gln Ala Glu Met Glu Ala Met Ala Arg
            180                 185                 190

Glu Met Lys Arg Arg Ile Leu Glu Ile Asn Ser Ala Asp Pro Thr Ala
        195                 200                 205

Val Phe Gly Leu Tyr Val Asp Asp Leu Arg Cys Arg Ile Gly Tyr Asp
    210                 215                 220

Trp Phe Val Ala Gln Gly Ile Asp Ser Ala Arg Val Lys Val Ser Met
225                 230                 235                 240

Leu Ser Asp Gly Thr Gly Thr Tyr Asn Ala Phe Tyr Asn Tyr Phe Gly
                245                 250                 255

Asp Ala Ala Thr Ala Glu Gln Asn Trp Glu Ser Tyr Ala Ser Glu Val
            260                 265                 270

Glu Ala Leu Asp Trp Asn His Gly Gly Arg Tyr Pro Glu Thr Arg Ser
        275                 280                 285

Leu Pro Glu Phe Glu Ser Tyr Thr Trp Pro Tyr Tyr Leu Ser Thr Arg
    290                 295                 300

Pro Asp Tyr Arg Leu Val Val Gln Asp Gly Ser Leu Leu Glu Ser Ser
305                 310                 315                 320

Cys Pro Phe Ile Thr Glu Lys Leu Gly Glu Met Glu Ile Glu Ser Ile
                325                 330                 335

Gln Pro Tyr Glu Met Leu Ser Ala Leu Pro Glu Ser Ser Arg Lys Arg
            340                 345                 350

Phe Tyr Asp Met Ala Gly Phe Asp Tyr Asp Lys Phe Ala Ala Leu Phe
        355                 360                 365

Asp Ala Ser Pro Lys Lys Asn Leu Ile Ile Ile Gly Thr Ser His Ala
    370                 375                 380

Asp Asp Ala Ser Ala Arg Leu Gln Arg Asp Tyr Val Ala Arg Ile Met
385                 390                 395                 400

Glu Gln Tyr Gly Ala Gln Tyr Asp Val Phe Phe Lys Pro His Pro Ala
                405                 410                 415
```

-continued

```
Asp Thr Thr Ser Ala Gly Tyr Glu Thr Glu Phe Pro Gly Leu Thr Leu
            420                 425                 430

Leu Pro Gly Gln Met Pro Phe Glu Ile Phe Val Trp Ser Leu Ile Asp
        435                 440                 445

Arg Val Asp Met Ile Gly Gly Tyr Pro Ser Thr Val Phe Leu Thr Val
    450                 455                 460

Pro Val Asp Lys Val Arg Phe Ile Phe Ala Ala Asp Ala Ala Ser Leu
465                 470                 475                 480

Val Arg Pro Leu Asn Ile Leu Phe Arg Asp Ala Thr Asp Val Glu Trp
                485                 490                 495

Met Gln


<210> SEQ ID NO 23
<211> LENGTH: 410
<212> TYPE: PRT
<213> ORGANISM: Artificial Sequence
<220> FEATURE:
<223> OTHER INFORMATION: Mutant version of BstI

<400> SEQUENCE: 23

Met Glu Phe Cys Lys Met Ala Thr Thr Gln Lys Ile Cys Val Tyr Leu
1               5                   10                  15

Asp His Ala Thr Ile Pro Ser Leu Asn Tyr Ile Leu His Phe Ala Gln
            20                  25                  30

His Phe Glu Asp Gln Glu Thr Ile Arg Leu Phe Gly Leu Ser Arg Phe
        35                  40                  45

His Ile Pro Glu Ser Val Ile Gln Arg Tyr Pro Lys Gly Val Val Gln
    50                  55                  60

Phe Tyr Pro Asn Gln Glu Lys Asp Phe Ser Ala Leu Leu Leu Ala Leu
65                  70                  75                  80

Lys Asn Ile Leu Ile Glu Val Lys Gln Gln Gln Arg Lys Cys Glu Ile
                85                  90                  95

Glu Leu His Leu Asn Leu Phe His Tyr Gln Leu Leu Leu Leu Pro Phe
            100                 105                 110

Leu Ser Leu Tyr Leu Asp Thr Gln Asp Tyr Cys His Leu Thr Leu Lys
        115                 120                 125

Phe Tyr Asp Asp Gly Ser Ala Ala Ile Ser Ala Leu Gln Glu Leu Ala
    130                 135                 140

Leu Ala Pro Asp Leu Ala Ala Gln Ile Gln Phe Glu Lys Gln Gln Phe
145                 150                 155                 160

Asp Glu Leu Val Val Lys Lys Ser Phe Lys Leu Ser Leu Leu Ser Arg
                165                 170                 175

Tyr Phe Trp Gly Lys Leu Phe Glu Ser Glu Tyr Ile Trp Phe Asn Gln
            180                 185                 190

Ala Ile Leu Gln Lys Ala Glu Leu Gln Ile Leu Lys Gln Glu Ile Ser
        195                 200                 205

Ser Ser Arg Gln Met Asp Phe Ala Ile Tyr Gln Gln Met Ser Asp Glu
    210                 215                 220

Gln Lys Gln Leu Val Leu Glu Ile Leu Asn Ile Asp Leu Asn Lys Val
225                 230                 235                 240

Ala Tyr Leu Lys Gln Leu Met Glu Asn Gln Pro Ser Phe Leu Phe Leu
                245                 250                 255

Gly Thr Thr Leu Phe Asn Ile Thr Gln Glu Thr Lys Thr Trp Leu Met
            260                 265                 270

Gln Met His Val Asp Leu Ile Gln Gln Tyr Cys Leu Pro Ser Gly Gln
```

-continued

```
        275                 280                 285

Phe Phe Asn Asn Lys Ala Gly Tyr Leu Cys Phe Tyr Lys Gly His Pro
    290                 295                 300

Asn Glu Lys Glu Met Asn Gln Met Ile Leu Ser Gln Phe Lys Asn Leu
305                 310                 315                 320

Ile Ala Leu Pro Asp Asp Ile Pro Leu Glu Ile Leu Leu Leu Leu Gly
                325                 330                 335

Val Ile Pro Ser Lys Val Gly Gly Phe Ala Ser Ser Ala Leu Phe Asn
            340                 345                 350

Phe Thr Pro Ala Gln Ile Glu Asn Ile Ile Phe Phe Thr Pro Arg Tyr
        355                 360                 365

Phe Glu Lys Asp Asn Arg Leu His Ala Thr Gln Tyr Arg Leu Met Gln
    370                 375                 380

Gly Leu Ile Glu Leu Gly Tyr Leu Asp Ala Glu Lys Ser Val Thr His
385                 390                 395                 400

Phe Glu Ile Met Gln Leu Leu Thr Lys Glu
                405                 410

<210> SEQ ID NO 24
<211> LENGTH: 367
<212> TYPE: PRT
<213> ORGANISM: Artificial Sequence
<220> FEATURE:
<223> OTHER INFORMATION: Mutant version of BstJ

<400> SEQUENCE: 24

Met Leu Val Asn Asn Gln Ser His Asn Pro Lys Leu Ile Cys Trp Gln
1               5                   10                  15

Arg His Pro Val Asn Asp Glu Ala Leu Leu Gln Gly Ile Asn Ala Ala
            20                  25                  30

Ser Phe Val Ser Ile Ala Ser Leu Cys Gln His Ala Ala Thr Leu Leu
        35                  40                  45

Ala Gly His Pro His Ser His Ile Thr Ile Tyr Gly Asn Thr Tyr Trp
    50                  55                  60

Ser Lys Asp Leu Ala Arg Leu Ile Arg Tyr Leu Thr Arg Ile Ser Gly
65                  70                  75                  80

Val Glu Ile Lys Lys Leu Glu Leu Ile Asp Asp Gly Ser Ser Glu Tyr
                85                  90                  95

Gln Lys Met Phe Tyr Trp Gln Arg Leu His Ser Glu Glu Gln Thr Arg
            100                 105                 110

Asp Leu Ala Thr Gly Leu Lys Asn Leu Lys Ser Tyr Leu Ser Gly Asn
        115                 120                 125

Asp Asn Lys Leu Leu Arg Leu Leu Thr Gly His Ser Asn Lys Leu Pro
    130                 135                 140

Arg Arg Leu Ser Ser Phe Met Asn Trp His Gln Leu Phe Pro Thr Thr
145                 150                 155                 160

Tyr His Met Leu Arg Met Asp Tyr Leu Asp Lys Pro Glu Leu His Gln
                165                 170                 175

Leu Lys Gln Tyr Leu Gly Asn Asn Ala Gln Gln Ile Arg Trp Asn Tyr
            180                 185                 190

Ile Ala Asp Asn Leu Phe Asp Asp Glu Gln Gln Ser Leu Phe Tyr Gln
        195                 200                 205

Leu Leu Gly Ile Ser Leu Ala Glu Gln Lys Gln Leu Arg Ala Gly Arg
    210                 215                 220

Gln Gln Leu His Asp Phe Met Phe Ile Gly Val Asp Ser Ser Asn Ala
```

```
225                 230                 235                 240

Ser Ser Lys Leu Gln Ile Asn Val Ile Ala Asp Ser Arg Gln Glu Ser
                245                 250                 255

Gly Ile Ile Pro Thr Ile Thr Ala Lys Lys Met Leu Phe Lys Gly His
            260                 265                 270

Pro Phe Ala Asn Phe Asn Gln Thr Ile Val Asp Ala His Gln Met Gly
        275                 280                 285

Glu Met Pro Ala Met Ile Pro Phe Glu Thr Leu Ile Met Thr Gly Asn
    290                 295                 300

Leu Pro Gln Lys Val Gly Gly Met Ala Ser Ser Leu Tyr Phe Ser Leu
305                 310                 315                 320

Pro Asn Asn Tyr His Ile Glu Tyr Ile Val Phe Ser Gly Ser Lys Lys
                325                 330                 335

Asp Leu Glu Gln His Ala Leu Leu Gln Ile Met Leu Tyr Leu Lys Val
            340                 345                 350

Ile Ser Pro Glu Arg Val Tyr Phe Ser Glu Gln Phe Lys Ser Cys
        355                 360                 365


<210> SEQ ID NO 25
<211> LENGTH: 318
<212> TYPE: PRT
<213> ORGANISM: Artificial Sequence
<220> FEATURE:
<223> OTHER INFORMATION: Mutant version of BstM

<400> SEQUENCE: 25

Met Lys Lys Pro Leu Ile Ile Ala Gly Asn Gly Pro Ser Ile Lys Asp
1               5                   10                  15

Leu Asp Tyr Ser Leu Phe Pro Lys Asp Phe Glu Val Phe Arg Cys Asn
            20                  25                  30

Gln Phe Tyr Phe Glu Asp Lys Tyr Tyr Leu Gly Arg Glu Ile Lys Gly
        35                  40                  45

Val Phe Phe Asn Pro Cys Val Leu Ser Ser Gln Met Gln Thr Ala Gln
    50                  55                  60

Tyr Leu Met Asp Asn Gly Glu Tyr Ser Ile Glu Arg Phe Phe Cys Ser
65                  70                  75                  80

Val Ser Thr Asp Arg His Asp Phe Asp Gly Asp Tyr Gln Thr Ile Leu
                85                  90                  95

Pro Val Glu Gly Tyr Leu His Ala His Tyr Pro Phe Val Cys Asp Thr
            100                 105                 110

Phe Ser Leu Phe Lys Gly His Glu Glu Ile Leu Arg His Val Lys Tyr
        115                 120                 125

His Leu Lys Thr Tyr Ser Lys Glu Leu Ser Ala Gly Val Leu Met Leu
    130                 135                 140

Leu Ser Ala Val Val Leu Gly Tyr Lys Glu Ile Tyr Leu Val Gly Ile
145                 150                 155                 160

Asp Phe Gly Ala Ser Ser Trp Gly His Phe Tyr Asp Glu Ser Gln Ser
                165                 170                 175

Gln His Phe Ser Asn His Met Ala Asp Cys His Asn Ile Tyr Tyr Asp
            180                 185                 190

Met Phe Thr Ile Cys Leu Cys Gln Lys Tyr Ala Lys Leu Tyr Ala Leu
        195                 200                 205

Ala Pro Asn Ser Pro Leu Arg His Ile Leu Ala Leu Asn Pro Ala Ala
    210                 215                 220

Lys Tyr His Phe Glu Leu Leu Asp Lys Pro Ile Gly Tyr Thr Ser Asp
```

-continued

```
225                 230                 235                 240

Leu Ile Val Ser Leu Pro Leu Glu Glu Lys Leu Leu Glu Phe Lys Asn
                245                 250                 255

Ile Glu Glu Lys Leu Leu Glu Phe Lys Asn Ile Glu Glu Lys Leu Leu
            260                 265                 270

Glu Phe Lys Asn Ile Glu Glu Lys Leu Leu Val Asn Arg Leu Lys Asn
        275                 280                 285

Ile Leu Arg Lys Ile Lys Arg Lys Ile Leu Pro Phe Trp Gly Gly Gly
    290                 295                 300

Gly Asn Thr His Leu Lys Val Ser Phe Arg Trp Gly Val Ala
305                 310                 315


<210> SEQ ID NO 26
<211> LENGTH: 314
<212> TYPE: PRT
<213> ORGANISM: Artificial Sequence
<220> FEATURE:
<223> OTHER INFORMATION: Mutant version of BstN

<400> SEQUENCE: 26

Met Ser Glu Lys Ile Phe Ser Gln Val Asp Glu Lys Asn Gln Lys Lys
1               5                   10                  15

Pro Leu Ile Ile Ala Gly Asn Gly Pro Ser Ile Lys Asp Leu Asp Tyr
            20                  25                  30

Ser Leu Phe Pro Lys Asp Phe Asp Val Phe Arg Cys Asn Gln Phe Tyr
        35                  40                  45

Phe Glu Asp Lys Tyr Tyr Leu Gly Lys Glu Val Lys Gly Val Phe Phe
    50                  55                  60

Asn Pro Cys Val Phe His Asn Gln Met Asn Thr Ala Lys His Leu Ile
65                  70                  75                  80

Asp Asn Asn Glu Tyr Tyr Ile Glu Gln Phe Phe Cys Ser Val Ser Lys
                85                  90                  95

Glu Gln His Asp Phe Asn Gly Asp Tyr Gln Thr Ile Leu Ser Val Asp
            100                 105                 110

Glu Tyr Leu His Ala Asn Tyr Pro Phe Val Arg Asp Thr Phe Ser Leu
        115                 120                 125

Phe Gly Glu His Glu Glu Ile Leu Asn His Val Lys Tyr His Leu Lys
    130                 135                 140

Thr Tyr Ser Lys Glu Leu Ser Ala Gly Val Leu Met Leu Leu Ser Ala
145                 150                 155                 160

Ile Val Leu Gly Tyr Lys Glu Ile Tyr Leu Val Gly Val Asp Phe Gly
                165                 170                 175

Ala Asn Ser Trp Gly His Phe Tyr Asp Asp Asn Gln Ser Gln His Phe
            180                 185                 190

Ile Asn His Met Ala Asp Cys His Asn Ile Tyr Tyr Asp Met Leu Thr
        195                 200                 205

Ile Tyr Leu Cys Gln Lys Tyr Ala Lys Leu Tyr Ala Leu Val Pro Asn
    210                 215                 220

Ser Pro Leu Asn His Leu Leu Pro Leu Asn Leu Ala Ala Asn His Val
225                 230                 235                 240

Phe Glu Leu Leu Asp Lys Pro Ile Gly Tyr Thr Ser Asp Leu Ile Val
                245                 250                 255

Ser Ser Pro Leu Glu Glu Lys Leu Leu Glu Ser Lys Asn Ile Asp Glu
            260                 265                 270

Arg Phe Ser Gln Asn Lys Ser Phe Lys Asn Tyr Leu Gln Arg Leu Lys
```

```
        275                 280                 285

Asp Lys Phe Leu Gln Met Ile Phe Arg Gly Gly Gly Val Ile Thr Ile
    290                 295                 300

Pro Arg Val Ile Phe Lys Gly Lys Phe Ala
305                 310


<210> SEQ ID NO 27
<211> LENGTH: 397
<212> TYPE: PRT
<213> ORGANISM: Artificial Sequence
<220> FEATURE:
<223> OTHER INFORMATION: Mutant version of BstC

<400> SEQUENCE: 27

Met Glu Ile Tyr Leu Asp His Ala Ser Leu Pro Ser Leu Asn Met Ile
1               5                   10                  15

Leu Asn Leu Val Glu Asn Lys Asn Asn Glu Lys Val Glu Arg Ile Ile
            20                  25                  30

Gly Phe Glu Arg Phe Asp Phe Asn Lys Glu Ile Leu Asn Ser Phe Ser
        35                  40                  45

Lys Glu Arg Ile Glu Phe Ser Lys Val Ser Ile Leu Asp Ile Lys Glu
    50                  55                  60

Phe Ser Asp Lys Leu Tyr Leu Asn Ile Glu Lys Ser Asp Thr Pro Val
65                  70                  75                  80

Asp Leu Ile Ile His Thr Asn Leu Asp His Ser Val Arg Ser Leu Leu
                85                  90                  95

Ser Ile Phe Lys Thr Leu Ser Pro Leu Phe His Lys Ile Asn Ile Glu
            100                 105                 110

Lys Leu Tyr Leu Tyr Asp Asp Gly Ser Val Asn Tyr Val Asp Leu Tyr
        115                 120                 125

Gln His Arg Gln Glu Asn Ile Ser Ala Ile Leu Ile Glu Ala Gln Lys
    130                 135                 140

Lys Leu Lys Asp Ala Leu Glu Asn Arg Glu Thr Asp Thr Asp Lys Leu
145                 150                 155                 160

His Ser Leu Thr Arg Tyr Thr Trp His Lys Ile Phe Pro Thr Glu Tyr
                165                 170                 175

Ile Leu Leu Arg Pro Asp Tyr Leu Asp Ile Asp Glu Lys Met Gln Pro
            180                 185                 190

Leu Lys His Phe Leu Ser Asp Thr Ile Val Ser Met Asp Leu Ser Arg
        195                 200                 205

Phe Ser His Phe Ser Lys Asn Gln Lys Glu Leu Phe Leu Lys Ile Thr
    210                 215                 220

His Phe Asp Gln Asn Ile Phe Asn Glu Leu Asn Ile Gly Thr Lys Asn
225                 230                 235                 240

Lys Glu Tyr Lys Thr Phe Ile Phe Thr Gly Thr Thr Thr Trp Glu Lys
                245                 250                 255

Asp Lys Lys Lys Arg Leu Asn Asn Ala Lys Leu Gln Thr Glu Ile Leu
            260                 265                 270

Glu Ser Phe Ile Lys Pro Asn Gly Lys Phe Tyr Leu Gly Asn Asp Ile
        275                 280                 285

Lys Ile Phe Phe Lys Gly His Pro Lys Gly Asp Asp Ile Asn Asp Tyr
    290                 295                 300

Ile Ile Arg Lys Thr Gly Ala Glu Lys Ile Pro Ala Asn Ile Pro Phe
305                 310                 315                 320

Glu Val Leu Met Met Thr Asn Ser Leu Pro Asp Tyr Val Gly Gly Ile
```

```
                325                 330                 335

Met Ser Thr Val Tyr Phe Ser Leu Pro Pro Lys Asn Ile Asp Lys Val
            340                 345                 350

Val Phe Leu Gly Ser Glu Lys Ile Lys Asn Glu Asn Asp Ala Lys Ser
        355                 360                 365

Gln Thr Leu Ser Lys Leu Met Leu Met Leu Asn Val Ile Thr Pro Glu
    370                 375                 380

Gln Ile Phe Phe Glu Glu Met Pro Asn Pro Ile Asn Phe
385                 390                 395


<210> SEQ ID NO 28
<211> LENGTH: 397
<212> TYPE: PRT
<213> ORGANISM: Artificial Sequence
<220> FEATURE:
<223> OTHER INFORMATION: Mutant version of BstC

<400> SEQUENCE: 28

Met Glu Ile Tyr Leu Asp His Ala Ser Leu Pro Ser Leu Asn Met Ile
1               5                   10                  15

Leu Asn Leu Val Glu Asn Lys Asn Asn Glu Lys Val Glu Arg Ile Ile
            20                  25                  30

Gly Phe Glu Arg Phe Asp Phe Asn Lys Glu Ile Leu Asn Ser Phe Ser
        35                  40                  45

Lys Glu Arg Ile Glu Phe Ser Lys Val Ser Ile Leu Asp Ile Lys Glu
    50                  55                  60

Phe Ser Asp Lys Leu Tyr Leu Asn Ile Glu Lys Ser Asp Thr Pro Val
65                  70                  75                  80

Asp Leu Ile Ile His Thr Asn Leu Asp His Ser Val Arg Ser Leu Leu
                85                  90                  95

Ser Ile Phe Lys Thr Leu Ser Pro Leu Phe His Lys Ile Asn Ile Glu
            100                 105                 110

Lys Leu Tyr Leu Tyr Asp Asp Gly Ser Leu Asn Tyr Val Asp Leu Tyr
        115                 120                 125

Gln His Arg Gln Glu Asn Ile Ser Ala Ile Leu Ile Glu Ala Gln Lys
    130                 135                 140

Lys Leu Lys Asp Ala Leu Glu Asn Arg Glu Thr Asp Thr Asp Lys Leu
145                 150                 155                 160

His Ser Leu Thr Arg Tyr Thr Trp His Lys Ile Phe Pro Thr Glu Tyr
                165                 170                 175

Ile Leu Leu Arg Pro Asp Tyr Leu Asp Ile Asp Glu Lys Met Gln Pro
            180                 185                 190

Leu Lys His Phe Leu Ser Asp Thr Ile Val Ser Met Asp Leu Ser Arg
        195                 200                 205

Phe Ser His Phe Ser Lys Asn Gln Lys Glu Leu Phe Leu Lys Ile Thr
    210                 215                 220

His Phe Asp Gln Asn Ile Phe Asn Glu Leu Asn Ile Gly Thr Lys Asn
225                 230                 235                 240

Lys Glu Tyr Lys Thr Phe Ile Phe Thr Gly Thr Thr Thr Trp Glu Lys
                245                 250                 255

Asp Lys Lys Lys Arg Leu Asn Asn Ala Lys Leu Gln Thr Glu Ile Leu
            260                 265                 270

Glu Ser Phe Ile Lys Pro Asn Gly Lys Phe Tyr Leu Gly Asn Asp Ile
        275                 280                 285

Lys Ile Phe Phe Lys Gly His Pro Lys Gly Asp Asp Ile Asn Asp Tyr
```

```
    290                 295                 300

Ile Ile Arg Lys Thr Gly Ala Glu Lys Ile Pro Ala Asn Ile Pro Phe
305                 310                 315                 320

Glu Val Leu Met Met Thr Asn Ser Leu Pro Asp Tyr Val Gly Gly Ile
                325                 330                 335

Met Ser Thr Val Tyr Phe Ser Leu Pro Pro Lys Asn Ile Asp Lys Val
            340                 345                 350

Val Phe Leu Gly Ser Glu Lys Ile Lys Asn Glu Asn Asp Ala Lys Ser
        355                 360                 365

Gln Thr Leu Ser Lys Leu Met Leu Met Leu Asn Val Ile Thr Pro Glu
    370                 375                 380

Gln Ile Phe Phe Glu Glu Met Pro Asn Pro Ile Asn Phe
385                 390                 395


<210> SEQ ID NO 29
<211> LENGTH: 397
<212> TYPE: PRT
<213> ORGANISM: Artificial Sequence
<220> FEATURE:
<223> OTHER INFORMATION: Mutant version of BstC

<400> SEQUENCE: 29

Met Glu Ile Tyr Leu Asp His Ala Ser Leu Pro Ser Leu Asn Met Ile
1               5                   10                  15

Leu Asn Leu Val Glu Asn Lys Asn Asn Glu Lys Val Glu Arg Ile Ile
            20                  25                  30

Gly Phe Glu Arg Phe Asp Phe Asn Lys Glu Ile Leu Asn Ser Phe Ser
        35                  40                  45

Lys Glu Arg Ile Glu Phe Ser Lys Val Ser Ile Leu Asp Ile Lys Glu
    50                  55                  60

Phe Ser Asp Lys Leu Tyr Leu Asn Ile Glu Lys Ser Asp Thr Pro Val
65                  70                  75                  80

Asp Leu Ile Ile His Thr Asn Leu Asp His Ser Val Arg Ser Leu Leu
                85                  90                  95

Ser Ile Phe Lys Thr Leu Ser Pro Leu Phe His Lys Ile Asn Ile Glu
            100                 105                 110

Lys Leu Tyr Leu Tyr Asp Asp Gly Ser Met Asn Tyr Val Asp Leu Tyr
        115                 120                 125

Gln His Arg Gln Glu Asn Ile Ser Ala Ile Leu Ile Glu Ala Gln Lys
    130                 135                 140

Lys Leu Lys Asp Ala Leu Glu Asn Arg Glu Thr Asp Thr Asp Lys Leu
145                 150                 155                 160

His Ser Leu Thr Arg Tyr Thr Trp His Lys Ile Phe Pro Thr Glu Tyr
                165                 170                 175

Ile Leu Leu Arg Pro Asp Tyr Leu Asp Ile Asp Glu Lys Met Gln Pro
            180                 185                 190

Leu Lys His Phe Leu Ser Asp Thr Ile Val Ser Met Asp Leu Ser Arg
        195                 200                 205

Phe Ser His Phe Ser Lys Asn Gln Lys Glu Leu Phe Leu Lys Ile Thr
    210                 215                 220

His Phe Asp Gln Asn Ile Phe Asn Glu Leu Asn Ile Gly Thr Lys Asn
225                 230                 235                 240

Lys Glu Tyr Lys Thr Phe Ile Phe Thr Gly Thr Thr Thr Trp Glu Lys
                245                 250                 255

Asp Lys Lys Lys Arg Leu Asn Asn Ala Lys Leu Gln Thr Glu Ile Leu
```

```
            260                 265                 270

Glu Ser Phe Ile Lys Pro Asn Gly Lys Phe Tyr Leu Gly Asn Asp Ile
        275                 280                 285

Lys Ile Phe Phe Lys Gly His Pro Lys Gly Asp Asp Ile Asn Asp Tyr
    290                 295                 300

Ile Ile Arg Lys Thr Gly Ala Glu Lys Ile Pro Ala Asn Ile Pro Phe
305                 310                 315                 320

Glu Val Leu Met Met Thr Asn Ser Leu Pro Asp Tyr Val Gly Gly Ile
                325                 330                 335

Met Ser Thr Val Tyr Phe Ser Leu Pro Pro Lys Asn Ile Asp Lys Val
            340                 345                 350

Val Phe Leu Gly Ser Glu Lys Ile Lys Asn Glu Asn Asp Ala Lys Ser
        355                 360                 365

Gln Thr Leu Ser Lys Leu Met Leu Met Leu Asn Val Ile Thr Pro Glu
    370                 375                 380

Gln Ile Phe Phe Glu Glu Met Pro Asn Pro Ile Asn Phe
385                 390                 395


<210> SEQ ID NO 30
<211> LENGTH: 397
<212> TYPE: PRT
<213> ORGANISM: Artificial Sequence
<220> FEATURE:
<223> OTHER INFORMATION: Mutant version of BstC

<400> SEQUENCE: 30

Met Glu Ile Tyr Leu Asp His Ala Ser Leu Pro Ser Leu Asn Met Ile
1               5                   10                  15

Leu Asn Leu Val Glu Asn Lys Asn Asn Glu Lys Val Glu Arg Ile Ile
            20                  25                  30

Gly Phe Glu Arg Phe Asp Phe Asn Lys Glu Ile Leu Asn Ser Phe Ser
        35                  40                  45

Lys Glu Arg Ile Glu Phe Ser Lys Val Ser Ile Leu Asp Ile Lys Glu
    50                  55                  60

Phe Ser Asp Lys Leu Tyr Leu Asn Ile Glu Lys Ser Asp Thr Pro Val
65                  70                  75                  80

Asp Leu Ile Ile His Thr Asn Leu Asp His Ser Val Arg Ser Leu Leu
                85                  90                  95

Ser Ile Phe Lys Thr Leu Ser Pro Leu Phe His Lys Ile Asn Ile Glu
            100                 105                 110

Lys Leu Tyr Leu Tyr Asp Asp Gly Ser Phe Asn Tyr Val Asp Leu Tyr
        115                 120                 125

Gln His Arg Gln Glu Asn Ile Ser Ala Ile Leu Ile Glu Ala Gln Lys
    130                 135                 140

Lys Leu Lys Asp Ala Leu Glu Asn Arg Glu Thr Asp Thr Asp Lys Leu
145                 150                 155                 160

His Ser Leu Thr Arg Tyr Thr Trp His Lys Ile Phe Pro Thr Glu Tyr
                165                 170                 175

Ile Leu Leu Arg Pro Asp Tyr Leu Asp Ile Asp Glu Lys Met Gln Pro
            180                 185                 190

Leu Lys His Phe Leu Ser Asp Thr Ile Val Ser Met Asp Leu Ser Arg
        195                 200                 205

Phe Ser His Phe Ser Lys Asn Gln Lys Glu Leu Phe Leu Lys Ile Thr
    210                 215                 220

His Phe Asp Gln Asn Ile Phe Asn Glu Leu Asn Ile Gly Thr Lys Asn
```

-continued

```
225                 230                 235                 240

Lys Glu Tyr Lys Thr Phe Ile Phe Thr Gly Thr Thr Thr Trp Glu Lys
                245                 250                 255

Asp Lys Lys Lys Arg Leu Asn Asn Ala Lys Leu Gln Thr Glu Ile Leu
            260                 265                 270

Glu Ser Phe Ile Lys Pro Asn Gly Lys Phe Tyr Leu Gly Asn Asp Ile
        275                 280                 285

Lys Ile Phe Phe Lys Gly His Pro Lys Gly Asp Asp Ile Asn Asp Tyr
    290                 295                 300

Ile Ile Arg Lys Thr Gly Ala Glu Lys Ile Pro Ala Asn Ile Pro Phe
305                 310                 315                 320

Glu Val Leu Met Met Thr Asn Ser Leu Pro Asp Tyr Val Gly Gly Ile
                325                 330                 335

Met Ser Thr Val Tyr Phe Ser Leu Pro Pro Lys Asn Ile Asp Lys Val
            340                 345                 350

Val Phe Leu Gly Ser Glu Lys Ile Lys Asn Glu Asn Asp Ala Lys Ser
        355                 360                 365

Gln Thr Leu Ser Lys Leu Met Leu Met Leu Asn Val Ile Thr Pro Glu
    370                 375                 380

Gln Ile Phe Phe Glu Glu Met Pro Asn Pro Ile Asn Phe
385                 390                 395
```